US011835505B2

(12) United States Patent
Clarke

(10) Patent No.: US 11,835,505 B2
(45) Date of Patent: *Dec. 5, 2023

(54) QUANTITATION OF TAMOXIFEN AND METABOLITES THEREOF BY MASS SPECTROMETRY

(71) Applicant: QUEST DIAGNOSTICS INVESTMENTS INCORPORATED, Wilmington, DE (US)

(72) Inventor: Nigel Clarke, Vista, CA (US)

(73) Assignee: QUEST DIAGNOSTICS INVESTMENTS INCORPORATED, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/893,950

(22) Filed: Aug. 23, 2022

(65) Prior Publication Data

US 2023/0114103 A1    Apr. 13, 2023

Related U.S. Application Data

(63) Continuation of application No. 17/093,472, filed on Nov. 9, 2020, now Pat. No. 11,428,682, which is a continuation of application No. 15/830,812, filed on Dec. 4, 2017, now Pat. No. 10,830,746, which is a continuation of application No. 15/284,248, filed on Oct. 3, 2016, now Pat. No. 9,835,606, which is a continuation of application No. 14/710,311, filed on May 12, 2015, now Pat. No. 9,459,267.

(60) Provisional application No. 61/992,214, filed on May 12, 2014.

(51) Int. Cl.
| | |
|---|---|
| *G01N 33/94* | (2006.01) |
| *G01N 33/15* | (2006.01) |
| *G01N 33/49* | (2006.01) |
| *G01N 33/48* | (2006.01) |
| *G01N 30/72* | (2006.01) |
| *H01J 49/00* | (2006.01) |
| *H01J 49/10* | (2006.01) |

(52) U.S. Cl.
CPC ......... *G01N 33/15* (2013.01); *G01N 30/7233* (2013.01); *G01N 33/49* (2013.01); *G01N 33/94* (2013.01); *H01J 49/004* (2013.01); *H01J 49/0031* (2013.01); *H01J 49/0045* (2013.01); *H01J 49/10* (2013.01); *G01N 33/48* (2013.01); *H01J 49/00* (2013.01); *Y10T 436/17* (2015.01); *Y10T 436/24* (2015.01); *Y10T 436/25125* (2015.01); *Y10T 436/25375* (2015.01)

(58) Field of Classification Search
CPC .... G01N 30/02; G01N 30/72; G01N 30/7233; G01N 33/48; G01N 33/49; G01N 33/15; G01N 33/94; Y10T 436/17; Y10T 436/20; Y10T 436/24; Y10T 436/25; Y10T 436/25125; Y10T 436/25375; Y10T 436/255; H01J 49/00; H01J 49/0036; H01J 49/004; H01J 49/26; H01J 49/0095; H01J 49/0031; H01J 49/0045; H01J 49/10
USPC ......... 436/63, 106, 127, 161, 173, 174, 175, 436/177, 178; 422/70, 527, 534; 250/282, 283, 285; 514/648
See application file for complete search history.

(56) References Cited

U.S. PATENT DOCUMENTS

| | | | |
|---|---|---|---|
| 5,384,260 A | 1/1995 | Osborne et al. | |
| 9,459,267 B2* | 10/2016 | Clarke | ................ H01J 49/0045 |
| 9,835,606 B2* | 12/2017 | Clarke | ................ H01J 49/0031 |
| 10,830,746 B2* | 11/2020 | Clarke | ................ G01N 33/49 |
| 11,428,682 B2* | 8/2022 | Clarke | ................ G01N 33/49 |
| 2009/0186944 A1 | 7/2009 | Rouanet et al. | |

FOREIGN PATENT DOCUMENTS

| | | |
|---|---|---|
| CN | 106537139 B | 4/2019 |
| JP | 2014013258 A | 1/2014 |
| WO | 2010017499 A1 | 2/2010 |
| WO | 2012119010 A2 | 9/2012 |
| WO | 2012167126 A1 | 12/2012 |

OTHER PUBLICATIONS

Binkhorst L., et al., "Quantificationof Tamoxifen and Three of its Phase-I Metabolites in Human Plasma by LiquidChromatography/ Triple-Quadrupole Mass Spectrometry," Journal ofPharmaceutical and Biomedical Analysis, 2011, vol. 56 (5), pp. 1016-1023.
Dahmanee., et al., "An Ultra Performance Liquid Chromatography-Tandem MS Assay for TamoxifenMetabolites Profiling in Plasma: First Evidence of 4'-Hydroxylated Metabolitesin Breast Cancer Patients," Journal of chromatography B, 2010, vol. 878 (32), pp. 3402-3414.
Final Office Action dated Nov. 12, 2015 for U.S. Appl. No. 14/710,311, filed May 12, 2015.
Final Office Action dated Feb. 24, 2020 for U.S. Appl. No. 15/830,812, filed Dec. 4, 2017.
Gjerde J., et al., "Identification and Quantification of Tamoxifen and Four Metabolites in Serum by Liquid Chromatography-Tandem Mass Spectrometry," Journal of Chromatography A, 2005, vol. 1082 (1), pp. 6-14.

(Continued)

*Primary Examiner* — Maureen Wallenhorst
(74) *Attorney, Agent, or Firm* — Foley & Lardner LLP

(57) ABSTRACT

Provided are methods for determining the amount of tamoxifen and its metabolites in a sample by mass spectrometry. In some aspects, the methods provided herein determine the amount of N-Desmethyl Tamoxifen. In some aspects, the methods provided herein determine the amount of N-Desmethyl Tamoxifen and other tamoxifen metabolites. In some aspects, the methods provided herein determine the amount of tamoxifen, N-Desmethyl Tamoxifen, and other tamoxifen metabolites.

9 Claims, No Drawings

(56) References Cited

OTHER PUBLICATIONS

International Search Report and Written Opinion for Application No. PCT/US2015/030419, dated Jul. 22, 2015, 13 pages.

Jaremko M., et al., "Tamoxifen Metabolite Isomer Separation and Quantification by Liquid Chromatography-Tandem Mass Spectrometry," Analytical Chemistry, 2010, vol. 82 (24), pp. 10186-10193.

Lu W.J., et al., "The Tamoxifen Metabolite Norendoxifen is a Potent and Selective Inhibitor of Aromatase (CYP19) and a Potential Lead Compound for Novel Therapeutic Agents," Breast Cancer Research and Treatment. 2012, vol. 133 (1), pp. 99-109.

Lv W., et al., "Synthesis of Mixed (E,Z)-, (E)-, and (Z)-Norendoxifen with Dual Aromatase Inhibitory and Estrogen Receptor Modulatory Activities," Journal of Medicinal Chemistry, 2013, vol. 56 (11), pp. 4611-4618.

Non-Final Office Action dated Feb. 14, 2022 for U.S. Appl. No. 17/093,472, filed Nov. 9, 2020.

Non-Final Office Action dated Mar. 15, 2017 for U.S. Appl. No. 15/284,248, filed Oct. 3, 2016.

Non-Final Office Action dated Jan. 22, 2016 for U.S. Appl. No. 14/063,956, filed Oct. 25, 2013.

Non-Final Office Action dated Jul. 22, 2019 for U.S. Appl. No. 15/830,812, filed Dec. 4, 2017.

Non-Final Office Action dated Jul. 23, 2015 for U.S. Appl. No. 14/710,311, filed May 12, 2015.

Singh S.P., et al., "Liquid Chromatography-Mass SpectrometryMethod for the Quantification of Tamoxifen and its Metabolite4-Hydroxytamoxifen in Rat Plasma: Application to Interaction Study withBiochanin A (An Isoflavone)," Journal of chromatography B, 2011, vol. 879 (27),pp. 2845-2851.

Supplementary European Search Report for Application No. 15793289.8, dated Oct. 13, 2017.

Teunissen S.F., et al., "Development and Validation of aQuantitative Assay for the Determination of Tamoxifen and its Five Main Phase IMetabolites in Human Serum Using Liquid Chromatography Coupled With Tandem MassSpectrometry," Journal of chromatography B, 2011, vol. 879 (19), pp. 1677-1685.

Antunes M.V., et al., "Sensitive HPLC-PDA Determination of Tamoxifen and its Metabolites N-desmethyltamoxifen, 4-Hydroxytamoxifen and endoxifen in Human Plasma," Journal of Pharmaceutical and Biomedical Analysis, 2013, vol. 76(1), pp. 13-20. Retrived from the Internet https://www.sciencedirect.com/science/article/abs/pii/S0731708512006759.

Armbruster D.A., et al., "Limit of Blank, Limit of Detection and Limit of Quantitation," The Clinical Biochemist Reviews, 2008, vol. 29 (1), pp. S49-S52.

Du L., et al., "High Turbulence Liquid Chromatography Online Extraction and Tandem Mass Spectrometry for the Simultaneous Determination of Suberoylanilide Hydroxamic Acid and its Two Metabolites in Human Serum," Rapid Communications in Mass Spectrometry, 2005, vol. 19 (13), pp. 1779-1787.

Extended European Search Report for Application No. 23157017.7, dated Jul. 14, 2023, 12 Pages.

Teunissen S.F., et al., "Development and Validation of a Quantitative Assay for the Analysis of Tamoxifen With Its Four Main Metabolites and the Flavonoids Daidzein, Genistein and Glycitein in Human Serum Using Liquid Chromatography Coupled With Tandem Mass Spectrometry," Journal of Chromatography B, 2009, vol. 877 (24), pp. 2519-2529.

\* cited by examiner

QUANTITATION OF TAMOXIFEN AND METABOLITES THEREOF BY MASS SPECTROMETRY

CROSS-REFERENCE TO RELATED PATENT APPLICATIONS

This application is a continuation application of U.S. application Ser. No. 17/093,472, filed Nov. 9, 2020, now U.S. Pat. No. 11,428,682, which is a continuation application of U.S. application Ser. No. 15/830,812, filed Dec. 4, 2017, now U.S. Pat. No. 10,830,746, which is a continuation application of U.S. application Ser. No. 15/284,248, filed Oct. 3, 2016, now U.S. Pat. No. 9,835,606, which is a continuation application of U.S. application Ser. No. 14/710,311, filed May 12, 2015, now U.S. Pat. No. 9,459,267, which claims benefit of U.S. Provisional Application No. 61/992,214, filed May 12, 2014, each of which is incorporated by reference herein in its entirety.

BACKGROUND OF THE INVENTION

The following description of the background of the invention is provided simply as an aid in understanding the invention and is not admitted to describe or constitute prior art to the invention.

Tamoxifen is a standard of treatment for hormone receptor positive breast cancer patients after primary treatment. Five to ten years of tamoxifen therapy reduces the risk of recurrence and death in these patients. Yet, many patients do not complete their full course of therapy, frequently due to unpleasant side effects of the drug.

Tamoxifen is a pro-drug which is converted to the highly active Endoxifen for full effectiveness. Conversion of Tamoxifen to Endoxifen is through a metabolic pathway dependent on genetic variation, such as that in CYP2D6 (2D6). Although 2D6 genotyping has been promoted to predict response to Tamoxifen and toxicity, the direct association on an individual level is controversial.

An effective method of predicting response to Tamoxifen is needed.

SUMMARY OF THE INVENTION

The present invention provides methods for quantitation of tamoxifen and its metabolites in a sample by mass spectrometry, including tandem mass spectrometry.

In one aspect, methods are provided for determining the amount of norendoxifen in a sample by mass spectrometry, comprising (a) ionizing said norendoxifen to produce one or more norendoxifen ions detectable by mass spectrometry; (b) detecting the amount of the norendoxifen ion(s) from step by mass spectrometry; wherein the amount of the ion(s) detected is related to the amount of norendoxifen in said sample.

In one aspect, methods are provided for determining the amount of tamoxifen and metabolites thereof in a sample in a single mass spectrometry assay, comprising (a) ionizing said tamoxifen and metabolites to produce one or more ions detectable by mass spectrometry; (b) detecting the amount of the ion(s) from step by mass spectrometry; wherein the amount of the ion(s) detected is related to the amount of each of tamoxifen and metabolites in said sample.

In some embodiments, said metabolites comprise norendoxifen. In some embodiments, said metabolites comprise endoxifen or N-Desmethyl-4-Hydroxy Tamoxifen. In some embodiments, said metabolites comprise 4'-Hydroxy Tamoxifen. In some embodiments, said metabolites comprise 4-Hydroxy Tamoxifen. In some embodiments, said metabolites comprise N-Desmethyl-4'-Hydroxy Tamoxifen. In some embodiments, said metabolites comprise N-Desmethyl Tamoxifen. In some embodiments, said metabolites comprise metabolites selected from the group consisting of norendoxifen, endoxifen, 4'-Hydroxy Tamoxifen, 4-Hydroxy Tamoxifen, N-Desmethyl-4'-Hydroxy Tamoxifen, and N-Desmethyl-4'-Hydroxy Tamoxifen. In some embodiments, said metabolites comprise any combination of norendoxifen, endoxifen, 4'-Hydroxy Tamoxifen, 4-Hydroxy Tamoxifen, N-Desmethyl-4'-Hydroxy Tamoxifen, and N-Desmethyl Tamoxifen. In some embodiments, said metabolites comprise norendoxifen, endoxifen, 4'-Hydroxy Tamoxifen, 4-Hydroxy Tamoxifen, N-Desmethyl-4'-Hydroxy Tamoxifen, and N-Desmethyl-4'-Hydroxy Tamoxifen. In some embodiments, said metabolites comprise any combination of norendoxifen, endoxifen, 4'-Hydroxy Tamoxifen, 4-Hydroxy Tamoxifen, N-Desmethyl-4'-Hydroxy Tamoxifen, and N-Desmethyl Tamoxifen.

In one aspect, methods provided herein comprise protein precipitation. In some embodiments, methods provided herein comprise purification. In some embodiments, said purification comprises filtration. In some embodiments, said purification comprises liquid chromatography. In some embodiments, said liquid chromatography is high pressure liquid chromatography (HPLC).

In some embodiments, methods provided herein comprise detecting the amount of an internal standard. In some embodiments, said internal standard is a deuterated norendoxifen.

In some embodiments, ionization is by atmospheric pressure chemical ionization (APCI). In some embodiments, said ionization is in positive ion mode.

In some embodiments, ionization is by electrospray ionization (ESI). In some embodiments, said ionization is in positive ion mode.

In some embodiments, said sample is a serum sample.

In some embodiments, mass spectrometry is tandem mass spectrometry.

In one aspect, provided herein is a method for predicting tamoxifen response in a patient by determining the amount of tamoxifen or one or more tamoxifen metabolites. In some embodiments, a high amount of one or more tamoxifen or tamoxifen metabolites indicate a positive response to tamoxifen in a patient. In some embodiments, said metabolites comprise norendoxifen. In some embodiments, said metabolites comprise endoxifen or N-Desmethyl-4-Hydroxy Tamoxifen. In some embodiments, said metabolites comprise 4'-Hydroxy Tamoxifen. In some embodiments, said metabolites comprise 4-Hydroxy Tamoxifen. In some embodiments, said metabolites comprise N-Desmethyl-4'-Hydroxy Tamoxifen. In some embodiments, said metabolites comprise N-Desmethyl Tamoxifen. In some embodiments, said metabolites comprise norendoxifen, endoxifen, 4'-Hydroxy Tamoxifen, 4-Hydroxy Tamoxifen, N-Desmethyl-4'-Hydroxy Tamoxifen, and N-Desmethyl-4'-Hydroxy Tamoxifen.

In some embodiments, the method provided herein has sensitivity measured by limit of quantitation (LOQ). In some embodiments, the method of quantitation of tamoxifen has a limit of quantitation less than or equal to 5 ng/mL. In some embodiments, the method of quantitation of tamoxifen has a limit of quantitation less than or equal to 4 ng/mL. In some embodiments, the method of quantitation of tamoxifen has a limit of quantitation less than or equal to 3 ng/mL. In some embodiments, the method of quantitation of tamoxifen has a limit of quantitation less than or equal to 3 ng/mL. In some embodiments, the method of quantitation of tamoxifen has a limit of quantitation less than or equal to 2 ng/mL. In some embodiments, the method of quantitation of tamoxifen has a limit of quantitation less than or equal to 1.5 ng/mL.

In some embodiments, the method of quantitation of N-Desmethyl Tamoxifen has a limit of quantitation less than or equal to 5 ng/mL. In some embodiments, the method of quantitation of N-Desmethyl Tamoxifen has a limit of quantitation less than or equal to 4 ng/mL. In some embodiments, the method of quantitation of N-Desmethyl Tamoxifen has a limit of quantitation less than or equal to 3 ng/mL. In some embodiments, the method of quantitation of N-Desmethyl Tamoxifen has a limit of quantitation less than or equal to 3 ng/mL. In some embodiments, the method of quantitation of N-Desmethyl Tamoxifen has a limit of quantitation less than or equal to 2 ng/mL. In some embodiments, the method of quantitation of N-Desmethyl Tamoxifen has a limit of quantitation less than or equal to 1.5 ng/mL.

In some embodiments, the method of quantitation of 4'-Hydroxy Tamoxifen has a limit of quantitation less than or equal to 5 ng/mL. In some embodiments, the method of quantitation of 4'-Hydroxy Tamoxifen has a limit of quantitation less than or equal to 4 ng/mL. In some embodiments, the method of quantitation of 4'-Hydroxy Tamoxifen has a limit of quantitation less than or equal to 3 ng/mL. In some embodiments, the method of quantitation of 4'-Hydroxy Tamoxifen has a limit of quantitation less than or equal to 3 ng/mL. In some embodiments, the method of quantitation of 4'-Hydroxy Tamoxifen has a limit of quantitation less than or equal to 2 ng/mL. In some embodiments, the method of quantitation of 4'-Hydroxy Tamoxifen has a limit of quantitation less than or equal to 1.5 ng/mL. In some embodiments, the method of quantitation of 4'-Hydroxy Tamoxifen has a limit of quantitation less than or equal to 1 ng/mL. In some embodiments, the method of quantitation of 4'-Hydroxy Tamoxifen has a limit of quantitation less than or equal to 0.5 ng/mL. In some embodiments, the method of quantitation of 4'-Hydroxy Tamoxifen has a limit of quantitation less than or equal to 0.4 ng/mL. In some embodiments, the method of quantitation of 4'-Hydroxy Tamoxifen has a limit of quantitation less than or equal to 0.2 ng/mL.

In some embodiments, the method of quantitation of 4-Hydroxy Tamoxifen has a limit of quantitation less than or equal to 5 ng/mL. In some embodiments, the method of quantitation of 4-Hydroxy Tamoxifen has a limit of quantitation less than or equal to 4 ng/mL. In some embodiments, the method of quantitation of 4-Hydroxy Tamoxifen has a limit of quantitation less than or equal to 3 ng/mL. In some embodiments, the method of quantitation of 4-Hydroxy Tamoxifen has a limit of quantitation less than or equal to 3 ng/mL. In some embodiments, the method of quantitation of 4-Hydroxy Tamoxifen has a limit of quantitation less than or equal to 2 ng/mL. In some embodiments, the method of quantitation of 4-Hydroxy Tamoxifen has a limit of quantitation less than or equal to 1.5 ng/mL. In some embodiments, the method of quantitation of 4-Hydroxy Tamoxifen has a limit of quantitation less than or equal to 1 ng/mL. In some embodiments, the method of quantitation of 4-Hydroxy Tamoxifen has a limit of quantitation less than or equal to 0.5 ng/mL. In some embodiments, the method of quantitation of 4-Hydroxy Tamoxifen has a limit of quantitation less than or equal to 0.4 ng/mL. In some embodiments, the method of quantitation of 4-Hydroxy Tamoxifen has a limit of quantitation less than or equal to 0.2 ng/mL.

In some embodiments, the method of quantitation of N-Desmethyl-4-Hydroxy Tamoxifen (Endoxifen) has a limit of quantitation less than or equal to 5 ng/mL. In some embodiments, the method of quantitation of N-Desmethyl-4-Hydroxy Tamoxifen (Endoxifen) has a limit of quantitation less than or equal to 4 ng/mL. In some embodiments, the method of quantitation of N-Desmethyl-4-Hydroxy Tamoxifen (Endoxifen) has a limit of quantitation less than or equal to 3 ng/mL. In some embodiments, the method of quantitation of N-Desmethyl-4-Hydroxy Tamoxifen (Endoxifen) has a limit of quantitation less than or equal to 3 ng/mL. In some embodiments, the method of quantitation of N-Desmethyl-4-Hydroxy Tamoxifen (Endoxifen) has a limit of quantitation less than or equal to 2 ng/mL. In some embodiments, the method of quantitation of N-Desmethyl-4-Hydroxy Tamoxifen (Endoxifen) has a limit of quantitation less than or equal to 1.5 ng/mL. In some embodiments, the method of quantitation of N-Desmethyl-4-Hydroxy Tamoxifen (Endoxifen) has a limit of quantitation less than or equal to 1 ng/mL. In some embodiments, the method of quantitation of N-Desmethyl-4-Hydroxy Tamoxifen (Endoxifen) has a limit of quantitation less than or equal to 0.5 ng/mL. In some embodiments, the method of quantitation of N-Desmethyl-4-Hydroxy Tamoxifen (Endoxifen) has a limit of quantitation less than or equal to 0.4 ng/mL.

In some embodiments, the method of quantitation of N-Desmethyl-4'-Hydroxy Tamoxifen has a limit of quantitation less than or equal to 5 ng/mL. In some embodiments, the method of quantitation of N-Desmethyl-4'-Hydroxy Tamoxifen has a limit of quantitation less than or equal to 4 ng/mL. In some embodiments, the method of quantitation of N-Desmethyl-4'-Hydroxy Tamoxifen has a limit of quantitation less than or equal to 3 ng/mL. In some embodiments, the method of quantitation of N-Desmethyl-4'-Hydroxy Tamoxifen has a limit of quantitation less than or equal to 3 ng/mL. In some embodiments, the method of quantitation of N-Desmethyl-4'-Hydroxy Tamoxifen has a limit of quantitation less than or equal to 2 ng/mL. In some embodiments, the method of quantitation of N-Desmethyl-4'-Hydroxy Tamoxifen has a limit of quantitation less than or equal to 1.5 ng/mL. In some embodiments, the method of quantitation of N-Desmethyl-4'-Hydroxy Tamoxifen has a limit of quantitation less than or equal to 1 ng/mL. In some embodiments, the method of quantitation of N-Desmethyl-4'-Hydroxy Tamoxifen has a limit of quantitation less than or equal to 0.5 ng/mL. In some embodiments, the method of quantitation of N-Desmethyl-4'-Hydroxy Tamoxifen has a limit of quantitation less than or equal to 0.4 ng/mL.

In some embodiments, the method of quantitation of norendoxifen has a limit of quantitation less than or equal to 5 ng/mL. In some embodiments, the method of quantitation of norendoxifen has a limit of quantitation less than or equal to 4 ng/mL. In some embodiments, the method of quantitation of norendoxifen has a limit of quantitation less than or equal to 3 ng/mL. In some embodiments, the method of quantitation of norendoxifen has a limit of quantitation less than or equal to 3 ng/mL. In some embodiments, the method of quantitation of norendoxifen has a limit of quantitation less than or equal to 2 ng/mL. In some embodiments, the method of quantitation of norendoxifen has a limit of quantitation less than or equal to 1.5 ng/mL. In some embodiments, the method of quantitation of norendoxifen has a limit of quantitation less than or equal to 1.2 ng/mL. In some embodiments, the method of quantitation of norendoxifen has a limit of quantitation less than or equal to 1 ng/mL. In some embodiments, the method of quantitation of norendoxifen has a limit of quantitation less than or equal to 0.5 ng/mL.

In some embodiments, the method provided herein has sensitivity measured by limit of detection (LOD). In some embodiments, the method of detection of tamoxifen has a limit of detection less than or equal to 5 ng/mL. In some embodiments, the method of detection of tamoxifen has a limit of detection less than or equal to 4 ng/mL. In some embodiments, the method of detection of tamoxifen has a limit of detection less than or equal to 3 ng/mL. In some embodiments, the method of detection of tamoxifen has a limit of detection less than or equal to 3 ng/mL. In some embodiments, the method of detection of tamoxifen has a limit of detection less than or equal to 2 ng/mL. In some embodiments, the method of detection of tamoxifen has a limit of detection less than or equal to 1.5 ng/mL. In some embodiments, the method of detection of tamoxifen has a limit of detection less than or equal to 1 ng/mL. In some embodiments, the method of detection of tamoxifen has a limit of detection less than or equal to 0.6 ng/mL.

In some embodiments, the method of detection of N-Desmethyl Tamoxifen has a limit of detection less than or equal to 5 ng/mL. In some embodiments, the method of detection of N-Desmethyl Tamoxifen has a limit of detection less than or equal to 4 ng/mL. In some embodiments, the method of detection of N-Desmethyl Tamoxifen has a limit of detection less than or equal to 3 ng/mL. In some embodiments, the method of detection of N-Desmethyl Tamoxifen has a limit of detection less than or equal to 3 ng/mL. In some embodiments, the method of detection of N-Desmethyl Tamoxifen has a limit of detection less than or equal to 2 ng/mL. In some embodiments, the method of detection of N-Desmethyl Tamoxifen has a limit of detection less than or equal to 1.5 ng/mL. In some embodiments, the method of detection of N-Desmethyl Tamoxifen has a limit of detection less than or equal to 1 ng/mL. In some embodiments, the method of detection of N-Desmethyl Tamoxifen has a limit of detection less than or equal to 0.6 ng/mL.

In some embodiments, the method of detection of 4'-Hydroxy Tamoxifen has a limit of detection less than or equal to 5 ng/mL. In some embodiments, the method of detection of 4'-Hydroxy Tamoxifen has a limit of detection less than or equal to 4 ng/mL. In some embodiments, the method of detection of 4'-Hydroxy Tamoxifen has a limit of detection less than or equal to 3 ng/mL. In some embodiments, the method of detection of 4'-Hydroxy Tamoxifen has a limit of detection less than or equal to 3 ng/mL. In some embodiments, the method of detection of 4'-Hydroxy Tamoxifen has a limit of detection less than or equal to 2 ng/mL. In some embodiments, the method of detection of 4'-Hydroxy Tamoxifen has a limit of detection less than or equal to 1.5 ng/mL. In some embodiments, the method of detection of 4'-Hydroxy Tamoxifen has a limit of detection less than or equal to 1 ng/mL. In some embodiments, the method of detection of 4'-Hydroxy Tamoxifen has a limit of detection less than or equal to 0.5 ng/mL. In some embodiments, the method of detection of 4'-Hydroxy Tamoxifen has a limit of detection less than or equal to 0.4 ng/mL. In some embodiments, the method of detection of 4'-Hydroxy Tamoxifen has a limit of detection less than or equal to 0.2 ng/mL. In some embodiments, the method of detection of 4'-Hydroxy Tamoxifen has a limit of detection less than or equal to 0.1 ng/mL.

In some embodiments, the method of detection of 4-Hydroxy Tamoxifen has a limit of detection less than or equal to 5 ng/mL. In some embodiments, the method of detection of 4-Hydroxy Tamoxifen has a limit of detection less than or equal to 4 ng/mL. In some embodiments, the method of detection of 4-Hydroxy Tamoxifen has a limit of detection less than or equal to 3 ng/mL. In some embodiments, the method of detection of 4-Hydroxy Tamoxifen has a limit of detection less than or equal to 3 ng/mL. In some embodiments, the method of detection of 4-Hydroxy Tamoxifen has a limit of detection less than or equal to 2 ng/mL. In some embodiments, the method of detection of 4-Hydroxy Tamoxifen has a limit of detection less than or equal to 1.5 ng/mL. In some embodiments, the method of detection of 4-Hydroxy Tamoxifen has a limit of detection less than or equal to 1 ng/mL. In some embodiments, the method of detection of 4-Hydroxy Tamoxifen has a limit of detection less than or equal to 0.5 ng/mL. In some embodiments, the method of detection of 4-Hydroxy Tamoxifen has a limit of detection less than or equal to 0.4 ng/mL. In some embodiments, the method of detection of 4-Hydroxy Tamoxifen has a limit of detection less than or equal to 0.2 ng/mL. In some embodiments, the method of detection of 4-Hydroxy Tamoxifen has a limit of detection less than or equal to 0.1 ng/mL.

In some embodiments, the method of detection of N-Desmethyl-4-Hydroxy Tamoxifen (Endoxifen) has a limit of detection less than or equal to 5 ng/mL. In some embodiments, the method of detection of N-Desmethyl-4-Hydroxy Tamoxifen (Endoxifen) has a limit of detection less than or equal to 4 ng/mL. In some embodiments, the method of detection of N-Desmethyl-4-Hydroxy Tamoxifen (Endoxifen) has a limit of detection less than or equal to 3 ng/mL. In some embodiments, the method of detection of N-Desmethyl-4-Hydroxy Tamoxifen (Endoxifen) has a limit of detection less than or equal to 3 ng/mL. In some embodiments, the method of detection of N-Desmethyl-4-Hydroxy Tamoxifen (Endoxifen) has a limit of detection less than or equal to 2 ng/mL. In some embodiments, the method of detection of N-Desmethyl-4-Hydroxy Tamoxifen (Endoxifen) has a limit of detection less than or equal to 1.5 ng/mL. In some embodiments, the method of detection of N-Desmethyl-4-Hydroxy Tamoxifen (Endoxifen) has a limit of detection less than or equal to 1 ng/mL. In some embodiments, the method of detection of N-Desmethyl-4-Hydroxy Tamoxifen (Endoxifen) has a limit of detection less than or equal to 0.5 ng/mL. In some embodiments, the method of detection of N-Desmethyl-4-Hydroxy Tamoxifen (Endoxifen) has a limit of detection less than or equal to 0.4 ng/mL. In some embodiments, the method of detection of N-Desmethyl-4-Hydroxy Tamoxifen (Endoxifen) has a limit of detection less than or equal to 0.2 ng/mL. In some embodiments, the method of detection of N-Desmethyl-4-Hydroxy Tamoxifen (Endoxifen) has a limit of detection less than or equal to 0.15 ng/mL.

In some embodiments, the method of detection of N-Desmethyl-4'-Hydroxy Tamoxifen has a limit of detection less than or equal to 5 ng/mL. In some embodiments, the method of detection of N-Desmethyl-4'-Hydroxy Tamoxifen has a limit of detection less than or equal to 4 ng/mL. In some embodiments, the method of detection of N-Desmethyl-4'-Hydroxy Tamoxifen has a limit of detection less than or equal to 3 ng/mL. In some embodiments, the method of detection of N-Desmethyl-4'-Hydroxy Tamoxifen has a limit of detection less than or equal to 3 ng/mL. In some embodiments, the method of detection of N-Desmethyl-4'-Hydroxy Tamoxifen has a limit of detection less than or equal to 2 ng/mL. In some embodiments, the method of detection of N-Desmethyl-4'-Hydroxy Tamoxifen has a limit of detection less than or equal to 1.5 ng/mL. In some embodiments, the method of detection of N-Desmethyl-4'-Hydroxy Tamoxifen has a limit of detection less than or equal to 1 ng/mL. In some embodiments, the method of detection of N-Desmethyl-4'-Hydroxy Tamoxifen has a limit of detection less than or equal to 0.5 ng/mL. In some embodiments, the method of detection of N-Desmethyl-4'-Hydroxy Tamoxifen has a limit of detection less than or equal to 0.4 ng/mL.

In some embodiments, the method of detection of norendoxifen has a limit of detection less than or equal to 5 ng/mL. In some embodiments, the method of detection of norendoxifen has a limit of detection less than or equal to 4 ng/mL. In some embodiments, the method of detection of norendoxifen has a limit of detection less than or equal to 3 ng/mL. In some embodiments, the method of detection of norendoxifen has a limit of detection less than or equal to 3 ng/mL. In some embodiments, the method of detection of norendoxifen has a limit of detection less than or equal to 2 ng/mL. In some embodiments, the method of detection of norendoxifen has a limit of detection less than or equal to 1.5 ng/mL. In some embodiments, the method of detection of norendoxifen has a limit of detection less than or equal to 1.2 ng/mL. In some embodiments, the method of detection of norendoxifen has a limit of detection less than or equal to 1 ng/mL. In some embodiments, the method of detection of norendoxifen has a limit of detection less than or equal to 0.5 ng/mL.

As used herein, the term "purification" or "purifying" does not refer to removing all materials from the sample other than the analyte(s) of interest. Instead, purification refers to a procedure that enriches the amount of one or more analytes of interest relative to one or more other components of the sample. Purification, as used herein, does not require the isolation of an analyte from all others. In preferred embodiments, a purification step or procedure can be used to remove one or more interfering substances, e.g., one or more substances that would interfere with the operation of the instruments used in the methods or substances that may interfere with the detection of an analyte ion by mass spectrometry.

As used herein, the term "about" in reference to quantitative measurements, not including the measurement of mass of an ion, refers to the indicated value plus or minus 10%.

As used herein, the term "substantially all" refers to any proportion greater than 50%, more preferably greater than 60%, more preferably greater than 70%, more preferably greater than 80%, and more preferably greater than 90%.

As used herein, the term "sample" refers to any sample that may contain the analyte of interest. As used herein, the term "body fluid or tissue" means any fluid or tissue that can be isolated from the body of an individual. For example, "body fluid or tissue" may include blood, plasma, serum, bile, saliva, urine, tears, perspiration, and the like. If solid tissue is to be analyzed, it may be processed to release a liquid fraction that could contain any analyte present in the tissue. The liquid fraction can then be subject to the methods described herein.

As used herein, the term "size separation technique" means any technique (physical or chemical) that allows for the separation of at least one species from a test sample based on any one or more of molecular weight and shape. Examples of such techniques include, but are not limited to, filtration, chromatography, and certain aspects of mass spectrometry.

As used herein, the term "chromatography" refers to a process in which a chemical mixture carried by a liquid or gas is separated into components as a result of differential distribution of the chemical entities as they flow around, over, and/or through a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). "Liquid chromatography" includes reverse phase liquid chromatography (RPLC), high performance liquid chromatography (HPLC) and high turbulence liquid chromatography (HTLC).

As used herein, the term "high performance liquid chromatography" or "HPLC" refers to liquid chromatography in which the degree of separation is increased by forcing the mobile phase under pressure through a stationary phase, typically a densely packed column.

As used herein, the term "mass spectrometry" or "MS" refers to an analytical technique to identify compounds by their mass. MS refers to methods of filtering, detecting, and measuring ions based on their m/z. MS technology generally includes (1) ionizing the compounds to form charged species (e.g., ions); and (2) detecting the molecular weight of the ions and calculating their m/z. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 2:264-76 (1999); and Merchant and Weinberger, *Electrophoresis* 21:1164-67 (2000).

As used herein, the term "operating in positive ion mode" refers to those mass spectrometry methods where positive ions are detected. Similarly, the term "operating in negative ion mode" refers to those mass spectrometry methods where negative ions are detected.

As used herein, the term "ionization" or "ionizing" refers to the process of generating an analyte ion having a net electrical charge equal to one or more electron units. Positive ions are those having a net positive charge of one or more electron units. Negative ions are those having a net negative charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectroscopy methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "Atmospheric Pressure Photoionization" or "APPI" as used herein refers to the form of mass spectroscopy where the mechanism for the photoionization of molecule M is photon absorption and electron ejection to form the molecular M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. Robb, D. B., Covey, T. R. and Bruins, A. P. (2000): See, e.g., Robb et al., Atmospheric pressure photoionization: An ionization method for liquid chromatography-mass spectrometry. *Anal. Chem.* 72(15): 3653-3659.

As used herein, the term "inductively coupled plasma" or "ICP" refers to methods in which a sample is interacted with a partially ionized gas at a sufficiently high temperature to atomize and ionize most elements As used, herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase.

As used herein, the term "limit of quantification" or "LOQ" refers to the point where measurements become quantitatively meaningful. The analyte response at this LOQ is identifiable, discrete and reproducible with a precision of 20% and an accuracy of 80% to 120%.

In certain preferred embodiments of the methods disclosed herein, mass spectrometry is performed in positive ion mode. In certain particularly preferred embodiments of the methods disclosed herein, mass spectrometry is performed using ESI.

In other preferred embodiments, a separately detectable internal standard is provided in the sample.

In one embodiment, the methods involve the combination of LC with mass spectrometry. In another preferred embodiment, the mass spectrometry is tandem mass spectrometry (MS/MS).

The summary of the invention described above is non-limiting and other features and advantages of the invention will be apparent from the following detailed description of the invention, and from the claims.

DETAILED DESCRIPTION OF THE INVENTION

Methods are described for quantitatively measuring tamoxifen and/or metabolites thereof in a patient sample. This quantitative measurement is achieved through the use of LC-MS/MS techniques. Prior to the use of LC-MS/MS, samples may be prepared by the following technique, or any portion thereof. A first purification of tamoxifen and/or metabolites thereof in a sample may be conducted through the use of a protein purification, filtration, or chromatography.

Any suitable size separation technique may be utilized, but in the examples that follow, both the first and second size separation techniques are filtration through a molecular weight cut-off filter. It is also possible, as discussed in the Examples that follow, to select a molecular weight cut-off filter with an appropriate molecular weight cut-off such that the same filter can be used for both the first size separation and the second size separation.

LC, most preferably HPLC, is utilized, may be utilized either alone or in combination with other purification methods, to purify selected analytes. This purification is combined with MS/MS, thereby providing an assay system for quantifying selected analytes in a test sample. The quantity of the selected analytes in the sample is then used to determine the quantity of tamoxifen in the original test sample. The quantitation methods provided herein have enhanced specificity and are less subject to methodological problems (such as antibody interference).

Suitable samples may include any test sample that may contain the analyte of interest. In some preferred embodiments, a sample is a biological sample; that is, a sample obtained from any biological source, such as an animal, a cell culture, an organ culture, and the like. In certain preferred embodiments, samples are obtained from a mammalian animal, such as a dog, cat, horse, etc. Particularly preferred mammalian animals are primates, most preferably humans. Particularly preferred samples include blood, plasma, serum, urine, saliva, tears, cerebrospinal fluid, or other body fluid or tissue samples. Such samples may be obtained, for example, from a patient; that is, a living person presenting oneself in a clinical setting for diagnosis, prognosis, or treatment of a disease or condition. The test sample is preferably obtained from a patient, for example, serum or plasma.

Sample Preparation for Mass Spectrometry

Samples may be processed or purified to obtain preparations that are suitable for analysis by mass spectrometry. Such purification will usually include chromatography, such as liquid chromatography, and may also often involve an additional purification procedure that is performed prior to chromatography. Various procedures may be used for this purpose depending on the type of sample or the type of chromatography. Examples include filtration, centrifugation, combinations thereof and the like.

Filtration is one preferred method of preparing a test sample, especially a biological test sample, such as serum or plasma, for chromatography. Such filtration is carried out by filtering a test sample through a molecular weight cut-off filter to separate species with molecular weights higher than the filter's cut-off from those with molecular weights lower than the filter's cut-off. The test sample remaining above the filter following complete (or near complete) filtration is substantially free of potentially interfering species with molecular weights lower than the filter's cut-off.

Various methods have been described involving the use of HPLC for sample clean-up prior to mass spectrometry analysis. See, e.g., Taylor et al., *Therapeutic Drug Monitoring* 22:608-12 (2000) (manual precipitation of blood samples, followed by manual C18 solid phase extraction, injection into an HPLC for chromatography on a C18 analytical column, and MS/MS analysis); and Salm et al., *Clin. Therapeutics* 22 Supl. B:B71-B85 (2000) (manual precipitation of blood samples, followed by manual C18 solid phase extraction, injection into an HPLC for chromatography on a C18 analytical column, and MS/MS analysis). One of skill in the art may select HPLC instruments and columns that are suitable for use in the methods. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties. One suitable bonded surface is a hydrophobic bonded surface such as an alkyl bonded surface. Alkyl bonded surfaces may include C-4, C-8, or C-18 bonded alkyl groups, preferably C-8 bonded groups. The chromatographic column includes an inlet port for receiving a sample and an outlet port for discharging an effluent that includes the fractionated sample.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In one embodiment, the sample to be analyzed is applied to the column at the inlet port, eluted with a solvent or solvent mixture, and discharged at the outlet port. Different solvent modes may be selected for eluting the analytes of interest. For example, liquid chromatography may be performed using a gradient mode, an isocratic mode, or a polytyptic (i.e. mixed) mode. In preferred embodiments, HPLC is performed on an analytical HPLC system with a C8 solid phase using 0.2% formic acid in HPLC Grade Ultra Pure Water and 0.2% formic acid in 100% methanol as the mobile phases.

Numerous column packings are available for chromatographic separation of samples and selection of an appropriate separation protocol is an empirical process that depends on the sample characteristics, analyte of interest, presence of interfering substances and their characteristics, etc. Commercially available HPLC columns include, but are not limited to, polar, ion exchange (both cation and anion), hydrophobic interaction, phenyl, C-2, C-8, C-18, and polar coating on porous polymer columns.

In one embodiment, the HPLC column has a C8 solid phase with a median particle size of 5 µm (nominal) and a median particle pore size of 100 Å. In a preferred embodiment the column dimensions are 1.0 mm ID×50 mm length (Phenomenex Corp. Luna 5µ C8(2) 100 Å New Column 50×1.0 mm, Phenomenex Cat. No. 00B-4249-AO or equivalent).

During chromatography, the separation of materials is effected by variables such as choice of eluent (also known as a "mobile phase"), choice of gradient elution and the gradient conditions, temperature, etc.

Detection and Quantitation by Mass Spectrometry

In various embodiments, analytes may be ionized by any method known to the skilled artisan. Mass spectrometry is performed using a mass spectrometer, which includes an ion source for ionizing the fractionated sample and creating charged molecules for further analysis. Ionization sources used in various MS techniques include, but are not limited to, electron ionization, chemical ionization, electrospray ionization (ESI), photon ionization, atmospheric pressure chemical ionization (APCI), photoionization, atmospheric pressure photoionization (APPI), fast atom bombardment (FAB)/liquid secondary ionization (LSIMS), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

In preferred embodiments, analytes are ionized by electrospray ionization (ESI) creating analyte precursor ions. In related preferred embodiments, analyte precursor ions are in a gaseous state and the inert collision gas is argon.

After the sample has been ionized, the positively charged ions thereby created may be analyzed to determine m/z. Suitable analyzers for determining m/z include quadrupole analyzers, ion trap analyzers, and time-of-flight analyzers. The ions may be detected using one of several detection modes. For example, only selected ions may be detected using a selective ion monitoring mode (SIM), or alternatively, multiple ions may be detected using a scanning mode, e.g., multiple reaction monitoring (MRM) or selected reaction monitoring (SRM). In preferred embodiments, ions are detected using SRM.

Preferably, m/z is determined using a quadrupole instrument. In a "quadrupole" or "quadrupole ion trap" instrument, ions in an oscillating radio frequency field experience a force proportional to the DC potential applied between electrodes, the amplitude of the RF signal, and m/z. The voltage and amplitude may be selected so that only ions having a particular m/z travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS." In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collision with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

Additionally, recent advances in technology, such as matrix-assisted laser desorption ionization coupled with time-of-flight analyzers ("MALDI-TOF") permit the analysis of analytes at femtomole levels in very short ion pulses. Mass spectrometers that combine time-of-flight analyzers with tandem MS are also well known to the artisan. Additionally, multiple mass spectrometry steps may be combined in methods known as "MS/MS". Various other combinations may be employed, such as MS/MS/TOF, MALDI/MS/MS/TOF, or SELDI/MS/MS/TOF mass spectrometry.

The mass spectrometer typically provides the user with an ion scan; that is, the relative abundance of each ion with a particular m/z over a given range (e.g., 400 to 1600 amu). The results of an analyte assay, that is, a mass spectrum, may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, molecular standards may be run with the samples and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of tamoxifen. Methods of generating and using such standard curves are well known in the art and one of ordinary skill is capable of selecting an appropriate internal standard. Numerous other methods for relating the amount of an ion to the amount of the original molecule will be well known to those of ordinary skill in the art.

One or more steps of the methods may be performed using automated machines. In certain embodiments, one or more purification steps are performed on-line, and more preferably all of the LC purification and mass spectrometry steps may be performed in an on-line fashion.

In certain embodiments, techniques such as MS/MS are used to isolate precursor ions for further fragmentation. In these embodiments, collision activation dissociation (CAD) may be used to generate the fragment ions for further detection. In CAD, precursor ions gain energy through collisions with an inert gas, and subsequently fragment by a process referred to as "unimolecular decomposition". Sufficient energy must be deposited in the precursor ion so that certain bonds within the ion can be broken due to increased vibrational energy. In alternative embodiments, electron transfer dissociation (ETD) may be used to generate the fragment ions. In ETD, radical anions are used to transfer electrons to multiply charged peptide or protein cations resulting in random cleavage along the peptide backbone.

In particularly preferred embodiments, analyte is detected and/or quantified using LC-MS/MS as follows. An analyte enriched sample prepared as described above is subjected to LC. The flow of liquid solvent from the chromatographic column enters the heated nebulizer interface of a LC-MS/MS analyzer and the solvent/analyte mixture is converted to vapor in the heated tubing of the interface. The analyte contained in the nebulized solvent, is ionized by the corona discharge needle of the interface, which applies a large voltage to the nebulized solvent/analyte mixture. The ions pass through the orifice of the instrument and enter the first quadrupole. Quadrupoles 1 and 3 (Q1 and Q3) are mass filters, allowing selection of ions (i.e., "precursor" and "fragment" ions) based on their m/z. Quadrupole 2 (Q2) is the collision cell, where ions are fragmented. Q1 selects for ions with m/z of precursor ions. Selected precursor ions are allowed to pass into the collision chamber (Q2), while ions with any other m/z collide with the sides of Q1 and are eliminated. Precursor ions entering Q2 may be fragmented with collision activated dissociation (CAD) through collisions with neutral argon gas molecules. Alternatively, if the precursor ions entering Q2 are multiply charged cations, they may be fragmented with electron transfer dissociation (ETD). The fragment ions generated are passed into Q3, where selected fragment ions are collected while other ions are eliminated.

Using standard methods well known in the art, one of ordinary skill is capable of identifying one or more fragment ions of a particular precursor ion that may be used for selection in Q3. A specific fragment ion is one that will not be formed in significant amounts by other molecules with similar molecular structures. In contrast, a non-specific fragment ion is one that is formed by molecules other than the desired analyte. Suitable specific fragment ions can be identified by testing various molecular standards to determine whether fragment ions formed by a selected analyte are also formed by other molecules with similar structures or features. Preferably, at least one fragment ion specific for ions with m/z corresponding to that of analyte ions are identified.

As ions collide with the detector they produce a pulse of electrons that are converted to a digital signal. The acquired data is relayed to a computer, which plots ion counts per unit time. The areas under the peaks corresponding to particular ions, or the amplitude of such peaks, are measured and the area or amplitude is correlated to the amount of the analyte of interest. In certain embodiments, the area under the curves, or amplitude of the peaks, for fragment ion(s) and/or precursor ions are measured to determine the amount of analytes with m/z. As described above, the relative abundance of a given ion may be converted into an absolute amount of the original analyte using calibration standard curves based on peaks of one or more ions of an internal molecular standard. The absolute amount of an analyte detected by LC-MS/MS can then be converted into an absolute amount of analyte that was present in the original test sample.

In some embodiments, the method provided herein has sensitivity measured by limit of quantitation (LOQ). In some embodiments, the method of quantitation of tamoxifen has a limit of quantitation less than or equal to 5 ng/mL. In some embodiments, the method of quantitation of tamoxifen has a limit of quantitation less than or equal to 4 ng/mL. In some embodiments, the method of quantitation of tamoxifen has a limit of quantitation less than or equal to 3 ng/mL. In some embodiments, the method of quantitation of tamoxifen has a limit of quantitation less than or equal to 3 ng/mL. In some embodiments, the method of quantitation of tamoxifen has a limit of quantitation less than or equal to 2 ng/mL. In some embodiments, the method of quantitation of tamoxifen has a limit of quantitation less than or equal to 1.5 ng/mL.

In some embodiments, the method of quantitation of N-Desmethyl Tamoxifen has a limit of quantitation less than or equal to 5 ng/mL. In some embodiments, the method of quantitation of N-Desmethyl Tamoxifen has a limit of quantitation less than or equal to 4 ng/mL. In some embodiments, the method of quantitation of N-Desmethyl Tamoxifen has a limit of quantitation less than or equal to 3 ng/mL. In some embodiments, the method of quantitation of N-Desmethyl Tamoxifen has a limit of quantitation less than or equal to 3 ng/mL. In some embodiments, the method of quantitation of N-Desmethyl Tamoxifen has a limit of quantitation less than or equal to 2 ng/mL. In some embodiments, the method of quantitation of N-Desmethyl Tamoxifen has a limit of quantitation less than or equal to 1.5 ng/mL.

In some embodiments, the method of quantitation of 4'-Hydroxy Tamoxifen has a limit of quantitation less than or equal to 5 ng/mL. In some embodiments, the method of quantitation of 4'-Hydroxy Tamoxifen has a limit of quantitation less than or equal to 4 ng/mL. In some embodiments, the method of quantitation of 4'-Hydroxy Tamoxifen has a limit of quantitation less than or equal to 3 ng/mL. In some embodiments, the method of quantitation of 4'-Hydroxy Tamoxifen has a limit of quantitation less than or equal to 3 ng/mL. In some embodiments, the method of quantitation of 4'-Hydroxy Tamoxifen has a limit of quantitation less than or equal to 2 ng/mL. In some embodiments, the method of quantitation of 4'-Hydroxy Tamoxifen has a limit of quantitation less than or equal to 1.5 ng/mL. In some embodiments, the method of quantitation of 4'-Hydroxy Tamoxifen has a limit of quantitation less than or equal to 1 ng/mL. In some embodiments, the method of quantitation of 4'-Hydroxy Tamoxifen has a limit of quantitation less than or equal to 0.5 ng/mL. In some embodiments, the method of quantitation of 4'-Hydroxy Tamoxifen has a limit of quantitation less than or equal to 0.4 ng/mL. In some embodiments, the method of quantitation of 4'-Hydroxy Tamoxifen has a limit of quantitation less than or equal to 0.2 ng/mL.

In some embodiments, the method of quantitation of 4-Hydroxy Tamoxifen has a limit of quantitation less than or equal to 5 ng/mL. In some embodiments, the method of quantitation of 4-Hydroxy Tamoxifen has a limit of quantitation less than or equal to 4 ng/mL. In some embodiments, the method of quantitation of 4-Hydroxy Tamoxifen has a limit of quantitation less than or equal to 3 ng/mL. In some embodiments, the method of quantitation of 4-Hydroxy Tamoxifen has a limit of quantitation less than or equal to 3 ng/mL. In some embodiments, the method of quantitation of 4-Hydroxy Tamoxifen has a limit of quantitation less than or equal to 2 ng/mL. In some embodiments, the method of quantitation of 4-Hydroxy Tamoxifen has a limit of quantitation less than or equal to 1.5 ng/mL. In some embodiments, the method of quantitation of 4-Hydroxy Tamoxifen has a limit of quantitation less than or equal to 1 ng/mL. In some embodiments, the method of quantitation of 4-Hydroxy Tamoxifen has a limit of quantitation less than or equal to 0.5 ng/mL. In some embodiments, the method of quantitation of 4-Hydroxy Tamoxifen has a limit of quantitation less than or equal to 0.4 ng/mL. In some embodiments, the method of quantitation of 4-Hydroxy Tamoxifen has a limit of quantitation less than or equal to 0.2 ng/mL.

In some embodiments, the method of quantitation of N-Desmethyl-4-Hydroxy Tamoxifen (Endoxifen) has a limit of quantitation less than or equal to 5 ng/mL. In some embodiments, the method of quantitation of N-Desmethyl-4-Hydroxy Tamoxifen (Endoxifen) has a limit of quantitation less than or equal to 4 ng/mL. In some embodiments, the method of quantitation of N-Desmethyl-4-Hydroxy Tamoxifen (Endoxifen) has a limit of quantitation less than or equal to 3 ng/mL. In some embodiments, the method of quantitation of N-Desmethyl-4-Hydroxy Tamoxifen (Endoxifen) has a limit of quantitation less than or equal to 3 ng/mL. In some embodiments, the method of quantitation of N-Desmethyl-4-Hydroxy Tamoxifen (Endoxifen) has a limit of quantitation less than or equal to 2 ng/mL. In some embodiments, the method of quantitation of N-Desmethyl-4-Hydroxy Tamoxifen (Endoxifen) has a limit of quantitation less than or equal to 1.5 ng/mL. In some embodiments, the method of quantitation of N-Desmethyl-4-Hydroxy Tamoxifen (Endoxifen) has a limit of quantitation less than or equal to 1 ng/mL. In some embodiments, the method of quantitation of N-Desmethyl-4-Hydroxy Tamoxifen (Endoxifen) has a limit of quantitation less than or equal to 0.5 ng/mL. In some embodiments, the method of quantitation of N-Desmethyl-4-Hydroxy Tamoxifen (Endoxifen) has a limit of quantitation less than or equal to 0.4 ng/mL.

In some embodiments, the method of quantitation of N-Desmethyl-4'-Hydroxy Tamoxifen has a limit of quantitation less than or equal to 5 ng/mL. In some embodiments, the method of quantitation of N-Desmethyl-4'-Hydroxy Tamoxifen has a limit of quantitation less than or equal to 4 ng/mL. In some embodiments, the method of quantitation of N-Desmethyl-4'-Hydroxy Tamoxifen has a limit of quantitation less than or equal to 3 ng/mL. In some embodiments, the method of quantitation of N-Desmethyl-4'-Hydroxy Tamoxifen has a limit of quantitation less than or equal to 3 ng/mL. In some embodiments, the method of quantitation of N-Desmethyl-4'-Hydroxy Tamoxifen has a limit of quantitation less than or equal to 2 ng/mL. In some embodiments, the method of quantitation of N-Desmethyl-4'-Hydroxy Tamoxifen has a limit of quantitation less than or equal to 1.5 ng/mL. In some embodiments, the method of quantitation of N-Desmethyl-4'-Hydroxy Tamoxifen has a limit of quantitation less than or equal to 1 ng/mL. In some embodiments, the method of quantitation of N-Desmethyl-4'-Hydroxy Tamoxifen has a limit of quantitation less than or equal to 0.5 ng/mL. In some embodiments, the method of quantitation of N-Desmethyl-4'-Hydroxy Tamoxifen has a limit of quantitation less than or equal to 0.4 ng/mL.

In some embodiments, the method of quantitation of norendoxifen has a limit of quantitation less than or equal to 5 ng/mL. In some embodiments, the method of quantitation of norendoxifen has a limit of quantitation less than or equal to 4 ng/mL. In some embodiments, the method of quantitation of norendoxifen has a limit of quantitation less than or equal to 3 ng/mL. In some embodiments, the method of quantitation of norendoxifen has a limit of quantitation less than or equal to 3 ng/mL. In some embodiments, the method of quantitation of norendoxifen has a limit of quantitation less than or equal to 2 ng/mL. In some embodiments, the method of quantitation of norendoxifen has a limit of quantitation less than or equal to 1.5 ng/mL. In some embodiments, the method of quantitation of norendoxifen has a limit of quantitation less than or equal to 1.2 ng/mL. In some embodiments, the method of quantitation of norendoxifen has a limit of quantitation less than or equal to 1 ng/mL. In some embodiments, the method of quantitation of norendoxifen has a limit of quantitation less than or equal to 0.5 ng/mL.

In some embodiments, the method provided herein has sensitivity measured by limit of detection (LOD). In some embodiments, the method of detection of tamoxifen has a limit of detection less than or equal to 5 ng/mL. In some embodiments, the method of detection of tamoxifen has a limit of detection less than or equal to 4 ng/mL. In some embodiments, the method of detection of tamoxifen has a limit of detection less than or equal to 3 ng/mL. In some embodiments, the method of detection of tamoxifen has a limit of detection less than or equal to 3 ng/mL. In some embodiments, the method of detection of tamoxifen has a limit of detection less than or equal to 2 ng/mL. In some embodiments, the method of detection of tamoxifen has a limit of detection less than or equal to 1.5 ng/mL. In some embodiments, the method of detection of tamoxifen has a limit of detection less than or equal to 1 ng/mL. In some embodiments, the method of detection of tamoxifen has a limit of detection less than or equal to 0.6 ng/mL.

In some embodiments, the method of detection of N-Desmethyl Tamoxifen has a limit of detection less than or equal to 5 ng/mL. In some embodiments, the method of detection of N-Desmethyl Tamoxifen has a limit of detection less than or equal to 4 ng/mL. In some embodiments, the method of detection of N-Desmethyl Tamoxifen has a limit of detection less than or equal to 3 ng/mL. In some embodiments, the method of detection of N-Desmethyl Tamoxifen has a limit of detection less than or equal to 3 ng/mL. In some embodiments, the method of detection of N-Desmethyl Tamoxifen has a limit of detection less than or equal to 2 ng/mL. In some embodiments, the method of detection of N-Desmethyl Tamoxifen has a limit of detection less than or equal to 1.5 ng/mL. In some embodiments, the method of detection of N-Desmethyl Tamoxifen has a limit of detection less than or equal to 1 ng/mL. In some embodiments, the method of detection of N-Desmethyl Tamoxifen has a limit of detection less than or equal to 0.6 ng/mL.

In some embodiments, the method of detection of 4'-Hydroxy Tamoxifen has a limit of detection less than or equal to 5 ng/mL. In some embodiments, the method of detection of 4'-Hydroxy Tamoxifen has a limit of detection less than or equal to 4 ng/mL. In some embodiments, the method of detection of 4'-Hydroxy Tamoxifen has a limit of detection less than or equal to 3 ng/mL. In some embodiments, the method of detection of 4'-Hydroxy Tamoxifen has a limit of detection less than or equal to 3 ng/mL. In some embodiments, the method of detection of 4'-Hydroxy Tamoxifen has a limit of detection less than or equal to 2 ng/mL. In some embodiments, the method of detection of 4'-Hydroxy Tamoxifen has a limit of detection less than or equal to 1.5 ng/mL. In some embodiments, the method of detection of 4'-Hydroxy Tamoxifen has a limit of detection less than or equal to 1 ng/mL. In some embodiments, the method of detection of 4'-Hydroxy Tamoxifen has a limit of detection less than or equal to 0.5 ng/mL. In some embodiments, the method of detection of 4'-Hydroxy Tamoxifen has a limit of detection less than or equal to 0.4 ng/mL. In some embodiments, the method of detection of 4'-Hydroxy Tamoxifen has a limit of detection less than or equal to 0.2 ng/mL. In some embodiments, the method of detection of 4'-Hydroxy Tamoxifen has a limit of detection less than or equal to 0.1 ng/mL.

In some embodiments, the method of detection of 4-Hydroxy Tamoxifen has a limit of detection less than or equal to 5 ng/mL. In some embodiments, the method of detection of 4-Hydroxy Tamoxifen has a limit of detection less than or equal to 4 ng/mL. In some embodiments, the method of detection of 4-Hydroxy Tamoxifen has a limit of detection less than or equal to 3 ng/mL. In some embodiments, the method of detection of 4-Hydroxy Tamoxifen has a limit of detection less than or equal to 3 ng/mL. In some embodiments, the method of detection of 4-Hydroxy Tamoxifen has a limit of detection less than or equal to 2 ng/mL. In some embodiments, the method of detection of 4-Hydroxy Tamoxifen has a limit of detection less than or equal to 1.5 ng/mL. In some embodiments, the method of detection of 4-Hydroxy Tamoxifen has a limit of detection less than or equal to 1 ng/mL. In some embodiments, the method of detection of 4-Hydroxy Tamoxifen has a limit of detection less than or equal to 0.5 ng/mL. In some embodiments, the method of detection of 4-Hydroxy Tamoxifen has a limit of detection less than or equal to 0.4 ng/mL. In some embodiments, the method of detection of 4-Hydroxy Tamoxifen has a limit of detection less than or equal to 0.2 ng/mL. In some embodiments, the method of detection of 4-Hydroxy Tamoxifen has a limit of detection less than or equal to 0.1 ng/mL.

In some embodiments, the method of detection of N-Desmethyl-4-Hydroxy Tamoxifen (Endoxifen) has a limit of detection less than or equal to 5 ng/mL. In some embodiments, the method of detection of N-Desmethyl-4-Hydroxy Tamoxifen (Endoxifen) has a limit of detection less than or equal to 4 ng/mL. In some embodiments, the method of detection of N-Desmethyl-4-Hydroxy Tamoxifen (Endoxifen) has a limit of detection less than or equal to 3 ng/mL. In some embodiments, the method of detection of N-Desmethyl-4-Hydroxy Tamoxifen (Endoxifen) has a limit of detection less than or equal to 3 ng/mL. In some embodiments, the method of detection of N-Desmethyl-4-Hydroxy Tamoxifen (Endoxifen) has a limit of detection less than or equal to 2 ng/mL. In some embodiments, the method of detection of N-Desmethyl-4-Hydroxy Tamoxifen (Endoxifen) has a limit of detection less than or equal to 1.5 ng/mL. In some embodiments, the method of detection of N-Desmethyl-4-Hydroxy Tamoxifen (Endoxifen) has a limit of detection less than or equal to 1 ng/mL. In some embodiments, the method of detection of N-Desmethyl-4-Hydroxy Tamoxifen (Endoxifen) has a limit of detection less than or equal to 0.5 ng/mL. In some embodiments, the method of detection of N-Desmethyl-4-Hydroxy Tamoxifen (Endoxifen) has a limit of detection less than or equal to 0.4 ng/mL. In some embodiments, the method of detection of N-Desmethyl-4-Hydroxy Tamoxifen (Endoxifen) has a limit of detection less than or equal to 0.2 ng/mL. In some embodiments, the method of detection of N-Desmethyl-4-Hydroxy Tamoxifen (Endoxifen) has a limit of detection less than or equal to 0.15 ng/mL.

In some embodiments, the method of detection of N-Desmethyl-4'-Hydroxy Tamoxifen has a limit of detection less than or equal to 5 ng/mL. In some embodiments, the method of detection of N-Desmethyl-4'-Hydroxy Tamoxifen has a limit of detection less than or equal to 4 ng/mL. In some embodiments, the method of detection of N-Desmethyl-4'-Hydroxy Tamoxifen has a limit of detection less than or equal to 3 ng/mL. In some embodiments, the method of detection of N-Desmethyl-4'-Hydroxy Tamoxifen has a limit of detection less than or equal to 3 ng/mL. In some embodiments, the method of detection of N-Desmethyl-4'-Hydroxy Tamoxifen has a limit of detection less than or equal to 2 ng/mL. In some embodiments, the method of detection of N-Desmethyl-4'-Hydroxy Tamoxifen has a limit of detection less than or equal to 1.5 ng/mL. In some embodiments, the method of detection of N-Desmethyl-4'-Hydroxy Tamoxifen has a limit of detection less than or equal to 1 ng/mL. In some embodiments, the method of detection of N-Desmethyl-4'-Hydroxy Tamoxifen has a limit of detection less than or equal to 0.5 ng/mL. In some embodiments, the method of detection of N-Desmethyl-4'-Hydroxy Tamoxifen has a limit of detection less than or equal to 0.4 ng/mL.

In some embodiments, the method of detection of norendoxifen has a limit of detection less than or equal to 5 ng/mL. In some embodiments, the method of detection of norendoxifen has a limit of detection less than or equal to 4 ng/mL. In some embodiments, the method of detection of norendoxifen has a limit of detection less than or equal to 3 ng/mL. In some embodiments, the method of detection of norendoxifen has a limit of detection less than or equal to 3 ng/mL. In some embodiments, the method of detection of norendoxifen has a limit of detection less than or equal to 2 ng/mL. In some embodiments, the method of detection of norendoxifen has a limit of detection less than or equal to 1.5 ng/mL. In some embodiments, the method of detection of norendoxifen has a limit of detection less than or equal to 1.2 ng/mL. In some embodiments, the method of detection of norendoxifen has a limit of detection less than or equal to 1 ng/mL. In some embodiments, the method of detection of norendoxifen has a limit of detection less than or equal to 0.5 ng/mL.

The following examples serve to illustrate the invention. These examples are in no way intended to limit the scope of the methods.

EXAMPLES

Example 1: Determination of Tamoxifen and its Metabolites

In the following procedure, tamoxifen and its metabolites are extracted from serum. The serum is added to a filter plate, and then mixed with acetonitrile/IS, which then forms a precipitate. The mixture is then placed on a positive pressure manifold, and the organic fraction is passed through to a collection plate. The plate is lidded, and then placed on the Cohesive system for injection onto MS/MS. The MS is in APCI-positive mode. The quantitation is based upon unique parent-product transitions. Those analytes with similar transitions were separated chromatographically.

Patient Preparation

| Component | Special Notations |
|---|---|
| Fasting/Special Diets | N/A |
| Specimen Collection and/or Timing | N/A |
| Special Collection Procedures | N/A |
| Other | No aromatase inhibitors. |

Specimen Type & Handling

| | Criteria |
|---|---|
| Type | |
| Preferred | Serum |
| Other Acceptable | |
| Collection Container | Red top (no gel) |
| Volume | |
| Optimum | 0.5 mL-Optimum |
| Minimum | 0.3 mL-Minimum |
| Transport Container & Temperature | Frozen |
| Stability & Storage Requirements | Room Temperature: 5 Days Refrigerated: 7 Days Frozen: 31 Days |
| Timing Considerations | |
| Unacceptable Specimens & Actions to Take | Plasma Samples Samples in SST tubes Hemolyzed samples not acceptable. |
| Compromising Physical Characteristics | |
| Other Considerations | |

Reagent Summary

| Reagents | Supplier & Catalog Number | Quantity |
|---|---|---|
| Ammonium Formate | Sigma, 17843-250G or verified equivalent | 250 Grams |
| Formic Acid | Sigma, F0507-100 mL or verified equivalent | 100 mL |
| Ethanol, Absolute, Anhydrous, 200 Proof | Pharmco-AAPER, Cat #111000200 or verified equivalent | 1 pint |
| Acetonitrile, HPLC Grade | B&J, Cat #015-4 or verified equivalent | 4 Liters |
| Biocell Serum, Human Serum, Stripped and Delipidized (Opticlear) | Biocell Labs, Cat #1121-00 or verified equivalent | 4 Liter |
| Tamoxifen | Toronto Research Labs (TRC), Cat #T006000 or verified equivalent | 25 Grams |
| N-Desmethyl Tamoxifen HCl | Toronto Research Labs (TRC), Cat #D293900 or verified equivalent | 50 mg |

-continued

| Reagents | Supplier & Catalog Number | Quantity |
|---|---|---|
| N-Desmethyl-4-Hydroxy Tamoxifen | Toronto Research Labs (TRC), Cat #D292043 or verified equivalent | 50 mg |
| N-Desmethyl-4'-Hydroxy Tamoxifen | Toronto Research Labs (TRC), Cat #D292041 or verified equivalent | 10 mg |
| (Z)-4-Hydroxy Tamoxifen | Toronto Research Labs (TRC), Cat #H954725 or verified equivalent | 100 mg |
| 4'-Hydroxy Tamoxifen | Toronto Research Labs (TRC), Cat #H954730 or verified equivalent | 25 mg |
| (E/Z)-Tamoxifen-d5 | Toronto Research Labs (TRC), Cat #T006007 or verified equivalent | 10 mg |
| N-Desmethyl Tamoxifen-d5 | Toronto Research Labs (TRC), Cat #D293902 or verified equivalent | 10 mg |
| N-Desmethyl-4-Hydroxy Tamoxifen-d5 | Toronto Research Labs (TRC), Cat #D292044 or verified equivalent | 10 mg |
| N-Desmethyl-4'-Hydroxy Tamoxifen-d3 | Toronto Research Labs (TRC), Cat #D291867 or verified equivalent | 10 mg |
| (Z)-4-Hydroxy Tamoxifen-d5 | Toronto Research Labs (TRC), Cat #H954757 or verified equivalent | 25 mg |
| 4'-Hydroxy Tamoxifen-d6 | Toronto Research Labs (TRC), Cat #H954757 or verified equivalent | 10 mg |

Calibrators/Standards Used

A 12-point calibration is used for each analyte. Initially, only one standard is made (Std-12), with a series of dilutions performed to generate the remaining standards. The standard (#12) is to be removed from the −70° C. freezer and thawed. While thawing, label twelve 12×75 mm tubes.

Add 3.0 mL of std-12 to tube 12. From this standard, you will follow the table below to create the standard curve. A standard curve is to be generated with each assay. Place the initial standard back in the −60 to −90° C. freezer.

| Analyte | Target Concentration (ng/mL) | Volume to add (1 mg/mL) |
|---|---|---|
| Tamoxifen | 1,250 | 250 uL |
| N-Desmethyl Tamoxifen | 1,250 | 250 uL |
| N-Desmethyl-4-Hydroxy Tamoxifen (Endoxifen) | 300 | 60 uL |
| N-Desmethyl-4'-Hydroxy Tamoxifen | 300 | 60 uL |
| 4-Hydroxy Tamoxifen | 200 | 40 uL |
| 4'-Hydroxy Tamoxifen | 200 | 40 uL |

Once these analytes have been added, QS to 200 mL with Biocell serum. Mix, then aliquot into 15 mL centrifuge tubes. Label (Std-12), then place the tubes in the −60° C. to −90° C. freezer for storage. Stable for 1 year.

Standard Target Concentrations

| Std # | Target Concentration (Tamoxifen) | Target Concentration (N-Desmethyl Tamoxifen)) | Target Concentration (Endoxifen) | Target Concentration (N-Desmethyl-4'-Hydroxy tamoxifen) |
|---|---|---|---|---|
| 12 | 1250 | 1250 | 300 | 300 |
| 11 | 1000 | 1000 | 240 | 240 |
| 10 | 750 | 750 | 180 | 180 |
| 9 | 500 | 500 | 120 | 120 |
| 8 | 400 | 400 | 96 | 96 |
| 7 | 250 | 250 | 60 | 60 |
| 6 | 100 | 100 | 24 | 24 |
| 5 | 50 | 50 | 9 | 9 |
| 4 | 25 | 25 | 6 | 6 |
| 3 | 10 | 10 | 1.8 | 1.8 |
| 2 | 5 | 5 | 0.9 | 0.9 |
| 1 | 2.5 | 2.5 | 0.45 | 0.45 |

| Std # | Target Concentration (4-Hydroxy Tamoxifen) | Target Concentration (4'-Hydroxy Tamoxifen) |
|---|---|---|
| 12 | 200 | 200 |
| 11 | 160 | 160 |
| 10 | 120 | 120 |
| 9 | 80 | 80 |
| 8 | 64 | 64 |
| 7 | 40 | 40 |
| 6 | 16 | 16 |
| 5 | 6 | 6 |
| 4 | 4 | 4 |
| 3 | 1.2 | 1.2 |
| 2 | 0.6 | 0.6 |
| 1 | 0.3 | 0.3 |

*Note:
All concentrations in ng/mL.

Calibration Curve Dilutions:

| Std # | Diluent (Biocell Serum-mL) | Std Added (mL) | Std Used |
|---|---|---|---|
| 12 | 0.0 | As Needed (Undiluted) | 12 |
| 11 | 0.4 | 1.6 | 12 |
| 10 | 0.4 | 0.6 | 12 |

-continued

Calibration Curve Dilutions:

| Std # | Diluent (Biocell Serum-mL) | Std Added (mL) | Std Used |
|---|---|---|---|
| 9 | 1.0 | 1.0 | 11 |
| 8 | 0.4 | 0.6 | 11 |
| 7 | 0.8 | 0.3 | 11 |
| 6 | 0.9 | 0.1 | 11 |
| 5 | 1.0 | 1.0 | 6 |
| 4 | 0.8 | 0.3 | 6 |
| 3 | 0.9 | 0.1 | 6 |
| 2 | 0.5 | 0.5 | 3 |
| 1 | 0.9 | 0.1 | 3 |

Calibration Procedure

| Criteria | Special Notations |
|---|---|
| Frequency | A calibration curve is to be set up every assay. |
| Tolerance Limits | Curve fit correlation must be 0.99 or greater. |
| Procedure | Refer to the dilution table in section 5.2. Freeze/Thaw studies were conducted, and showed that the analytes were stable over 5 cycles. Always return Std-12 to the −60° C. to −90° C. freezer as soon as you are finished with it. Use Quadratic curve fit for all analytes, except Endoxifen (linear). Origin's are set to Ignore, and weighting is set to 1/y. |

Equipment and Supplies

Assay Platform

A Thermo LC/MS/MS system containing the following modules was used for this assay:

| Modules |
|---|
| Thermo Quantum Ultra (Serial #022-TQU01376) |
| Cohesive Aria TLX-4 (Serial #SJCTX457) |
| LC Quant Software (Xcalibur, Thermo Fisher) |
| Aria 1.6 Software |
| Agilent G1312 Binary Pumps |
| Thermo APCI Source |

Equipment

| Equipment | Supplier | Cat # |
|---|---|---|
| SPE Positive Pressure Manifold | SPEWare Corp | |
| BDS Hypersil C18, 150 × 4.6, 5u | Thermo Scientific | P/N 28105-154630 |
| Eppindorf Repeater Pipette | Eppindorf/Cardinal Health | P5063-20 |
| Gilson P-200 Pipette | Gilson | |
| Gilson P-1000 Pipette | Gilson | |
| 20 mL Scintillation Vials w/white cap | Warehouse | Stock Clerk #128623VX- |
| 2500 Multi-Tube Vortexer | VWR/SP | |

Supplies

| Supply | Supplier | Cat # |
|---|---|---|
| 250 uL Rainen Pipette Tips | Rainen | HR-250 |
| 1000 uL Pipette Tips | Rainen | HR-1000 |
| Thermo 96 Deep Well Plates | Thermo Scientific | P/N 260252 |
| Thermo Pre-Slit Well Cap for 96 Well PP Plate | Thermo Scientific | P/N 276011 |
| Sirocco Protein Precipitation Plate, 5/pk | Waters Corp | P/N 186002448 |

Mass Spectrometry

| Analyte | Retention Time (RT) Expected | Parent Ion | Product Ion |
|---|---|---|---|
| Tamoxifen | 4.93 | 372.2 | 72.15 |
| E/Z Tamoxifen-d5 | 4.42(E), 4.90(Z)* | 377.2 | 72.18 |
| N-Desmethyl Tamoxifen | 4.65 | 358.2 | 58.15 |
| N-Desmethyl Tamoxifen-d5 | 4.62 | 363.2 | 58.13 |
| 4-Hydroxy Tamoxifen | 1.68 | 388.2 | 72.15 |
| (Z)-4-Hydroxy Tamoxifen-d5 | 1.64 | 393.2 | 72.15 |
| 4'-Hydroxy Tamoxifen | 2.86 | 388.2 | 72.15 |
| 4'-Hydroxy Tamoxifen-d6 | 2.84 | 394.2 | 78.18 |
| N-Desmethyl-4-Hydroxy Tamoxifen (Endoxifen) | 1.16 | 374.2 | 58.15 |
| N-Desmethyl-4-Hydroxy Tamoxifen-d5 | 1.16 | 379.24 | 58.15 |
| N-Desmethyl-4'-Hydroxy Tamoxifen | 2.40 | 374.2 | 58.15 |
| N-Desmethyl-4'Hydroxy Tamoxifen-d3 | 2.38 | 377.2 | 61.20 |

*The Z-form is the active form that is monitored.

Expected Values

Reference Ranges:

Tamoxifen: 12.54-233.07 ng/mL

N-Desmethyl Tamoxifen: 2.59-373.96 ng/mL

4'-Hydroxy Tamoxifen: 0.4-6.33 ng/mL

4-Hydroxy Tamoxifen: 0.24-5.05 ng/mL

N-Desmethyl-4-Hydroxy Tamoxifen (Endoxifen): 0.93-43.19 ng/mL

N-Desmethyl-4'-Hydroxy Tamoxifen: 1.17-19.95 ng/mL

Analytical Measurement Range (AMR)

Tamoxifen: 1.47-1500 ng/mL

N-Desmethyl Tamoxifen: 1.47-1500 ng/mL

4'-Hydroxy Tamoxifen: 0.2-200 ng/mL

4-Hydroxy Tamoxifen: 0.2-200 ng/mL

N-Desmethyl-4-Hydroxy Tamoxifen (Endoxifen): 0.39-400 ng/mL

N-Desmethyl-4'-Hydroxy Tamoxifen: 0.39-400 ng/mL

Precision: Inter- (span of assay) and intra-assay (1 day) precision studies were performed using the low, medium, and high controls. All analytes showed a <12% CV over the span of the validation.

Interfering Substances: Mild or moderate icteric and lipemic samples are acceptable. Hemolytic samples are not acceptable, as they will clog the filter during sample prep. Grossly hemolyzed, icteric, and lipemic samples are not acceptable.

Clinical Sensitivity (LOQ):

Tamoxifen: 1.47 ng/mL

N-Desmethyl Tamoxifen: 1.46 ng/mL

4'-Hydroxy Tamoxifen: 0.2 ng/mL

4-Hydroxy Tamoxifen: 0.2 ng/mL

N-Desmethyl-4-Hydroxy Tamoxifen (Endoxifen): 0.39 ng/mL

N-Desmethyl-4'-Hydroxy Tamoxifen: 0.39 ng/mL

Example 2: Validation of Tamoxifen and its Metabolites Assay

This report contains a detailed summary of the validation for Tamoxifen and its 5 main phase I metabolites by LC/MS/MS. The assay is a laboratory-developed test.

Methodology: Tamoxifen and its five main phase I metabolites (N-desmethyl tamoxifen, N-Desmethyl-4-hydroxytamoxifen, N-desmethyl-4'-hydroxytamoxifen, 4-hydroxytamoxifen, and 4'-hydroxytamoxifen) are extracted from serum. The extraction is a protein precipitation, followed by filtration. Analysis and quantitation is then performed by LC/MS/MS.

Kit or Reagents

| Reagents | Supplier & Catalog Number |
| --- | --- |
| Ammonium Formate | Sigma, 17843-250G |
| Formic Acid | Sigma, F0507-100 mL |
| Ethanol, Absolute, Anhydrous, 200 Proof | Pharmco-AAPER, Cat #111000200 |
| Acetonitrile, HPLC Grade | B&J, Cat #015-4 |
| Biocell Serum, Human Serum, Stripped and Delipidized (Opticlear) | Biocell Labs, Cat #1121-00 |
| Tamoxifen | Toronto Research Labs (TRC), Cat #T006000 |
| N-Desmethyl Tamoxifen HCl | Toronto Research Labs (TRC), Cat #D293900 |
| N-Desmethyl-4-Hydroxy Tamoxifen | Toronto Research Labs (TRC), Cat #D292043 |
| N-Desmethyl-4'-Hydroxy Tamoxifen | Toronto Research Labs (TRC), Cat #D292041 |
| (Z)-4-Hydroxy Tamoxifen | Toronto Research Labs (TRC), Cat #H954725 |
| 4'-Hydroxy Tamoxifen | Toronto Research Labs (TRC), Cat #H954730 |
| (E/Z)-Tamoxifen-d5 | Toronto Research Labs (TRC), Cat #T006007 |
| N-Desmethyl Tamoxifen-d5 | Toronto Research Labs (TRC), Cat #D293902 |
| N-Desmethyl-4-Hydroxy Tamoxifen-d5 | Toronto Research Labs (TRC), Cat #D292044 |
| N-Desmethyl-4'-Hydroxy Tamoxifen-d3 | Toronto Research Labs (TRC), Cat #D291867 |
| (Z)-4-Hydroxy Tamoxifen-d5 | Toronto Research Labs (TRC), Cat #H954757 |
| 4'-Hydroxy Tamoxifen-d6 | Toronto Research Labs (TRC), Cat #H954757 |

Precision Study for Laboratory Developed Tests (LDT)

Within Run Precision: Low, medium, and high controls were analyzed (10) within one run. All QC fell within acceptability criteria (<20% CV).

| | Endoxifen (ng/mL) | 4-OH-Tamoxifen (ng/mL) | N-DM-4'OH-Tamoxifen (ng/mL) | 4'OH-Tamoxifen (ng/mL) | N-DM-Tamoxifen (ng/mL) | Tamoxifen (ng/mL) |
| --- | --- | --- | --- | --- | --- | --- |
| Low Control | | | | | | |
| 1 | 11.479 | 1.582 | 10.170 | 1.926 | 34.728 | 32.814 |
| 2 | 7.510 | 1.806 | 8.915 | 1.757 | 32.952 | 39.576 |
| 3 | 8.580 | 1.751 | 9.064 | 1.552 | 36.389 | 37.948 |
| 4 | 9.156 | 1.833 | 9.196 | 1.641 | 35.488 | 33.814 |
| 5 | 9.805 | 1.844 | 9.221 | 1.643 | 33.879 | 31.212 |
| 6 | 9.088 | 2.132 | 8.785 | 1.758 | 32.435 | 34.300 |
| 7 | 8.821 | 2.079 | 8.569 | 1.559 | 33.555 | 36.784 |
| 8 | 7.304 | 2.383 | 8.440 | 1.994 | 35.117 | 33.327 |
| 9 | 9.921 | 2.119 | 9.136 | 1.745 | 37.190 | 33.794 |
| 10 | 8.550 | 2.192 | 8.102 | 1.845 | 38.720 | 36.350 |
| Mean | 9.02 | 1.97 | 8.96 | 1.74 | 35.05 | 34.99 |
| Stdev | 1.21 | 0.24 | 0.56 | 0.15 | 1.97 | 2.58 |
| % CV | 13.41 | 12.42 | 6.25 | 8.51 | 5.63 | 7.37 |
| Middle Control | | | | | | |
| 1 | 83.799 | 39.593 | 80.603 | 34.332 | 165.439 | 186.498 |
| 2 | 88.134 | 37.585 | 79.798 | 36.082 | 181.275 | 205.514 |
| 3 | 84.445 | 35.894 | 77.389 | 36.070 | 164.816 | 172.721 |
| 4 | 83.364 | 36.412 | 83.648 | 34.483 | 164.643 | 174.957 |
| 5 | 82.632 | 35.697 | 83.397 | 35.866 | 176.518 | 177.587 |
| 6 | 88.988 | 37.536 | 75.551 | 31.615 | 170.129 | 182.202 |
| 7 | 85.351 | 38.475 | 80.059 | 35.940 | 162.261 | 198.626 |
| 8 | 81.834 | 38.402 | 77.803 | 32.461 | 176.554 | 184.688 |
| 9 | 86.598 | 39.946 | 84.175 | 35.302 | 163.246 | 204.461 |
| 10 | 95.135 | 37.530 | 79.668 | 37.393 | 196.225 | 187.704 |
| Mean | 86.03 | 37.71 | 80.21 | 34.95 | 172.11 | 187.50 |
| Stdev | 3.95 | 1.44 | 2.86 | 1.78 | 10.74 | 11.77 |
| % CV | 4.59 | 3.83 | 3.57 | 5.08 | 6.24 | 6.28 |
| High Control | | | | | | |
| 1 | 189.670 | 93.480 | 188.415 | 92.408 | 658.605 | 858.395 |
| 2 | 201.279 | 91.872 | 189.325 | 91.608 | 755.094 | 882.797 |
| 3 | 189.009 | 95.969 | 174.819 | 84.116 | 724.537 | 780.958 |
| 4 | 201.229 | 92.422 | 190.193 | 87.989 | 719.015 | 887.024 |
| 5 | 198.358 | 88.508 | 181.242 | 92.937 | 683.269 | 763.216 |
| 6 | 170.784 | 85.174 | 177.770 | 85.490 | 721.171 | 823.250 |
| 7 | 184.641 | 98.301 | 172.371 | 86.206 | 706.818 | 783.975 |

-continued

|  | Endoxifen (ng/mL) | 4-OH-Tamoxifen (ng/mL) | N-DM-4'OH-Tamoxifen (ng/mL) | 4'OH-Tamoxifen (ng/mL) | N-DM-Tamoxifen (ng/mL) | Tamoxifen (ng/mL) |
|---|---|---|---|---|---|---|
| 8 | 205.803 | 89.703 | 184.633 | 84.096 | 712.341 | 784.042 |
| 9 | 190.205 | 94.532 | 164.908 | 84.977 | 723.057 | 805.741 |
| 10 | 190.731 | 89.605 | 189.710 | 96.315 | 737.294 | 819.099 |
| Mean | 192.17 | 91.96 | 181.34 | 88.61 | 714.12 | 818.85 |
| Stdev | 10.14 | 3.86 | 8.68 | 4.36 | 27.01 | 44.03 |
| % CV | 5.28 | 4.20 | 4.79 | 4.92 | 3.78 | 5.38 |

Total Precision: Total precision was based on all QC run on all assays during the validation process. Acceptability was based on <20% CV. All QC fell within this criteria.

|  | Endoxifen (ng/mL) | 4-OH-Tamoxifen (ng/mL) | N-DM-4'OH-Tamoxifen (ng/mL) | 4'OH-Tamoxifen (ng/mL) | N-DM-Tamoxifen (ng/mL) | Tamoxifen (ng/mL) |
|---|---|---|---|---|---|---|
| Low Control |  |  |  |  |  |  |
| 1 | 11.592 | 2.285 | 8.663 | 1.525 | 36.145 | 35.525 |
| 2 | 11.138 | 2.277 | 9.762 | 2.168 | 40.870 | 38.152 |
| 3 | 8.890 | 2.519 | 10.094 | 2.145 | 40.451 | 37.248 |
| 4 | 10.022 | 2.417 | 10.096 | 2.363 | 34.538 | 38.348 |
| 5 | 10.377 | 1.964 | 9.531 | 2.130 | 40.335 | 37.198 |
| 1 | 8.917 | 2.169 | 8.172 | 1.932 | 34.775 | 35.754 |
| 2 | 9.833 | 1.926 | 9.707 | 1.953 | 37.485 | 34.955 |
| 3 | 8.974 | 2.066 | 9.451 | 2.239 | 36.460 | 36.176 |
| 4 | 9.810 | 2.035 | 8.760 | 1.621 | 32.040 | 32.630 |
| 5 | 10.367 | 1.751 | 8.983 | 1.847 | 36.114 | 37.263 |
| 1 | 12.282 | 2.410 | 8.462 | 2.106 | 34.382 | 33.980 |
| 2 | 8.801 | 2.418 | 9.214 | 1.696 | 38.913 | 37.524 |
| 3 | 10.512 | 1.650 | 9.246 | 2.038 | 35.886 | 39.920 |
| 4 | 9.479 | 2.072 | 8.300 | 1.925 | 40.630 | 40.013 |
| 5 | 9.487 | 2.094 | 9.062 | 2.260 | 35.468 | 40.544 |
| 1 | 13.192 | 2.172 | 9.722 | 2.067 | 34.702 | 36.737 |
| 2 | 11.281 | 1.876 | 9.876 | 1.723 | 31.707 | 36.750 |
| 3 | 9.727 | 1.778 | 9.547 | 2.085 | 38.602 | 34.458 |
| 4 | 10.920 | 1.956 | 9.623 | 1.902 | 35.276 | 36.427 |
| 5 | 10.765 | 1.878 | 10.720 | 2.196 | 32.678 | 37.328 |
| 1 | 9.905 | 2.267 | 9.573 | 1.756 | 34.575 | 40.865 |
| 2 | 9.517 | 2.419 | 10.397 | 1.852 | 38.703 | 38.931 |
| 3 | 10.592 | 2.089 | 10.440 | 1.768 | 36.104 | 39.576 |
| 4 | 9.705 | 2.161 | 10.924 | 1.881 | 37.768 | 40.039 |
| 5 | 9.299 | 1.964 | 9.492 | 1.660 | 35.499 | 37.825 |
| 1 | 10.312 | 2.195 | 11.309 | 1.952 | 37.109 | 37.409 |
| 2 | 8.540 | 2.084 | 10.329 | 1.848 | 32.896 | 39.378 |
| 1 | 9.971 | 2.699 | 10.214 | 1.968 | 37.176 | 38.498 |
| 2 | 10.845 | 2.264 | 8.237 | 1.985 | 38.033 | 42.613 |
| 3 | 9.275 | 2.184 | 8.027 | 1.590 | 32.633 | 34.847 |
| 4 | 7.925 | 2.569 | 7.925 | 2.166 | 35.327 | 35.302 |
| 5 | 8.041 | 2.312 | 7.885 | 1.891 | 31.681 | 36.267 |
| 1 | 8.636 | 2.075 | 9.928 | 2.023 | 34.570 | 38.068 |
| 2 | 10.653 | 2.122 | 10.316 | 2.038 | 39.078 | 38.219 |
| 1 | 10.003 | 2.559 | 9.009 | 2.401 | 41.780 | 38.067 |
| 2 | 13.146 | 2.143 | 9.527 | 2.285 | 37.945 | 36.085 |
| 1 | 9.319 | 2.202 | 9.477 | 2.347 | 34.554 | 38.110 |
| 2 | 8.029 | 1.836 | 8.287 | 1.789 | 33.201 | 30.038 |
| 3 | 9.012 | 2.140 | 8.720 | 1.974 | 35.778 | 34.251 |
| 4 | 8.299 | 2.037 | 9.456 | 2.119 | 38.542 | 37.302 |
| 1 | 9.606 | 2.449 | 10.127 | 2.619 | 38.680 | 42.268 |
| 2 | 11.108 | 2.410 | 9.118 | 2.570 | 38.456 | 42.861 |
| 3 | 11.502 | 2.288 | 8.941 | 2.224 | 36.295 | 39.003 |
| 4 | 9.983 | 2.536 | 9.583 | 2.301 | 39.444 | 42.359 |
| 1 | 10.863 | 2.027 | 9.713 | 1.955 | 39.137 | 36.636 |
| 2 | 9.912 | 2.046 | 8.556 | 2.133 | 35.665 | 38.773 |
| 1 | 9.603 | 2.247 | 7.986 | 2.063 | 42.388 | 39.865 |
| 2 | 9.305 | 2.071 | 9.373 | 2.197 | 37.447 | 39.204 |
| 1 | 8.518 | 2.203 | 9.189 | 2.097 | 36.600 | 34.954 |
| 2 | 8.727 | 2.108 | 8.134 | 1.868 | 33.344 | 33.870 |
| 3 | 9.676 | 2.242 | 8.135 | 2.234 | 34.319 | 35.267 |
| 4 | 8.867 | 2.041 | 7.973 | 2.008 | 36.328 | 36.998 |
| 1 | 8.988 | 2.006 | 10.200 | 2.013 | 37.349 | 36.239 |
| 2 | 9.274 | 1.870 | 9.697 | 1.967 | 38.264 | 38.313 |

-continued

| | Endoxifen (ng/mL) | 4-OH-Tamoxifen (ng/mL) | N-DM-4'OH-Tamoxifen (ng/mL) | 4'OH-Tamoxifen (ng/mL) | N-DM-Tamoxifen (ng/mL) | Tamoxifen (ng/mL) |
|---|---|---|---|---|---|---|
| 1 | 9.503 | 1.919 | 9.453 | 2.068 | 43.706 | 33.935 |
| 2 | 9.703 | 2.007 | 8.722 | 1.874 | 40.296 | 34.916 |
| Mean | 9.87 | 2.15 | 9.31 | 2.03 | 36.75 | 37.39 |
| Std Dev | 1.15 | 0.22 | 0.83 | 0.23 | 2.77 | 2.55 |
| CV | 11.65 | 10.36 | 8.96 | 11.29 | 7.53 | 6.82 |
| Middle Control | | | | | | |
| 1 | 87.010 | 39.746 | 89.637 | 42.407 | 202.496 | 210.097 |
| 2 | 94.595 | 39.218 | 101.461 | 43.252 | 220.163 | 203.365 |
| 3 | 96.338 | 41.161 | 103.091 | 41.130 | 210.035 | 237.872 |
| 4 | 100.952 | 40.926 | 97.656 | 45.079 | 194.037 | 203.374 |
| 5 | 92.546 | 42.034 | 90.246 | 41.105 | 180.896 | 234.350 |
| 1 | 86.522 | 38.422 | 82.806 | 37.133 | 170.911 | 189.278 |
| 2 | 86.982 | 35.883 | 89.719 | 35.175 | 182.954 | 200.267 |
| 3 | 94.330 | 37.402 | 83.686 | 38.187 | 187.342 | 186.339 |
| 4 | 86.088 | 37.256 | 90.762 | 37.099 | 177.586 | 167.783 |
| 5 | 90.805 | 36.694 | 88.020 | 37.999 | 186.762 | 176.707 |
| 1 | 88.741 | 38.437 | 77.735 | 34.791 | 188.429 | 170.437 |
| 2 | 93.659 | 38.068 | 86.365 | 37.361 | 182.615 | 185.327 |
| 3 | 89.770 | 39.654 | 76.566 | 33.949 | 184.621 | 210.695 |
| 4 | 94.247 | 38.336 | 80.834 | 35.738 | 182.464 | 201.245 |
| 5 | 88.359 | 39.617 | 79.947 | 38.285 | 196.110 | 185.179 |
| 1 | 96.013 | 38.875 | 94.650 | 38.235 | 192.418 | 178.464 |
| 2 | 89.914 | 35.280 | 74.974 | 34.501 | 195.061 | 174.347 |
| 3 | 90.408 | 36.250 | 94.097 | 36.874 | 192.154 | 180.649 |
| 4 | 86.933 | 35.653 | 88.543 | 37.264 | 198.757 | 172.231 |
| 5 | 105.603 | 37.055 | 96.923 | 39.572 | 166.573 | 188.035 |
| 1 | 96.715 | 38.736 | 91.402 | 38.503 | 193.668 | 192.852 |
| 2 | 85.550 | 38.719 | 91.593 | 38.211 | 192.601 | 203.520 |
| 3 | 96.364 | 40.895 | 97.744 | 40.532 | 203.027 | 210.815 |
| 4 | 89.677 | 39.397 | 77.862 | 36.283 | 190.794 | 191.809 |
| 5 | 84.419 | 36.150 | 87.890 | 36.258 | 203.371 | 192.906 |
| 1 | 87.929 | 38.550 | 88.816 | 36.835 | 181.353 | 197.693 |
| 2 | 74.719 | 36.294 | 87.041 | 34.933 | 179.365 | 190.056 |
| 1 | 83.567 | 36.801 | 83.282 | 39.022 | 177.547 | 177.361 |
| 2 | 75.551 | 33.187 | 85.481 | 34.572 | 153.055 | 159.856 |
| 3 | 87.804 | 38.901 | 71.354 | 28.960 | 166.592 | 192.261 |
| 4 | 82.223 | 37.510 | 72.808 | 29.301 | 166.157 | 179.546 |
| 5 | 85.341 | 39.784 | 71.964 | 30.776 | 171.216 | 205.388 |
| 1 | 88.004 | 33.537 | 90.680 | 33.157 | 195.955 | 187.743 |
| 2 | 86.158 | 39.113 | 89.815 | 35.488 | 184.322 | 189.194 |
| 1 | 88.728 | 41.774 | 76.301 | 35.150 | 179.239 | 217.475 |
| 2 | 100.988 | 37.906 | 80.538 | 36.629 | 197.328 | 202.671 |
| 1 | 84.292 | 35.389 | 90.935 | 35.702 | 184.883 | 189.455 |
| 2 | 88.520 | 34.514 | 95.314 | 35.561 | 183.190 | 172.592 |
| 3 | 83.439 | 37.285 | 95.351 | 37.955 | 180.218 | 173.995 |
| 4 | 86.701 | 37.091 | 88.160 | 36.253 | 192.596 | 180.127 |
| 1 | 86.049 | 37.984 | 83.921 | 36.871 | 172.997 | 224.122 |
| 2 | 91.295 | 39.390 | 92.291 | 39.164 | 185.491 | 202.409 |
| 3 | 88.654 | 38.989 | 85.121 | 38.139 | 177.713 | 213.566 |
| 4 | 89.973 | 40.718 | 93.456 | 39.341 | 197.407 | 215.637 |
| 1 | 93.239 | 42.549 | 91.506 | 38.826 | 181.470 | 205.651 |
| 2 | 98.907 | 38.658 | 82.931 | 36.807 | 198.912 | 216.152 |
| 1 | 93.912 | 38.063 | 89.926 | 35.099 | 188.095 | 222.914 |
| 2 | 83.242 | 34.984 | 88.570 | 37.402 | 200.103 | 210.098 |
| 1 | 96.655 | 38.764 | 81.895 | 36.921 | 173.766 | 179.647 |
| 2 | 93.507 | 36.178 | 87.743 | 37.688 | 169.649 | 196.749 |
| 3 | 97.061 | 39.966 | 86.633 | 39.299 | 174.694 | 195.119 |
| 4 | 97.760 | 41.871 | 92.541 | 40.805 | 198.256 | 192.921 |
| 1 | 88.496 | 38.325 | 87.354 | 37.319 | 189.199 | 184.837 |
| 2 | 85.028 | 38.332 | 87.345 | 38.125 | 177.596 | 193.024 |
| 1 | 86.758 | 38.894 | 88.755 | 37.777 | 198.350 | 197.001 |
| 2 | 87.200 | 36.649 | 86.536 | 37.594 | 205.277 | 185.319 |
| Mean | 89.90 | 38.18 | 87.30 | 37.19 | 186.75 | 194.62 |
| Std Dev | 5.88 | 2.08 | 7.06 | 2.91 | 12.48 | 16.69 |
| CV | 6.54 | 5.44 | 8.08 | 7.82 | 6.68 | 8.58 |
| High Control | | | | | | |
| 1 | 207.479 | 101.732 | 195.254 | 102.024 | 799.588 | 735.969 |
| 2 | 190.387 | 102.016 | 226.236 | 108.850 | 860.365 | 798.839 |
| 3 | 202.213 | 98.424 | 199.550 | 101.300 | 856.971 | 783.327 |
| 4 | 210.429 | 102.722 | 202.273 | 106.471 | 811.375 | 829.711 |
| 5 | 212.515 | 109.031 | 222.061 | 111.194 | 857.859 | 859.031 |

-continued

|   | Endoxifen (ng/mL) | 4-OH-Tamoxifen (ng/mL) | N-DM-4'OH-Tamoxifen (ng/mL) | 4'OH-Tamoxifen (ng/mL) | N-DM-Tamoxifen (ng/mL) | Tamoxifen (ng/mL) |
|---|---|---|---|---|---|---|
| 1 | 196.747 | 103.011 | 204.676 | 99.578 | 816.049 | 747.992 |
| 2 | 206.775 | 95.510 | 180.867 | 87.664 | 710.089 | 875.109 |
| 3 | 186.389 | 95.141 | 195.533 | 88.284 | 671.914 | 798.004 |
| 4 | 184.079 | 93.074 | 170.879 | 85.515 | 680.514 | 748.155 |
| 5 | 196.620 | 93.918 | 166.410 | 91.662 | 696.733 | 813.829 |
| 1 | 181.815 | 101.602 | 205.865 | 92.189 | 786.902 | 889.986 |
| 2 | 204.310 | 94.568 | 194.635 | 92.144 | 823.327 | 787.045 |
| 3 | 203.649 | 95.490 | 182.781 | 85.872 | 790.504 | 798.055 |
| 4 | 205.176 | 92.576 | 189.464 | 89.338 | 758.539 | 768.107 |
| 5 | 202.342 | 96.793 | 176.749 | 92.032 | 846.377 | 727.994 |
| 1 | 198.640 | 98.625 | 196.187 | 95.798 | 810.498 | 728.474 |
| 2 | 198.899 | 91.019 | 187.599 | 100.136 | 751.812 | 805.304 |
| 3 | 199.035 | 84.927 | 179.312 | 95.215 | 737.664 | 770.813 |
| 4 | 212.276 | 84.154 | 190.044 | 100.630 | 734.151 | 886.035 |
| 5 | 200.109 | 92.086 | 194.237 | 99.469 | 760.246 | 872.936 |
| 1 | 200.469 | 89.448 | 199.269 | 91.661 | 729.412 | 834.619 |
| 2 | 202.977 | 98.208 | 199.034 | 96.375 | 790.310 | 799.638 |
| 3 | 205.475 | 93.973 | 192.105 | 92.720 | 798.244 | 810.004 |
| 4 | 197.479 | 99.860 | 196.147 | 94.396 | 761.732 | 783.978 |
| 5 | 194.612 | 94.240 | 197.186 | 97.771 | 786.241 | 771.571 |
| 1 | 186.505 | 81.241 | 198.300 | 87.311 | 710.289 | 749.671 |
| 2 | 176.188 | 89.968 | 181.780 | 79.731 | 731.985 | 741.325 |
| 1 | 199.356 | 87.775 | 207.198 | 101.803 | 748.141 | 771.557 |
| 2 | 222.589 | 105.058 | 196.074 | 90.785 | 801.007 | 942.577 |
| 3 | 181.161 | 94.362 | 148.799 | 78.682 | 617.203 | 695.000 |
| 4 | 215.118 | 100.450 | 158.172 | 79.628 | 750.937 | 839.526 |
| 5 | 191.211 | 102.290 | 163.134 | 79.661 | 725.107 | 704.289 |
| 1 | 196.775 | 98.926 | 191.427 | 91.397 | 676.187 | 806.089 |
| 2 | 218.733 | 94.497 | 188.927 | 83.249 | 702.543 | 764.559 |
| 1 | 189.423 | 103.108 | 176.834 | 85.740 | 787.894 | 783.972 |
| 2 | 203.993 | 104.811 | 242.863 | 100.905 | 744.233 | 775.926 |
| 1 | 200.471 | 95.865 | 198.445 | 89.203 | 766.594 | 768.276 |
| 2 | 202.665 | 90.224 | 209.309 | 97.688 | 728.383 | 781.862 |
| 3 | 204.180 | 101.425 | 203.688 | 92.536 | 677.014 | 860.784 |
| 4 | 199.399 | 86.145 | 187.369 | 82.171 | 719.400 | 701.285 |
| 1 | 197.465 | 92.884 | 200.642 | 95.198 | 736.030 | 826.979 |
| 2 | 190.613 | 93.842 | 183.426 | 97.415 | 744.250 | 800.504 |
| 3 | 199.096 | 96.602 | 193.312 | 96.739 | 746.794 | 776.233 |
| 4 | 179.140 | 87.981 | 197.976 | 93.276 | 691.001 | 866.107 |
| 1 | 199.248 | 95.517 | 205.052 | 89.399 | 718.152 | 830.034 |
| 2 | 217.882 | 94.943 | 190.257 | 89.531 | 720.014 | 762.305 |
| 1 | 200.190 | 93.715 | 197.387 | 100.663 | 748.026 | 831.065 |
| 2 | 213.258 | 94.615 | 190.476 | 91.976 | 762.683 | 800.202 |
| 1 | 185.724 | 96.274 | 187.941 | 94.235 | 707.147 | 798.423 |
| 2 | 217.069 | 101.477 | 191.859 | 96.905 | 823.232 | 803.716 |
| 3 | 213.982 | 95.430 | 181.301 | 98.054 | 700.987 | 770.842 |
| 4 | 199.874 | 92.896 | 172.759 | 92.304 | 735.885 | 814.102 |
| 1 | 182.741 | 98.602 | 185.285 | 95.342 | 715.912 | 774.003 |
| 2 | 182.816 | 90.468 | 216.778 | 95.733 | 747.020 | 861.042 |
| 1 | 179.231 | 95.177 | 187.040 | 88.321 | 748.849 | 740.018 |
| 2 | 198.872 | 89.425 | 194.280 | 92.437 | 758.636 | 851.201 |
| Mean | 199.03 | 95.50 | 192.37 | 93.33 | 752.12 | 796.75 |
| Std Dev | 11.02 | 5.62 | 15.76 | 7.07 | 51.25 | 50.69 |
| CV | 5.53 | 5.89 | 8.19 | 7.57 | 6.81 | 6.36 |

Analytical Sensitivity (Detection Limits)

Limit of Detection (LOD): Limit of detection (LOD) was performed by taking a low pool (containing all analytes), then serially diluting (1:2) down to the lowest observable level. Assuming the linearity were to continue below the level of quantitation (LOQ), the values below would be the lowest quantifiable concentrations. This experiment was performed over 5 days.

Tamoxifen=0.59 ng/mL

N-Desmethyl Tamoxifen=0.59 ng/mL

4'-Hydroxy Tamoxifen=0.1 ng/mL

N-Desmethyl-4'-Hydroxy Tamoxifen=0.5 ng/mL

4-Hydroxy Tamoxifen=0.1 ng/mL

N-Desmethyl-4-Hydroxy Tamoxifen (Endoxifen)=0.15 ng/mL

Limit of Quantitation (LOQ): The acceptability criteria for the LOQ is defined as the lowest concentration at which CV<20%. To determine the LOQ, a mid-level standard was diluted down serially 1:2.

Tamoxifen=1.5 ng/mL

N-Desmethyl Tamoxifen=1.5 ng/mL

4'-Hydroxy Tamoxifen=0.4 ng/mL

N-Desmethyl-4'-Hydroxy Tamoxifen=0.4 ng/mL

4-Hydroxy Tamoxifen=0.2 ng/mL

N-Desmethyl-4-Hydroxy Tamoxifen (Endoxifen)=0.4 ng/mL

Accuracy

Recovery of Known Standards: Serum was spiked with all analytes to specific concentrations, extracted, and then analyzed in triplicate. All mixes were spiked to cover the linear and therapeutic range of each analyte.

|  | Specified | Calc. Conc. (ng/mL) | | | | | | |
| --- | --- | --- | --- | --- | --- | --- | --- | --- |
|  | Conc. (ng/mL) | 1 | 2 | 3 | Mean | Std Dev | CV | % Recov |
| Mix1 | | | | | | | | |
| Endoxifen | 10 | 9.52 | 10.20 | 10.96 | 10.23 | 0.72 | 7.04 | 102.27 |
| 4OH Tamoxifen | 200 | 202.34 | 200.34 | 217.89 | 206.86 | 9.61 | 4.64 | 103.43 |
| N-DM 4' OH Tam | 10 | 10.03 | 9.19 | 8.82 | 9.35 | 0.62 | 6.61 | 93.50 |
| 4' OH Tamoxifen | 200 | 188.92 | 180.49 | 220.38 | 196.60 | 21.02 | 10.69 | 98.30 |
| N-DM Tamoxifen | 500 | 456.99 | 433.11 | 469.66 | 453.26 | 18.56 | 4.09 | 90.65 |
| Tamoxifen | 500 | 474.32 | 464.31 | 498.06 | 478.90 | 17.34 | 3.62 | 95.78 |
| | | | | | | | Mean: | 97.32 |
| Mix2 | | | | | | | | |
| Endoxifen | 200 | 188.88 | 186.97 | 164.95 | 180.27 | 13.30 | 7.38 | 90.14 |
| 4OH Tamoxifen | 5 | 4.16 | 4.73 | 4.38 | 4.42 | 0.29 | 6.48 | 88.49 |
| N-DM 4' OH Tam | 200 | 204.90 | 190.67 | 178.00 | 191.20 | 13.45 | 7.04 | 95.60 |
| 4' OH Tamoxifen | 5 | 4.90 | 4.54 | 4.92 | 4.79 | 0.21 | 4.45 | 95.82 |
| N-DM Tamoxifen | 10 | 9.30 | 9.57 | 9.93 | 9.61 | 0.32 | 3.30 | 96.06 |
| Tamoxifen | 10 | 10.03 | 9.18 | 9.88 | 9.70 | 0.45 | 4.67 | 97.00 |
| | | | | | | | Mean: | 93.85 |
| Mix3 | | | | | | | | |
| Endoxifen | 100 | 87.92 | 89.91 | 91.72 | 89.85 | 1.90 | 2.11 | 89.85 |
| 4OH Tamoxifen | 100 | 101.75 | 104.22 | 92.28 | 99.42 | 6.30 | 6.34 | 99.42 |
| N-DM 4' OH Tam | 100 | 98.83 | 91.81 | 92.09 | 94.25 | 3.97 | 4.22 | 94.25 |
| 4' OH Tamoxifen | 100 | 93.10 | 90.39 | 87.88 | 90.46 | 2.61 | 2.89 | 90.46 |
| N-DM Tamoxifen | 1000 | 885.57 | 857.60 | 932.56 | 891.92 | 37.88 | 4.25 | 89.19 |
| Tamoxifen | 1000 | 994.90 | 908.44 | 870.80 | 924.72 | 63.63 | 6.88 | 92.47 |
| | | | | | | | Mean: | 92.61 |
| Mix4 | | | | | | | | |
| Endoxifen | 80 | 74.71 | 73.65 | 75.85 | 74.74 | 1.10 | 1.47 | 93.43 |
| 4OH Tamoxifen | 10 | 7.74 | 10.21 | 9.77 | 9.25 | 1.32 | 14.27 | 92.47 |
| N-DM 4' OH Tam | 80 | 78.97 | 73.72 | 70.50 | 74.40 | 4.28 | 5.75 | 93.00 |
| 4' OH Tamoxifen | 10 | 10.09 | 9.27 | 9.04 | 9.47 | 0.55 | 5.85 | 94.70 |
| N-DMTamoxifen | 100 | 93.31 | 88.07 | 92.50 | 91.30 | 2.82 | 3.09 | 91.30 |
| Tamoxifen | 100 | 97.94 | 107.41 | 99.07 | 101.48 | 5.17 | 5.10 | 101.48 |
| | | | | | | | Mean: | 94.40 |

Interference Study

Acceptability criteria: The difference due to a potential interfering substance should be ≤TEa/4 to be considered acceptable Hemolysis Interference: Low and high pools were spiked with a hemolyzed RBC's at low, medium, and high concentrations. Samples were extracted in quadruplicate. Hemolysis showed no interference with tamoxifen or measured metabolites. However, due to difficulty with filtration from moderate and high hemolysis samples, only mildly hemolyzed samples should be accepted.

|  | Hemolysis | | |
| --- | --- | --- | --- |
|  | Low | Medium | High |
| Low Pool (% Recovery) | | | |
| N-Desmethyl-4-Hydroxy Tamoxifen (Endoxifen) | 109.28 | 110.30 | 115.24 |
| 4-OH-Tamoxifen | 106.99 | 108.40 | 104.81 |
| N-Desmethyl-4'OH Tamoxifen | 96.42 | 105.05 | 97.57 |
| 4'OH-Tamoxifen | 102.37 | 99.02 | 108.24 |
| N-DM-Tamoxifen | 93.52 | 98.47 | 91.98 |
| Tamoxifen | 101.85 | 99.82 | 99.73 |
| High Pool (% Recovery) | | | |
| N-Desmethyl-4-Hydroxy Tamoxifen (Endoxifen) | 97.73 | 97.46 | 93.16 |
| 4-OH-Tamoxifen | 95.75 | 95.78 | 91.03 |
| N-Desmethyl-4'OH Tamoxifen | 98.33 | 95.33 | 95.39 |

-continued

|  | Hemolysis | | |
| --- | --- | --- | --- |
|  | Low | Medium | High |
| 4'OH-Tamoxifen | 99.52 | 101.43 | 103.19 |
| N-DM-Tamoxifen | 92.42 | 95.50 | 93.45 |
| Tamoxifen | 91.51 | 95.13 | 105.25 |

Lipemia Interference: Low and high pools were spiked with a lipemic samples at low, medium, and high concentrations. Samples were extracted in quadruplicate. Lipemic samples showed no interference with tamoxifen or measured metabolites.

|  | Lipemic | | |
| --- | --- | --- | --- |
|  | Low | Medium | High |
| Low Pool (% Recovery) | | | |
| N-Desmethyl-4-Hydroxy Tamoxifen (Endoxifen) | 109.27 | 104.58 | 109.12 |
| 4-OH-Tamoxifen | 113.91 | 104.18 | 113.29 |
| N-Desmethyl-4'OH Tamoxifen | 102.52 | 103.49 | 113.76 |
| 4'OH-Tamoxifen | 106.35 | 93.43 | 98.35 |
| N-DM-Tamoxifen | 97.89 | 97.34 | 90.64 |
| Tamoxifen | 101.74 | 95.64 | 103.72 |

|                                  | Lipemic |        |        |
|----------------------------------|---------|--------|--------|
|                                  | Low     | Medium | High   |
|                                  | High Pool (% Recovery) |  |  |
| N-Desmethyl-4-Hydroxy Tamoxifen (Endoxifen) | 97.21 | 99.49 | 96.19 |
| 4-OH-Tamoxifen                   | 94.63   | 98.42  | 94.17  |
| N-Desmethyl-4'OH Tamoxifen       | 99.16   | 97.77  | 95.75  |
| 4'OH-Tamoxifen                   | 101.37  | 103.79 | 101.82 |
| N-DM-Tamoxifen                   | 91.19   | 94.40  | 102.11 |
| Tamoxifen                        | 87.03   | 96.82  | 94.34  |

Bilirubin Interference: Low and high pools were spiked with a bilirubin at low, medium, and high concentrations. Samples were extracted in quadruplicate. Bilirubin spiked samples showed no interference with tamoxifen or measured metabolites.

|                                  | Bilirubin |        |        |
|----------------------------------|-----------|--------|--------|
|                                  | Low       | Medium | High   |
|                                  | Low Pool (% Recovery) |  |  |
| N-Desmethyl-4-Hydroxy Tamoxifen (Endoxifen) | 91.69 | 110.76 | 100.67 |
| 4-OH-Tamoxifen                   | 114.79    | 102.57 | 110.50 |
| N-Desmethyl-4'OH Tamoxifen       | 107.02    | 103.14 | 100.46 |
| 4'OH-Tamoxifen                   | 91.05     | 96.49  | 103.59 |
| N-DM-Tamoxifen                   | 89.89     | 100.83 | 91.15  |
| Tamoxifen                        | 97.04     | 103.01 | 96.17  |
|                                  | High Pool (% Recovery) |  |  |
| N-Desmethyl-4-Hydroxy Tamoxifen (Endoxifen) | 103.15 | 97.78 | 95.72 |
| 4-OH-Tamoxifen                   | 98.80     | 97.99  | 89.94  |
| N-Desmethyl-4'OH Tamoxifen       | 97.68     | 95.41  | 93.89  |
| 4'OH-Tamoxifen                   | 101.44    | 100.35 | 99.97  |
| N-DM-Tamoxifen                   | 93.84     | 100.36 | 95.32  |
| Tamoxifen                        | 94.63     | 92.75  | 94.80  |

Example 3: Validation of Norendoxifen Assay

This report contains a detailed summary of the validation for Norendoxifen by LC/MS/MS. The assay is a laboratory-developed test.

Norendoxifen is extracted from serum using protein precipitation, followed by filtration. Analysis and quantitation is then performed by LC/MS/MS.

Kit or Reagents

| Reagents | Supplier & Catalog Number |
|----------|---------------------------|
| Ammonium Formate | Sigma, 17843-250G |
| Formic Acid | Sigma, F0507-100 mL |
| Ethanol, Absolute, Anhydrous, 200 Proof | Pharmco-AAPER, Cat #111000200 |
| Acetonitrile, HPLC Grade | B&J, Cat #015-4 |
| Biocell Serum, Human Serum, Stripped and Delipidized (Opticlear) | Biocell Labs, Cat #1121-00 |
| Norendoxifen | Dr. David Flockhart |
| N-Desmethyl-4-Hydroxy Tamoxifen-d5 | Toronto Research Labs (TRC), Cat #D292044 |

Precision Study for Laboratory Developed Tests (LDT)

Within Run Precision: Low, medium, and high controls (ng/mL) were analyzed (10) within one run. All QC fell within acceptability criteria (<20% CV).

| Controls | Low   | Mid    | High   |
|----------|-------|--------|--------|
| 1        | 8.71  | 103.75 | 188.84 |
| 2        | 8.35  | 104.13 | 195.45 |
| 3        | 10.65 | 92.25  | 211.45 |
| 4        | 9.42  | 95.71  | 197.29 |
| 5        | 7.66  | 93.26  | 175.46 |
| 6        | 9.95  | 88.97  | 156.57 |
| 7        | 8.65  | 111.42 | 152.57 |
| 8        | 8.00  | 93.23  | 172.76 |
| 9        | 9.66  | 84.69  | 178.21 |
| 10       | 8.76  | 92.88  | 172.45 |
| mean     | 8.98  | 96.03  | 180.10 |
| std dev  | 0.93  | 8.03   | 18.38  |
| % cv     | 10.30 | 8.36   | 10.20  |

Total Precision: Total precision was based on all QC run on all assays during the validation process. Acceptability was based on <20% CV. All QC fell within this criteria.

Limit of Detection (LOD): Norendoxifen=1.2 ng/mL
Limit of Quantitation (LOQ): Norendoxifen=1.2 ng/mL
Accuracy:

Recovery of Known Standards: Serum was spiked with all analytes to specific concentrations, extracted, and then analyzed in quadruplicate. All mixes were spiked to cover the linear and therapeutic range of each analyte.

| Mix | Exp. Conc | Calculated Concentrations (ng/mL) 1 | 2 | 3 | 4 | Mean | Std Dev | CV | % Recov |
|-----|-----------|-------|--------|--------|--------|--------|---------|-------|---------|
| 1   | 10.00     | 10.67 | 10.53  | 10.27  | 9.04   | 10.13  | 0.75    | 7.37  | 101.26  |
| 2   | 20.00     | 25.49 | 21.84  | 19.60  | 21.83  | 22.19  | 2.44    | 11.01 | 110.95  |
| 3   | 110.00    | 108.48| 110.16 | 117.29 | 102.75 | 109.67 | 5.99    | 5.46  | 99.70   |
| 4   | 150.00    | 150.74| 154.81 | 146.46 | 164.19 | 154.05 | 7.57    | 4.91  | 102.70  |
| 5   | 200.00    | 202.59| 185.39 | 192.42 | 170.60 | 187.75 | 13.44   | 7.16  | 93.87   |
| 6   | 40.00     | 40.40 | 41.99  | 38.88  | 39.59  | 40.22  | 1.33    | 3.32  | 100.54  |

Interference Study

Acceptability criteria: The difference due to a potential interfering substance should be ≤TEa/4 to be considered acceptable Hemolysis Interference: Low and high pools were spiked with a hemolyzed RBC's at low, medium, and high concentrations. Samples were extracted in quadruplicate. Hemolysis showed no interference with norendoxifen. However, due to difficulty with filtration from moderate and high hemolyzed samples, only mildly hemolyzed samples should be accepted.

| % Recovery | | | |
|---|---|---|---|
| Hemolysis | Low | Mid | High |
| Low Pool | 98.80 | 109.49 | 107.30 |
| High Pool | 101.58 | 112.14 | 114.22 |

Lipemia Interference: Low and high pools were spiked with a lipemic samples at low, medium, and high concentrations. Samples were extracted in quadruplicate. Lipemic samples showed no interference with norendoxifen. Recovery of Known Standards: Serum was spiked with all analytes to specific concentrations, extracted, and then analyzed in quadruplicate. All mixes were spiked to cover the linear and therapeutic range of each analyte.

| % Recovery | | | |
|---|---|---|---|
| Lipemic | Low | Mid | High |
| Low Pool | 99.88 | 102.19 | 97.92 |
| High Pool | 100.76 | 96.05 | 92.19 |

Bilirubin Interference: Low and high pools were spiked with a bilirubin at low, medium, and high concentrations. Samples were extracted in quadruplicate. Bilirubin spiked samples showed no interference with norendoxifen.

| % Recovery | | | |
|---|---|---|---|
| Icterus | Low | Mid | High |
| Low Pool | 100.42 | 98.45 | 100.92 |
| High Pool | 95.63 | 96.76 | 94.44 |

Example 4: Clinical Quantitation and Response Study

The standard operating protocol of Examples 1-3 were used to quantitate tamoxifen and its metabolites in patient samples and were correlated to tamoxifen response.

Norendoxifen quantitation and response in patient samples.

| Norendoxifen | | | |
|---|---|---|---|
| Sample ID | Calculated Conc (ng/mL) | Response | ISTD Area |
| 18768 | 0.25 | 4733 | 948878 |
| 18788 | 1.34 | 9020 | 764437 |
| 18824 | 0.88 | 7074 | 793359 |
| 18837 | 1.43 | 7993 | 645545 |
| 18865 | 1.74 | 11233 | 784027 |
| 18873 | 2.02 | 13715 | 851690 |
| 18885 | 1.53 | 18676 | 1434599 |
| 20434 | 0.14 | 6485 | 1524835 |
| 20478 | 0.35 | 10472 | 1873595 |
| 20484 | 0.44 | 8693 | 1411744 |
| 20511 | 1.55 | 19241 | 1466708 |
| 20515 | 0.82 | 11924 | 1392281 |
| 20564 | 2.38 | 27537 | 1498317 |
| 20573 | 1.63 | 19951 | 1461115 |
| 20581 | 3.33 | 34700 | 1426339 |
| 20601 | 3.22 | 37814 | 1599850 |
| 20647 | 4.45 | 46786 | 1490262 |
| 20611 | 3.25 | 33755 | 1415658 |
| 20689 | 4.36 | 44265 | 1436705 |
| 20704 | 4.62 | 47340 | 1458681 |
| 26616 | 0.48 | 9695 | 1508141 |
| 26690 | 1.03 | 14558 | 1475191 |
| 26756 | 1.25 | 16288 | 1447066 |
| 26777 | 2.02 | 20735 | 1287689 |
| 26801 | 1.70 | 18633 | 1323903 |
| 26826 | 2.12 | 16022 | 959275 |
| 26837 | 0.24 | 5498 | 1115449 |
| 26853 | 2.51 | 18098 | 944719 |
| 26864 | 1.13 | 8617 | 822666 |
| 26878 | 2.40 | 14663 | 794035 |
| 26939 | 1.38 | 9809 | 812995 |
| 26952 | 1.23 | 9836 | 886924 |
| 26958 | 0.95 | 6946 | 744284 |
| 26978 | 1.67 | 12349 | 887541 |
| 27009 | 1.15 | 8821 | 828349 |
| 27011 | 2.49 | 16676 | 876309 |
| 27022 | 1.23 | 7675 | 689142 |
| 27045 | 1.34 | 8099 | 686202 |
| 27067 | −0.16 | 1477 | 615842 |
| 27080 | 0.19 | 3606 | 785747 |
| 27084 | 0.31 | 4276 | 798627 |
| 27413 | 1.04 | 4611 | 465635 |
| 27446 | −0.32 | 883 | 630981 |
| 27482 | 1.33 | 7572 | 643410 |
| 27526 | 2.78 | 12639 | 606397 |
| 27539 | 1.72 | 8159 | 574207 |
| 30002 | 0.26 | 2344 | 466484 |
| 30031 | 0.89 | 4453 | 495349 |
| 30043 | 0.51 | 3321 | 505290 |
| 30079 | 3.53 | 12938 | 505353 |
| 30105 | 1.54 | 9701 | 743460 |
| 30116 | 0.92 | 6705 | 731395 |
| 30127 | 1.90 | 9658 | 629546 |
| 6420 | 0.41 | 6415 | 1070269 |
| 6482 | 1.61 | 15116 | 1121187 |
| 6497 | 1.40 | 14181 | 1162006 |
| 6510 | 0.73 | 6127 | 767435 |
| 6521 | 1.68 | 9575 | 687725 |
| 6535 | 1.03 | 8685 | 882954 |
| 6549 | 3.54 | 25094 | 978851 |
| 1 | 1.22 | 11722 | 1062595 |
| 2 | 2.22 | 18544 | 1069320 |
| 3 | 4.61 | 36683 | 1132746 |
| 4 | 17.07 | 117804 | 1056612 |
| 5 | 11.63 | 90103 | 1172890 |
| 6 | 23.61 | 178911 | 1166491 |
| 7 | 60.70 | 453821 | 1145572 |
| 8 | 99.24 | 751764 | 1143017 |
| 9 | 119.62 | 930278 | 1163094 |
| 10 | 172.94 | 1298434 | 1096393 |
| 11 | 238.57 | 1803403 | 1071971 |
| 12 | 304.02 | 2532623 | 1147835 |
| Low1 | 8.83 | 61255 | 1036897 |
| Low2 | 10.52 | 78951 | 1131502 |
| Low3 | 11.77 | 58654 | 754843 |
| Med1 | 112.78 | 786435 | 1046058 |
| Med2 | 105.19 | 837224 | 1197875 |
| Med3 | 97.48 | 488198 | 756299 |
| High1 | 203.97 | 1418622 | 1001608 |
| High2 | 218.97 | 1603009 | 1047207 |
| High3 | 215.75 | 797944 | 529832 |

2nd Set of Data on Norendoxifen

| FileName | Norendoxifen Response | ISTD Response | Response Ratio | Calculated Conc |
|---|---|---|---|---|
| 19066 | 394909 | 1631694 | 0.040 | 8.564 |
| 19142 | 259927 | 1499594 | 0.029 | −2.102 |
| 19157 | 236174 | 1567347 | 0.025 | −5.625 |
| 19175 | 303474 | 1650879 | 0.031 | −0.471 |
| 19183 | 286322 | 1485735 | 0.032 | 0.910 |
| 19198 | 285421 | 1509741 | 0.032 | 0.341 |
| 19208 | 276540 | 1620554 | 0.028 | −2.520 |
| 19278 | 296552 | 1357729 | 0.036 | 4.901 |
| 19306 | 266001 | 1273966 | 0.035 | 3.408 |
| 19309 | 174801 | 1139771 | 0.026 | −5.207 |
| 19324 | 128810 | 640489 | 0.034 | 2.215 |
| 19360 | 86290 | 458714 | 0.031 | 0.195 |
| 19384 | 78299 | 423790 | 0.031 | −0.326 |
| 19393 | 95749 | 526445 | 0.030 | −0.774 |
| 19397 | 67733 | 519145 | 0.022 | −8.771 |
| 19419 | 101553 | 680002 | 0.025 | −5.833 |
| 19443 | 62792 | 438535 | 0.024 | −6.791 |
| 19461 | 52923 | 345089 | 0.026 | −5.208 |
| 19500 | 49566 | 298820 | 0.028 | −3.262 |
| 19513 | 52689 | 327418 | 0.027 | −4.032 |
| 19539 | 54812 | 286635 | 0.032 | 0.679 |
| 20081 | 52468 | 350067 | 0.025 | −5.750 |
| 20124 | 78695 | 417502 | 0.031 | 0.254 |
| 20140 | 73246 | 371366 | 0.033 | 1.612 |
| 20160 | 26072 | 312569 | 0.014 | −16.105 |
| 20175 | 40725 | 344100 | 0.020 | −10.658 |
| 20188 | 70099 | 395249 | 0.030 | −1.477 |
| 20205 | 133509 | 799351 | 0.028 | −3.083 |
| 21436 | 105573 | 614214 | 0.029 | −2.327 |
| 21546 | 94366 | 576559 | 0.027 | −3.604 |
| 21564 | 59146 | 471390 | 0.021 | −9.549 |
| 21603 | 54821 | 319202 | 0.029 | −2.349 |
| 21630 | 60510 | 396701 | 0.025 | −5.337 |
| 21640 | 56132 | 341040 | 0.027 | −3.461 |
| 21653 | 47204 | 317333 | 0.025 | −5.925 |
| 23320 | 40993 | 290890 | 0.023 | −7.143 |
| 23339 | 20491 | 251970 | 0.014 | −16.431 |
| 23359 | 28032 | 200226 | 0.023 | −7.287 |
| 23390 | 12227 | 296939 | 0.007 | −22.698 |
| 23413 | 211515 | 1259888 | 0.028 | −2.949 |
| 23435 | 53419 | 263667 | 0.034 | 2.446 |
| 23438 | 25072 | 119561 | 0.035 | 3.548 |
| 25961 | 38335 | 315946 | 0.020 | −10.194 |
| 26081 | 48157 | 246034 | 0.033 | 1.379 |
| 26155 | 52963 | 746052 | 0.012 | −18.043 |
| 26206 | 26548 | 187122 | 0.024 | −6.995 |
| 26226 | 43686 | 258528 | 0.028 | −2.778 |
| 27064 | 48415 | 195754 | 0.041 | 9.386 |
| 27106 | 142236 | 953374 | 0.025 | −5.857 |
| 27135 | 64096 | 643672 | 0.017 | −13.584 |
| 27186 | 15662 | 159454 | 0.016 | −13.796 |
| 27224 | 28810 | 253163 | 0.019 | −11.367 |
| 27229 | 24116 | 193237 | 0.021 | −9.654 |
| QC_High_1_150506114043 | 2019214 | 1405526 | 0.239 | 189.933 |
| QC_Low_1_150506112054 | 346367 | 1391580 | 0.041 | 9.630 |
| QC_Med_1_150506113049 | 1144208 | 1372839 | 0.139 | 99.309 |
| QC_High_2 | 295558 | 291585 | 0.169 | 126.576 |
| QC_High_3 | 616664 | 396020 | 0.260 | 207.821 |
| QC_Low_2 | 103046 | 372310 | 0.046 | 13.949 |
| QC_Low_3 | 59735 | 259337 | 0.038 | 6.751 |
| QC_Med_2 | 325974 | 367929 | 0.148 | 107.274 |
| QC_Med_3 | 234615 | 392400 | 0.100 | 63.396 |
| Std_1_150506091206 | 295660 | 1439901 | 0.034 | 2.870 |
| Std_2_150506092201 | 256587 | 1378734 | 0.031 | −0.117 |
| Std_3_150506093155 | 285577 | 1349969 | 0.035 | 3.834 |
| Std_4_150506094149 | 415667 | 1443768 | 0.048 | 15.673 |
| Std_5_150506095143 | 317257 | 1315001 | 0.040 | 8.445 |
| Std_6_150506100138 | 477087 | 1361340 | 0.058 | 25.345 |
| Std_7_150506101134 | 843486 | 1415920 | 0.099 | 63.062 |
| Std_8_150506102128 | 1055968 | 1323738 | 0.133 | 93.879 |
| Std_9_150506103122 | 1310733 | 1333882 | 0.164 | 121.899 |

-continued

| | | Norendoxifen | | |
|---|---|---|---|---|
| FileName | Response | ISTD Response | Response Ratio | Calculated Conc |
| Std_10_150506104117 | 1861199 | 1339576 | 0.232 | 182.904 |
| Std_11_150506105111 | 2398059 | 1352704 | 0.295 | 239.644 |
| Std_12_150506110106 | 2913618 | 1341519 | 0.362 | 297.950 |

Endoxifen quantitation and response in patient samples.

| | Endoxifen | | |
|---|---|---|---|
| Sample ID | Calculated Conc (ng/mL) | Response | ISTD Area |
| 18768 | 0.39 | 858 | 948878 |
| 18788 | 1.70 | 15846 | 764437 |
| 18824 | 2.67 | 28234 | 793359 |
| 18837 | 4.78 | 43744 | 645545 |
| 18865 | 6.58 | 74592 | 784027 |
| 18873 | 6.51 | 80112 | 851690 |
| 18885 | 5.08 | 103654 | 1434599 |
| 20434 | NA | NF | 1524835 |
| 20478 | NA | NF | 1873595 |
| 20484 | 1.30 | 20727 | 1411744 |
| 20511 | 1.66 | 29587 | 1466708 |
| 20515 | 2.65 | 49078 | 1392281 |
| 20564 | 3.22 | 65950 | 1498317 |
| 20573 | 5.34 | 111280 | 1461115 |
| 20581 | 3.80 | 75349 | 1426339 |
| 20601 | 7.58 | 176533 | 1599850 |
| 20647 | 14.34 | 317868 | 1490262 |
| 20661 | 13.54 | 284666 | 1415658 |
| 20689 | 12.57 | 267783 | 1436705 |
| 20704 | 15.68 | 340779 | 1458681 |
| 26619 | 0.34 | 114 | 1508141 |
| 26690 | 0.34 | 134 | 1475191 |
| 26756 | 1.90 | 34462 | 1447066 |
| 26777 | 3.36 | 59301 | 1287689 |
| 26801 | 5.40 | 102120 | 1323903 |
| 26826 | 6.68 | 92705 | 959275 |
| 26837 | 0.36 | 514 | 1115449 |
| 26853 | 7.38 | 101415 | 944719 |
| 26864 | 7.57 | 90589 | 822666 |
| 26878 | 10.16 | 118857 | 794035 |
| 26936 | 2.46 | 26351 | 812995 |
| 26952 | 3.78 | 46504 | 886924 |
| 26958 | 0.34 | 105 | 744284 |
| 26978 | 4.26 | 53111 | 887541 |
| 27009 | 5.99 | 71343 | 828349 |
| 27011 | 0.66 | 4334 | 876309 |
| 27022 | 6.65 | 66263 | 689142 |
| 27045 | 1.26 | 9665 | 686202 |
| 27067 | 0.94 | 5715 | 615842 |
| 27080 | 1.36 | 12324 | 785747 |
| 27084 | 1.42 | 13202 | 798627 |
| 27413 | NA | NF | 465635 |
| 27446 | 1.29 | 9211 | 630981 |
| 27482 | 2.88 | 24964 | 643410 |
| 27526 | 7.75 | 68442 | 606397 |
| 27539 | 5.66 | 46555 | 574207 |
| 3002 | 0.35 | 81 | 466484 |
| 30031 | 1.10 | 5772 | 495349 |
| 30043 | 2.54 | 16964 | 505290 |
| 30079 | 4.20 | 29712 | 505353 |
| 30105 | 4.77 | 50235 | 743460 |
| 30116 | 5.34 | 55768 | 731395 |
| 30127 | 6.71 | 61146 | 629546 |
| 6420 | 0.41 | 1270 | 1070269 |
| 6482 | 2.62 | 39100 | 1121187 |
| 6497 | 4.72 | 77527 | 1162006 |
| 6510 | 4.39 | 47391 | 767435 |
| 6521 | 3.00 | 27958 | 687725 |
| 6535 | 7.94 | 102261 | 882954 |
| 6549 | 10.80 | 155921 | 978851 |

-continued

| | Endoxifen | | |
|---|---|---|---|
| Sample ID | Calculated Conc (ng/mL) | Response | ISTD Area |
| Std_1 | 1.13 | 12801 | 1062595 |
| Std_2 | 2.69 | 38395 | 1069320 |
| Std_3 | 4.75 | 76211 | 1132746 |
| Std_4 | 14.64 | 230116 | 1056612 |
| Std_5 | 12.13 | 210594 | 1172890 |
| Std_6 | 23.81 | 416910 | 1166491 |
| Std_7 | 59.39 | 1030203 | 1145572 |
| Std_8 | 94.50 | 1638868 | 1143017 |
| Std_9 | 117.78 | 2079955 | 1163094 |
| Std_10 | 177.17 | 2952223 | 1096393 |
| Std_11 | 248.84 | 4056331 | 1071971 |
| Std_12 | 298.59 | 5213065 | 1147835 |
| LowQC_1 | 10.20 | 155750 | 1036897 |
| LowQC_2 | 10.70 | 178553 | 1131502 |
| LowQC_3 | 8.24 | 90814 | 754843 |
| MedQC_1 | 93.72 | 1487561 | 1046058 |
| MedQC_2 | 87.15 | 1583496 | 1197875 |
| MedQC_3 | 83.55 | 958371 | 756299 |
| HighQC_1 | 200.24 | 3048922 | 1001608 |
| HighQC_2 | 200.35 | 3189428 | 1047207 |
| HighQC_3 | 206.53 | 1663579 | 529832 |

4-hydroxy Tamoxifen quantitation and response in patient samples.

| | 4-Hydroxy Tamoxifen | | |
|---|---|---|---|
| Sample ID | Calculated Conc (ng/mL) | Response | ISTD Area |
| 18768 | 0.19 | 3015 | 2399530 |
| 18788 | 0.82 | 39658 | 2014612 |
| 18824 | 0.86 | 48913 | 2359977 |
| 18837 | 1.40 | 65306 | 1789387 |
| 18865 | 1.47 | 81483 | 2110634 |
| 18873 | 1.56 | 89856 | 2177221 |
| 18885 | 0.85 | 85218 | 4167738 |
| 20434 | 0.26 | 14678 | 4442630 |
| 20478 | 0.18 | 5170 | 5585352 |
| 20484 | 0.79 | 74921 | 3980217 |
| 20511 | 0.82 | 80728 | 4131271 |
| 20515 | 1.10 | 112006 | 4017151 |
| 20564 | 1.01 | 108651 | 4297841 |
| 20573 | 1.26 | 139523 | 4297129 |
| 20581 | 0.98 | 98939 | 4068467 |
| 20601 | 1.33 | 153875 | 4442435 |
| 20647 | 2.16 | 240633 | 4086174 |
| 20661 | 2.06 | 232708 | 4153726 |
| 20689 | 1.68 | 185318 | 4128291 |
| 20704 | 1.97 | 222092 | 4174587 |
| 26619 | 0.20 | 6064 | 4244184 |
| 26690 | 0.19 | 5282 | 4016987 |
| 26756 | 0.67 | 60702 | 3942716 |
| 26777 | 0.94 | 79670 | 3447066 |
| 26801 | 1.08 | 98947 | 3623797 |
| 26826 | 1.01 | 67829 | 2695516 |
| 26837 | 0.22 | 6220 | 3050204 |
| 26853 | 1.14 | 73111 | 2526194 |

| 4-Hydroxy Tamoxifen | | | |
|---|---|---|---|
| Sample ID | Calculated Conc (ng/mL) | Response | ISTD Area |
| 26864 | 0.94 | 45419 | 1965544 |
| 26878 | 0.98 | 55858 | 2298573 |
| 26936 | 0.86 | 48390 | 2314343 |
| 26952 | 0.65 | 36142 | 2454817 |
| 26958 | 0.16 | 946 | 2226312 |
| 26978 | 0.53 | 27434 | 2440319 |
| 27009 | 0.88 | 52076 | 2421466 |
| 27011 | 0.44 | 19970 | 2351863 |
| 27022 | 1.02 | 52595 | 2073596 |
| 27045 | 0.55 | 23486 | 2023385 |
| 27067 | 0.58 | 22972 | 1835775 |
| 27080 | 0.57 | 23575 | 1895425 |
| 27084 | 0.67 | 29589 | 1927373 |
| 27413 | 0.20 | 2281 | 1631839 |
| 27446 | 0.76 | 30067 | 1668786 |
| 27482 | 1.14 | 51599 | 1775070 |
| 27526 | 1.85 | 86472 | 1741700 |
| 27539 | 1.30 | 54185 | 1611552 |
| 3002 | NA | NF | 1366983 |
| 30031 | 0.45 | 13164 | 1510509 |
| 30043 | 0.69 | 24596 | 1549683 |
| 30079 | 0.71 | 23917 | 1457036 |
| 30105 | 0.70 | 34945 | 2179008 |
| 30116 | 0.75 | 36168 | 2049184 |
| 30127 | 0.85 | 40172 | 1967785 |
| 6420 | 0.21 | 5225 | 2882321 |
| 6482 | 0.65 | 47148 | 3221437 |
| 6497 | 0.87 | 63944 | 3016193 |
| 6510 | 0.52 | 23933 | 2193645 |
| 6521 | 0.51 | 21842 | 2078718 |
| 6535 | 1.02 | 58001 | 2272084 |
| 6549 | 1.10 | 78339 | 2829487 |
| Std_1 | 0.86 | 63333 | 3061651 |
| Std_2 | 1.60 | 126439 | 2979412 |
| Std_3 | 3.09 | 273498 | 3183743 |
| Std_4 | 10.22 | 857888 | 2914286 |
| Std_5 | 8.14 | 781525 | 3347055 |
| Std_6 | 14.99 | 1460920 | 3367273 |
| Std_7 | 37.62 | 3585531 | 3271921 |
| Std_8 | 67.06 | 6043897 | 3087672 |
| Std_9 | 79.79 | 7391602 | 3171813 |
| Std_10 | 121.24 | 11120485 | 3136830 |
| Std_11 | 162.00 | 14892020 | 3141049 |
| Std_12 | 197.45 | 18470067 | 3194201 |
| LowQC_1 | 2.60 | 198332 | 2764071 |
| LowQC_2 | 2.40 | 215841 | 3282140 |
| LowQC_3 | 2.46 | 124759 | 1845395 |
| MedQC_1 | 42.35 | 3760367 | 3046944 |
| MedQC_2 | 45.77 | 4055530 | 3039643 |
| MedQC_3 | 44.83 | 2330598 | 1783433 |
| HighQC_1 | 98.45 | 7900913 | 2746235 |
| HighQC_2 | 95.55 | 8331858 | 2984061 |
| HighQC_3 | 96.85 | 4580837 | 1618676 |

N-Desmethyl-4'-Hydroxy quantitation and response in patient samples.

| N-Desmethyl-4'-Hydroxy Tam | | | |
|---|---|---|---|
| Sample ID | Calculated Conc (ng/mL) | Response | ISTD Area |
| 18768 | 0.11 | 6478 | 1418949 |
| 18788 | 0.21 | 11255 | 1246580 |
| 18824 | 0.35 | 20911 | 1409614 |
| 18837 | 0.65 | 31944 | 1156863 |
| 18865 | 1.18 | 71666 | 1432048 |
| 18873 | 1.09 | 71427 | 1542934 |
| 18885 | 1.21 | 135392 | 2638726 |
| 20434 | 0.10 | 11165 | 2633347 |
| 20478 | 0.11 | 16114 | 3369744 |
| 20484 | 0.22 | 24190 | 2554478 |
| 20511 | 0.21 | 21589 | 2429777 |
| 20515 | 0.51 | 54176 | 2518940 |
| 20564 | 0.83 | 92905 | 2629052 |
| 20573 | 0.38 | 43295 | 2681694 |
| 20581 | 0.02 | 2135 | 2579787 |
| 20601 | 0.71 | 83112 | 2763637 |
| 20647 | 1.70 | 195854 | 2715179 |
| 20661 | 1.34 | 154254 | 2699457 |
| 20689 | 1.45 | 157523 | 2552623 |
| 20704 | 1.93 | 218342 | 2659928 |
| 26619 | 0.11 | 12283 | 2716910 |
| 26690 | 0.05 | 4982 | 2542146 |
| 26756 | 0.17 | 16848 | 2385510 |
| 26777 | 0.19 | 16813 | 2133085 |
| 26801 | 0.41 | 32728 | 1894557 |
| 26826 | 0.03 | 2140 | 1727922 |
| 26837 | 0.06 | 4057 | 1662633 |
| 26853 | 0.47 | 30871 | 1544615 |
| 26864 | 0.40 | 22301 | 1322198 |
| 26878 | 0.57 | 35997 | 1484688 |
| 26936 | 0.24 | 13870 | 1392328 |
| 26952 | 0.31 | 19864 | 1512928 |
| 26958 | 0.06 | 3660 | 1460163 |
| 26978 | 0.35 | 23834 | 1593929 |
| 27009 | 0.54 | 35183 | 1530063 |
| 27011 | 0.16 | 10031 | 1519605 |
| 27022 | 0.01 | 465 | 1331431 |
| 27045 | 0.22 | 11683 | 1276177 |
| 27067 | 0.01 | 247 | 1070301 |
| 27080 | 0.44 | 21767 | 1168677 |
| 27084 | 0.58 | 29142 | 1185205 |
| 27413 | NA | NF | 939826 |
| 27446 | 0.16 | 6985 | 1007163 |
| 27482 | 0.35 | 15820 | 1061662 |
| 27526 | 0.61 | 27483 | 1065272 |
| 27539 | 0.43 | 16534 | 912845 |
| 3002 | 0.00 | 24 | 728838 |
| 30031 | 0.03 | 1048 | 831337 |
| 30043 | 0.18 | 6591 | 887422 |
| 30079 | 0.04 | 1359 | 910191 |
| 30105 | 0.70 | 43026 | 1436724 |
| 30116 | 0.80 | 47225 | 1386344 |
| 30127 | NA | NF | 1128675 |
| 6420 | 0.14 | 10059 | 1717733 |
| 6482 | 0.26 | 22674 | 2067584 |
| 6497 | 0.08 | 5571 | 1626375 |
| 6510 | 0.06 | 3541 | 1309114 |
| 6521 | 0.01 | 277 | 1436238 |
| 6535 | 0.03 | 1862 | 1366228 |
| 6549 | 0.77 | 59031 | 1799445 |
| Std_1 | 1.19 | 96247 | 1904747 |
| Std_2 | 2.26 | 190378 | 1981125 |
| Std_3 | 4.86 | 413787 | 2001224 |
| Std_4 | 15.95 | 1257807 | 1850417 |
| Std_5 | 12.19 | 1091191 | 2100153 |
| Std_6 | 23.52 | 2088988 | 2082546 |
| Std_7 | 59.49 | 5210489 | 2048907 |
| Std_8 | 99.12 | 8606656 | 2025612 |
| Std_9 | 122.57 | 10690211 | 2031234 |
| Std_10 | 172.83 | 15602263 | 2095230 |
| Std_11 | 236.95 | 21323531 | 2079609 |
| Std_12 | 305.13 | 26862139 | 2024971 |
| LowQC_1 | 10.95 | 828830 | 1776536 |
| LowQC_2 | 11.30 | 972714 | 2019974 |
| LowQC_3 | 9.88 | 487998 | 1159721 |
| MedQC_1 | 96.08 | 7621147 | 1850788 |
| MedQC_2 | 98.24 | 8103790 | 1924467 |
| MedQC_3 | 103.17 | 4505234 | 1018413 |
| HighQC_1 | 219.32 | 16710705 | 1762852 |
| HighQC_2 | 214.74 | 18007527 | 1940796 |
| HighQC_3 | 210.16 | 10408228 | 1146566 |

4'-Hydroxy Tamoxifen quantitation and response in patient samples.

| | 4'-Hydroxy Tamoxifen | | |
|---|---|---|---|
| Sample ID | Calculated Conc (ng/mL) | Response | ISTD Area |
| 18768 | 0.24 | 3363 | 2172088 |
| 18788 | 1.19 | 28281 | 1916250 |
| 18824 | 1.81 | 48728 | 2080977 |
| 18837 | 2.83 | 62234 | 1655472 |
| 18865 | 3.33 | 93441 | 2096079 |
| 18873 | 2.95 | 85399 | 2172978 |
| 18885 | 2.59 | 133675 | 3894668 |
| 20434 | 0.18 | 2811 | 4045035 |
| 20478 | 0.19 | 3758 | 5065428 |
| 20484 | 1.06 | 48506 | 3768254 |
| 20511 | 0.95 | 44050 | 3859077 |
| 20515 | 1.90 | 93981 | 3806194 |
| 20564 | 2.61 | 135079 | 3902896 |
| 20573 | 2.17 | 104172 | 3669717 |
| 20581 | 2.65 | 133250 | 3788223 |
| 20601 | 2.46 | 140885 | 4336626 |
| 20647 | 4.14 | 210537 | 3761489 |
| 20661 | 3.71 | 186268 | 3728418 |
| 20689 | 3.44 | 180034 | 3899111 |
| 20704 | 3.68 | 191393 | 3871001 |
| 26619 | 0.20 | 3694 | 4050702 |
| 26690 | 0.24 | 5417 | 3832047 |
| 26756 | 0.80 | 34425 | 3712870 |
| 26777 | 1.19 | 48068 | 3249380 |
| 26801 | 1.83 | 66555 | 2809186 |
| 26826 | 1.78 | 54590 | 2375921 |
| 26837 | 0.20 | 2306 | 2467253 |
| 26853 | 1.86 | 54910 | 2272552 |
| 26864 | 1.79 | 44228 | 1918046 |
| 26878 | 1.60 | 42925 | 2094936 |
| 26936 | 1.27 | 34702 | 2185824 |
| 26952 | 1.31 | 39922 | 2433167 |
| 26958 | NA | NF | 2339037 |
| 26978 | 1.22 | 32938 | 2163677 |
| 27009 | 1.79 | 52321 | 2255996 |
| 27011 | 0.76 | 18543 | 2137153 |
| 27022 | 1.68 | 45719 | 2117327 |
| 27045 | 1.36 | 30371 | 1779913 |
| 27067 | 2.09 | 48462 | 1770196 |
| 27080 | 1.73 | 38821 | 1737223 |
| 27084 | 1.89 | 39706 | 1622586 |
| 27413 | 0.26 | 2863 | 1567595 |
| 27446 | 0.78 | 14009 | 1553585 |
| 27482 | 1.30 | 27446 | 1686572 |
| 27526 | 2.44 | 48500 | 1505217 |
| 27539 | 1.98 | 34937 | 1353173 |
| 3002 | 0.23 | 1581 | 1130425 |
| 30031 | 0.39 | 4408 | 1249506 |
| 30043 | 1.13 | 20090 | 1446682 |
| 30079 | 1.58 | 24236 | 1201364 |
| 30105 | 1.32 | 35388 | 2136332 |
| 30116 | 0.81 | 18620 | 1974717 |
| 30127 | 1.31 | 30533 | 1863767 |
| 6420 | 0.17 | 1208 | 2562866 |
| 6482 | 0.86 | 30040 | 2947532 |
| 6497 | 1.13 | 35827 | 2567403 |
| 6510 | 0.62 | 12846 | 1902106 |
| 6521 | 0.66 | 15265 | 2072439 |
| 6535 | 1.74 | 46483 | 2067649 |
| 6549 | 2.09 | 71871 | 2626700 |
| Std_1 | 0.83 | 26072 | 2692512 |
| Std_2 | 1.63 | 57494 | 2747701 |
| Std_3 | 3.15 | 120736 | 2866766 |
| Std_4 | 10.27 | 378179 | 2673535 |
| Std_5 | 8.41 | 344843 | 2987180 |
| Std_6 | 14.49 | 607841 | 3035767 |
| Std_7 | 36.08 | 1504777 | 3007474 |
| Std_8 | 66.95 | 2652805 | 2860540 |
| Std_9 | 81.81 | 3229939 | 2852941 |
| Std_10 | 122.36 | 4801896 | 2844972 |
| Std_11 | 159.35 | 6128640 | 2797026 |
| Std_12 | 198.29 | 7827883 | 2880957 |

-continued

| | 4'-Hydroxy Tamoxifen | | |
|---|---|---|---|
| Sample ID | Calculated Conc (ng/mL) | Response | ISTD Area |
| LowQC_1 | 2.13 | 73604 | 2637536 |
| LowQC_2 | 2.20 | 79203 | 2747045 |
| LowQC_3 | 2.20 | 57019 | 1978114 |
| MedQC_1 | 37.03 | 1384891 | 2696422 |
| MedQC_2 | 39.46 | 1535649 | 2805856 |
| MedQC_3 | 37.65 | 837484 | 1603915 |
| HighQC_1 | 98.68 | 3324791 | 2437845 |
| HighQC_2 | 98.97 | 3758231 | 2747447 |
| HighQC_3 | 99.99 | 2320954 | 1679577 |

$2^{nd}$ Set of Data on 4'-Hydroxy Tamoxifen

| | 4'-Hydroxy Tamoxifen | | | |
|---|---|---|---|---|
| FileName | Calculated Conc | Response | ISTD Response | Response Ratio |
| 19066 | 0.303 | 22269 | 4453051 | 0.001 |
| 19142 | 1.579 | 94126 | 4123038 | 0.004 |
| 19157 | 1.838 | 112491 | 4252834 | 0.004 |
| 19175 | 3.419 | 215656 | 4439146 | 0.008 |
| 19183 | 1.895 | 110049 | 4037559 | 0.005 |
| 19198 | 2.053 | 121419 | 4120446 | 0.005 |
| 19208 | 1.938 | 119044 | 4274660 | 0.005 |
| 19278 | 6.753 | 391621 | 4107533 | 0.016 |
| 19306 | 6.685 | 283075 | 2998975 | 0.016 |
| 19309 | 1.328 | 51548 | 2667301 | 0.003 |
| 19324 | 5.933 | 159394 | 1901442 | 0.014 |
| 19360 | 6.746 | 108720 | 1141453 | 0.016 |
| 19384 | 3.972 | 74081 | 1315036 | 0.009 |
| 19393 | 5.312 | 91931 | 1223801 | 0.013 |
| 19397 | 1.563 | 20063 | 887271 | 0.004 |
| 19419 | 2.243 | 79687 | 2480872 | 0.005 |
| 19443 | 1.866 | 33589 | 1251374 | 0.004 |
| 19461 | 2.490 | 35518 | 998353 | 0.006 |
| 19500 | 2.593 | 28876 | 779966 | 0.006 |
| 19513 | 2.550 | 36568 | 1004244 | 0.006 |
| 19539 | 1.572 | 19542 | 859341 | 0.004 |
| 20081 | 0.586 | 8058 | 901020 | 0.001 |
| 20124 | 1.781 | 31939 | 1244689 | 0.004 |
| 20140 | 1.899 | 30547 | 1118830 | 0.005 |
| 20160 | 1.828 | 24689 | 937980 | 0.004 |
| 20175 | 1.554 | 19421 | 863716 | 0.004 |
| 20188 | 1.898 | 32090 | 1175536 | 0.005 |
| 20205 | 2.902 | 85174 | 2060234 | 0.007 |
| 21436 | 0.117 | 4844 | 2021993 | 0.000 |
| 21546 | 1.348 | 28821 | 1470305 | 0.003 |
| 21564 | 2.889 | 59191 | 1437790 | 0.007 |
| 21603 | 2.569 | 36899 | 1006018 | 0.006 |
| 21630 | 4.485 | 58183 | 915834 | 0.011 |
| 21640 | 4.175 | 61789 | 1044008 | 0.010 |
| 21653 | 2.931 | 31548 | 755613 | 0.007 |
| 23320 | 0.548 | 5803 | 689039 | 0.001 |
| 23339 | 1.272 | 19300 | 1041074 | 0.003 |
| 23359 | 2.257 | 21560 | 667047 | 0.005 |
| 23390 | 1.908 | 12775 | 465563 | 0.005 |
| 23413 | 2.272 | 151070 | 4644733 | 0.005 |
| 23435 | 2.232 | 19746 | 617606 | 0.005 |
| 23438 | 1.798 | 12771 | 493301 | 0.004 |
| 25961 | 0.253 | 4401 | 1024904 | 0.001 |
| 26081 | −0.023 | 275 | 622530 | 0.000 |
| 26155 | 0.064 | 1040 | 630132 | 0.000 |
| 26206 | 0.544 | 4554 | 544708 | 0.001 |
| 26226 | 0.210 | 3536 | 955368 | 0.001 |
| 27064 | 0.026 | 629 | 557421 | 0.000 |
| 27106 | 1.523 | 21251 | 964060 | 0.004 |
| 27135 | 1.867 | 35016 | 1303640 | 0.004 |
| 27186 | 2.309 | 153437 | 4642861 | 0.006 |
| 27224 | 2.862 | 35270 | 864675 | 0.007 |
| 27229 | 2.767 | 17985 | 455820 | 0.007 |
| QC_High_1_150506114043 | 83.229 | 4597542 | 3825262 | 0.200 |
| QC_Low_1_150506112054 | 2.664 | 140705 | 3701906 | 0.006 |

4'-Hydroxy Tamoxifen

| FileName | Calculated Conc | Response | ISTD Response | Response Ratio |
|---|---|---|---|---|
| QC_Med_1_150506113049 | 37.743 | 1894768 | 3535619 | 0.089 |
| QC_High_2 | 88.423 | 1031519 | 806248 | 0.213 |
| QC_High_3 | 97.226 | 1330667 | 942761 | 0.235 |
| QC_Low_2 | 5.388 | 77980 | 1023477 | 0.013 |
| QC_Low_3 | 3.554 | 30997 | 613995 | 0.008 |
| QC_Med_2 | 36.281 | 601572 | 1168351 | 0.086 |
| QC_Med_3 | 38.465 | 558288 | 1021937 | 0.091 |
| Std_1_150506091206 | 0.731 | 41595 | 3790363 | 0.002 |
| Std_2_150506092201 | 1.540 | 83002 | 3723933 | 0.004 |
| Std_3_150506093155 | 3.449 | 170169 | 3472544 | 0.008 |
| Std_4_150506094149 | 9.368 | 510688 | 3865765 | 0.022 |
| Std_5_150506095143 | 8.242 | 408166 | 3510555 | 0.019 |
| Std_6_150506100138 | 17.558 | 884480 | 3570164 | 0.041 |
| Std_7_150506101134 | 38.848 | 2115043 | 3832867 | 0.092 |
| Std_8_150506102128 | 65.521 | 3179778 | 3383142 | 0.157 |
| Std_9_150506103122 | 81.313 | 4019062 | 3425228 | 0.196 |
| Std_10_150506104117 | 116.630 | 5995135 | 3515037 | 0.284 |
| Std_11_150506105111 | 156.899 | 8071959 | 3465385 | 0.388 |
| Std_12_150506110106 | 203.503 | 10317099 | 3356583 | 0.512 |

N-Desmethyl Tamoxifen quantitation and response in patient samples.

N-Desmethyl Tamoxifen

| Sample ID | Calculated Conc (ng/mL) | Response | ISTD Area |
|---|---|---|---|
| 18768 | 0.45 | 9391 | 7013663 |
| 18788 | 4.72 | 997637 | 5658276 |
| 18824 | 6.28 | 1289400 | 5370746 |
| 18837 | 10.69 | 2081686 | 4945768 |
| 18865 | 13.75 | 3224539 | 5904185 |
| 18873 | 16.85 | 3287990 | 4885497 |
| 18885 | 10.42 | 6162583 | 15037937 |
| 20434 | 0.44 | 13754 | 14973184 |
| 20478 | 0.43 | 11994 | 19567366 |
| 20484 | 3.20 | 1640706 | 14365887 |
| 20511 | 3.53 | 1826641 | 14327269 |
| 20515 | 6.01 | 3287099 | 14345893 |
| 20564 | 7.67 | 4371978 | 14704733 |
| 20573 | 7.68 | 4103602 | 13787594 |
| 20581 | 7.93 | 4120139 | 13386871 |
| 20601 | 9.88 | 5544877 | 14310077 |
| 20647 | 17.73 | 9200162 | 12971400 |
| 20661 | 16.29 | 9061736 | 13940923 |
| 20689 | 14.58 | 7719066 | 13305153 |
| 20704 | 16.47 | 8717935 | 13260540 |
| 26619 | 0.42 | 2117 | 11009897 |
| 26690 | 0.41 | 476 | 13027769 |
| 26756 | 2.22 | 863574 | 11677656 |
| 26777 | 3.32 | 1080841 | 9084409 |
| 26801 | 5.08 | 1508009 | 7900022 |
| 26826 | 5.31 | 1381666 | 6897386 |
| 26837 | 0.43 | 3833 | 6334347 |
| 26853 | 5.69 | 1098479 | 5081545 |
| 26864 | 6.05 | 1179428 | 5108144 |
| 26878 | 6.60 | 1541585 | 6084624 |
| 26936 | 3.81 | 836363 | 6017575 |
| 26952 | 3.48 | 913220 | 7282434 |
| 26958 | 0.43 | 3622 | 5877387 |
| 26978 | 4.29 | 1042266 | 6573581 |
| 27009 | 6.17 | 1529707 | 6486246 |
| 27011 | 2.03 | 380969 | 5767996 |
| 27022 | 5.78 | 1236685 | 5625116 |
| 27045 | 3.84 | 739878 | 5267957 |
| 27067 | 4.82 | 1030933 | 5713837 |
| 27080 | 5.66 | 1169780 | 5447403 |
| 27084 | 7.11 | 1364187 | 4971917 |
| 27413 | 0.42 | 1108 | 4253160 |
| 27446 | 1.98 | 324056 | 5043427 |
| 27482 | 3.77 | 601493 | 4375000 |

N-Desmethyl Tamoxifen

| Sample ID | Calculated Conc (ng/mL) | Response | ISTD Area |
|---|---|---|---|
| 27526 | 8.09 | 1379832 | 4387718 |
| 27539 | 6.35 | 1054868 | 4342974 |
| 3002 | 0.42 | 646 | 3952111 |
| 30031 | 1.91 | 235647 | 3844766 |
| 30043 | 3.87 | 551445 | 3901710 |
| 30079 | 5.32 | 748541 | 3728783 |
| 30105 | 6.47 | 1529920 | 6170754 |
| 30116 | 7.07 | 1516184 | 5559182 |
| 30127 | 8.18 | 1836861 | 5779548 |
| 6420 | 0.60 | 65522 | 8832583 |
| 6482 | 4.04 | 1193657 | 8036794 |
| 6497 | 6.87 | 2044396 | 7727684 |
| 6510 | 5.49 | 1336093 | 6433864 |
| 6521 | 3.69 | 886207 | 6614396 |
| 6535 | 9.40 | 2555509 | 6943069 |
| 6549 | 11.01 | 3043467 | 7012004 |
| Std_1 | 5.31 | 2327253 | 11617390 |
| Std_2 | 9.97 | 4708014 | 12033677 |
| Std_3 | 19.38 | 9375981 | 12070965 |
| Std_4 | 61.49 | 27754533 | 11094301 |
| Std_5 | 49.86 | 25321926 | 12503328 |
| Std_6 | 100.46 | 49441618 | 12062805 |
| Std_7 | 237.72 | 122201199 | 12562079 |
| Std_8 | 399.25 | 210842807 | 12886373 |
| Std_9 | 527.12 | 256541351 | 11865614 |
| Std_10 | 744.46 | 358614050 | 11729628 |
| Std_11 | 986.35 | 456157172 | 11246764 |
| Std_12 | 1256.13 | 543500909 | 10507976 |
| LowQC_1 | 41.15 | 17191778 | 10304237 |
| LowQC_2 | 40.50 | 15299115 | 9318490 |
| LowQC_3 | 41.88 | 8361785 | 4924263 |
| MedQC_1 | 184.96 | 82256696 | 10876149 |
| MedQC_2 | 176.73 | 62369080 | 8631562 |
| MedQC_3 | 209.89 | 42232054 | 4918806 |
| HighQC_1 | 750.34 | 301780826 | 9793035 |
| HighQC_2 | 724.44 | 245346920 | 8247495 |
| HighQC_3 | 735.41 | 155798565 | 5158860 |

2$^{nd}$ set data on N-desmethyl tamoxifen

N-Desmethyl Tamoxifen

| FileName | Calculated Conc | Response | ISTD Response | Response Ratio |
|---|---|---|---|---|
| 19066 | 2.065 | 1893566 | 17801219 | 0.018 |
| 19142 | 5.193 | 3804551 | 16024676 | 0.040 |
| 19157 | 5.814 | 4318122 | 16392626 | 0.044 |
| 19175 | 15.766 | 10576421 | 15542009 | 0.113 |
| 19183 | 6.688 | 4269419 | 14229706 | 0.050 |
| 19198 | 8.157 | 5383057 | 14886974 | 0.060 |
| 19208 | 5.735 | 3583739 | 13778023 | 0.043 |
| 19278 | 23.120 | 15673119 | 15850368 | 0.165 |
| 19306 | 27.789 | 11650590 | 9834496 | 0.197 |
| 19309 | 6.095 | 1976544 | 7182395 | 0.046 |
| 19324 | 19.251 | 3793229 | 4588877 | 0.138 |
| 19360 | 24.238 | 4034751 | 3895645 | 0.173 |
| 19384 | 19.202 | 3353221 | 4066704 | 0.137 |
| 19393 | 17.748 | 3052769 | 3998016 | 0.127 |
| 19397 | 4.674 | 678296 | 3144886 | 0.036 |
| 19419 | 5.292 | 846685 | 3505013 | 0.040 |
| 19443 | 5.792 | 838732 | 3195069 | 0.044 |
| 19461 | 7.933 | 1017100 | 2887748 | 0.059 |
| 19500 | 9.755 | 1273539 | 2971638 | 0.071 |
| 19513 | 8.469 | 1110230 | 2963301 | 0.062 |
| 19539 | 9.135 | 1132214 | 2812449 | 0.067 |
| 20081 | 2.233 | 330630 | 2915326 | 0.019 |
| 20124 | 5.001 | 720772 | 3142098 | 0.038 |
| 20140 | 5.948 | 944581 | 3510755 | 0.045 |
| 20160 | 7.198 | 913531 | 2842164 | 0.054 |
| 20175 | 7.559 | 1028737 | 3056595 | 0.056 |
| 20188 | 8.153 | 1243431 | 3440186 | 0.060 |

-continued

N-Desmethyl Tamoxifen

| FileName | Calculated Conc | Response | ISTD Response | Response Ratio |
|---|---|---|---|---|
| 20205 | 8.805 | 2379243 | 6120056 | 0.065 |
| 21436 | −0.161 | 82557 | 6275244 | 0.002 |
| 21546 | 5.755 | 1093811 | 4191694 | 0.043 |
| 21564 | 11.340 | 2276511 | 4599180 | 0.082 |
| 21603 | 8.428 | 1177190 | 3156499 | 0.062 |
| 21630 | 13.598 | 1742557 | 2955369 | 0.098 |
| 21640 | 11.957 | 1582178 | 3037601 | 0.087 |
| 21653 | 11.957 | 1155197 | 2217912 | 0.087 |
| 23320 | 2.693 | 317766 | 2394849 | 0.022 |
| 23339 | 3.836 | 487883 | 2701690 | 0.030 |
| 23359 | 6.647 | 782831 | 2623922 | 0.050 |
| 23390 | 5.517 | 428388 | 1706743 | 0.042 |
| 23413 | 7.243 | 5505399 | 17027960 | 0.054 |
| 23435 | 4.842 | 378474 | 1699292 | 0.037 |
| 23438 | 4.856 | 245223 | 1098217 | 0.037 |
| 25961 | −0.352 | 17773 | 3444979 | 0.001 |
| 26081 | −0.428 | 4928 | 2536463 | 0.000 |
| 26155 | −0.435 | 3436 | 2053149 | 0.000 |
| 26206 | −0.421 | 4116 | 1814687 | 0.000 |
| 26226 | −0.300 | 21248 | 2901877 | 0.001 |
| 27064 | −0.439 | 2871 | 1935606 | 0.000 |
| 27106 | 4.249 | 1742409 | 8806092 | 0.033 |
| 27135 | 4.598 | 555198 | 2612748 | 0.035 |
| 27186 | 6.489 | 517740 | 1774796 | 0.049 |
| 27224 | 9.361 | 728755 | 1768581 | 0.069 |
| 27229 | 7.278 | 668537 | 2058499 | 0.054 |
| QC_High_1_150506114043 | 660.452 | 435185890 | 15447019 | 4.695 |
| QC_Low_1_150506112054 | 41.893 | 28271647 | 15914440 | 0.296 |
| QC_Med_1_150506113049 | 176.768 | 110777325 | 14852088 | 1.243 |
| QC_High_2 | 666.689 | 82150225 | 2888204 | 4.741 |
| QC_High_3 | 750.310 | 97111711 | 3027264 | 5.347 |
| QC_Low_2 | 59.321 | 7953162 | 3170574 | 0.418 |
| QC_Low_3 | 42.049 | 3274694 | 1836588 | 0.297 |
| QC_Med_2 | 188.111 | 27973649 | 3523808 | 1.323 |
| QC_Med_3 | 207.865 | 23539310 | 2682660 | 1.462 |
| Std_1_150506091206 | 4.715 | 3382129 | 15558800 | 0.036 |
| Std_2_150506092201 | 10.198 | 6944239 | 15530643 | 0.075 |
| Std_3_150506093155 | 20.520 | 13113426 | 14905147 | 0.147 |
| Std_4_150506094149 | 61.006 | 41603966 | 16130492 | 0.430 |
| Std_5_150506095143 | 52.335 | 33708040 | 15218576 | 0.369 |
| Std_6_150506100138 | 100.981 | 64831809 | 15215929 | 0.710 |
| Std_7_150506101134 | 239.435 | 164606137 | 16277076 | 1.685 |
| Std_8_150506102128 | 400.008 | 254165419 | 14991752 | 2.826 |
| Std_9_150506103122 | 512.940 | 315263074 | 14461814 | 3.633 |
| Std_10_150506104117 | 751.782 | 473125498 | 14719297 | 5.357 |
| Std_11_150506105111 | 989.021 | 602805977 | 14168882 | 7.091 |
| Std_12_150506110106 | 1254.549 | 755234278 | 13899320 | 9.056 |

Tamoxifen quantitation and response in patient samples.

Tamoxifen

| Sample ID | Calculated Conc (ng/mL) | Response | ISTD Area |
|---|---|---|---|
| 18768 | 0.19 | 11350 | 8657179 |
| 18788 | 64.52 | 2071277 | 6179811 |
| 18824 | 75.45 | 2323692 | 5927027 |
| 18837 | 118.82 | 3493130 | 5650329 |
| 18865 | 134.03 | 4231612 | 6064968 |
| 18873 | 125.15 | 4035948 | 6196900 |
| 18885 | 54.09 | 5012052 | 17841365 |
| 20434 | 0.25 | 29490 | 17918878 |
| 20478 | 0.05 | 15176 | 24669280 |
| 20484 | 39.16 | 3465206 | 17038973 |
| 20511 | 51.28 | 4521960 | 16978931 |
| 20515 | 58.91 | 5194907 | 16978612 |
| 20564 | 62.95 | 5586963 | 17086731 |
| 20573 | 71.94 | 6062564 | 16221260 |
| 20581 | 58.71 | 4699760 | 15412475 |
| 20601 | 78.44 | 6699955 | 16436717 |
| 20647 | 137.89 | 10249638 | 14278153 |

-continued

Tamoxifen

| Sample ID | Calculated Conc (ng/mL) | Response | ISTD Area |
|---|---|---|---|
| 20661 | 106.10 | 9245452 | 16755833 |
| 20689 | 90.43 | 7455218 | 15860377 |
| 20704 | 116.51 | 9830326 | 16218100 |
| 26619 | 0.07 | 10074 | 14455436 |
| 26690 | 0.18 | 20386 | 15879616 |
| 26756 | 34.95 | 2383129 | 13131665 |
| 26777 | 44.56 | 2534522 | 10951927 |
| 26801 | 63.56 | 2682884 | 8125969 |
| 26826 | 48.06 | 1933458 | 7746196 |
| 26837 | 0.29 | 12406 | 6671459 |
| 26853 | 54.28 | 1547378 | 5488947 |
| 26864 | 55.06 | 1556148 | 5441919 |
| 26878 | 41.41 | 1545348 | 7185485 |
| 26936 | 40.27 | 1394728 | 6669012 |
| 26952 | 27.71 | 1107256 | 7694108 |
| 26958 | 0.33 | 16221 | 7897622 |
| 26978 | 19.13 | 754743 | 7589060 |
| 27009 | 50.25 | 1927906 | 7387061 |
| 27011 | 36.56 | 1358366 | 7154478 |
| 27022 | 49.21 | 1655736 | 6478414 |
| 27045 | 48.06 | 1561893 | 6258393 |
| 27067 | 49.26 | 1517871 | 5933913 |
| 27080 | 48.76 | 1474533 | 5822771 |
| 27084 | 40.15 | 1262719 | 6055936 |
| 27413 | 0.25 | 8576 | 5300227 |
| 27446 | 26.64 | 793351 | 5733720 |
| 27482 | 38.93 | 1066943 | 5277298 |
| 27526 | 65.81 | 1659523 | 4854108 |
| 27539 | 66.06 | 1601415 | 4666695 |
| 3002 | 0.26 | 7653 | 4493100 |
| 30031 | 12.60 | 296745 | 4522346 |
| 30043 | 30.38 | 776495 | 4921844 |
| 30079 | 33.53 | 811130 | 4658023 |
| 30105 | 26.33 | 941949 | 6886006 |
| 30116 | 20.53 | 705407 | 6611936 |
| 30127 | 36.97 | 1165680 | 6071292 |
| 6420 | 0.61 | 36915 | 10553272 |
| 6482 | 18.90 | 991389 | 10091984 |
| 6497 | 33.76 | 1545743 | 8815779 |
| 6510 | 18.08 | 687863 | 7318004 |
| 6521 | 14.28 | 572749 | 7707224 |
| 6535 | 56.47 | 2235005 | 7619942 |
| 6549 | 60.89 | 2473508 | 7820955 |
| Std_1 | 5.07 | 368746 | 13870144 |
| Std_2 | 9.87 | 743436 | 14447818 |
| Std_3 | 20.91 | 1577523 | 14518514 |
| Std_4 | 61.61 | 4389679 | 13716703 |
| Std_5 | 50.98 | 3886987 | 14681961 |
| Std_6 | 98.50 | 7499571 | 14642835 |
| Std_7 | 232.22 | 18185150 | 14991747 |
| Std_8 | 401.17 | 31914385 | 15135753 |
| Std_9 | 504.67 | 38342009 | 14399860 |
| Std 10 | 761.87 | 53303371 | 13136206 |
| Std_11 | 1028.75 | 70717814 | 12781973 |
| Std_12 | 1221.75 | 91208237 | 13784726 |
| LowQC_1 | 37.88 | 2612589 | 13281768 |
| LowQC_2 | 37.79 | 2103909 | 10721385 |
| LowQC_3 | 39.37 | 1299297 | 6355004 |
| MedQC_1 | 195.63 | 12368756 | 12119500 |
| MedQC_2 | 208.87 | 9917798 | 9097656 |
| MedQC_3 | 192.21 | 6176283 | 6160378 |
| HighQC_1 | 753.79 | 47482016 | 11830479 |
| HighQC_2 | 783.21 | 37796034 | 9053718 |
| HighQC_3 | 792.09 | 22732114 | 5382465 |

2nd Set of Data on Tamoxifen

Tamoxifen

| FileName | Calculated Conc | Response | ISTD Response | Response Ratio |
|---|---|---|---|---|
| 19066 | 3.701 | 535351 | 21932598 | 0.004 |
| 19142 | 46.038 | 4826863 | 18743658 | 0.043 |
| 19157 | 42.676 | 4468571 | 18698711 | 0.040 |
| 19175 | 70.899 | 7177323 | 18180212 | 0.066 |
| 19183 | 40.556 | 3795801 | 16700119 | 0.038 |
| 19198 | 50.601 | 4877479 | 17253561 | 0.047 |
| 19208 | 48.961 | 4130546 | 15094531 | 0.046 |
| 19278 | 112.000 | 10718988 | 17223765 | 0.104 |
| 19306 | 109.572 | 7039806 | 11562039 | 0.101 |
| 19309 | 12.404 | 588320 | 8141233 | 0.012 |
| 19324 | 116.499 | 3251398 | 5023090 | 0.108 |
| 19360 | 115.255 | 2918929 | 4558052 | 0.107 |
| 19384 | 69.683 | 1852847 | 4774541 | 0.065 |
| 19393 | 93.264 | 2389964 | 4609258 | 0.086 |
| 19397 | 58.819 | 1228203 | 3743936 | 0.055 |
| 19419 | 64.295 | 1435152 | 4005502 | 0.060 |
| 19443 | 65.809 | 1333605 | 3637172 | 0.061 |
| 19461 | 76.288 | 1478646 | 3482622 | 0.071 |
| 19500 | 76.305 | 1542766 | 3632836 | 0.071 |
| 19513 | 68.110 | 1283532 | 3383306 | 0.063 |
| 19539 | 45.479 | 803096 | 3156336 | 0.042 |
| 20081 | 32.732 | 624362 | 3390153 | 0.031 |
| 20124 | 48.263 | 1018603 | 3775475 | 0.045 |
| 20140 | 68.004 | 1470256 | 3881451 | 0.063 |
| 20160 | 64.933 | 1272861 | 3517926 | 0.060 |
| 20175 | 75.348 | 1428138 | 3405371 | 0.070 |
| 20188 | 89.929 | 2033491 | 4066576 | 0.083 |
| 20205 | 70.704 | 2541456 | 6455164 | 0.066 |
| 21436 | 1.476 | 85028 | 6980140 | 0.002 |
| 21546 | 48.585 | 1345694 | 4955204 | 0.045 |
| 21564 | 95.890 | 2607984 | 4892543 | 0.089 |
| 21603 | 63.763 | 1355947 | 3815715 | 0.059 |
| 21630 | 84.113 | 1611409 | 3444209 | 0.078 |
| 21640 | 82.497 | 1572414 | 3426332 | 0.076 |
| 21653 | 50.235 | 829879 | 2956721 | 0.047 |
| 23320 | 40.814 | 567630 | 2481819 | 0.038 |
| 23339 | 56.680 | 920885 | 2911936 | 0.053 |
| 23359 | 82.388 | 947509 | 2067360 | 0.076 |
| 23390 | 56.566 | 728329 | 2307661 | 0.053 |
| 23413 | 62.246 | 4437177 | 12788110 | 0.058 |
| 23435 | 39.294 | 493294 | 2238856 | 0.037 |
| 23438 | 38.475 | 344868 | 1597971 | 0.036 |
| 25961 | 0.037 | 17722 | 4142657 | 0.001 |
| 26081 | −0.254 | 6716 | 2510216 | 0.000 |
| 26155 | −0.439 | 4001 | 2413366 | 0.000 |
| 26206 | 0.050 | 11022 | 2534035 | 0.001 |
| 26226 | −0.200 | 14415 | 4846489 | 0.000 |
| 27064 | −0.023 | 9656 | 2445806 | 0.001 |
| 27106 | 42.931 | 2980808 | 12399985 | 0.040 |
| 27135 | 50.710 | 917164 | 3237516 | 0.047 |
| 27186 | 52.669 | 544080 | 1849951 | 0.049 |
| 27224 | 69.349 | 849916 | 2200587 | 0.064 |
| 27229 | 43.288 | 561047 | 2314994 | 0.040 |
| QC_High_1_150506114043 | 665.297 | 75125747 | 19977315 | 0.627 |
| QC_Low_1_150506112054 | 42.707 | 4685691 | 19592959 | 0.040 |
| QC_Med_1_150506113049 | 191.494 | 19331542 | 18158006 | 0.177 |
| QC_High_2 | 702.467 | 14501479 | 3646902 | 0.663 |
| QC_High_3 | 693.744 | 14196581 | 3616342 | 0.654 |
| QC_Low_2 | 56.305 | 1102329 | 3508672 | 0.052 |
| QC_Low_3 | 44.334 | 546776 | 2203665 | 0.041 |
| QC_Med_2 | 195.004 | 4267239 | 3935737 | 0.181 |
| QC_Med_3 | 231.177 | 3406054 | 2647533 | 0.214 |
| Std_1_150506091206 | 4.730 | 590077 | 19625944 | 0.005 |
| Std_2_150506092201 | 10.057 | 1163202 | 19597467 | 0.010 |
| Std_3_150506093155 | 20.691 | 2175560 | 18458380 | 0.020 |
| Std_4_150506094149 | 57.908 | 6569960 | 20338991 | 0.054 |
| Std_5_150506095143 | 52.677 | 5527146 | 18790321 | 0.049 |
| Std_6_150506100138 | 104.641 | 10935888 | 18805047 | 0.097 |
| Std_7_150506101134 | 240.132 | 26496831 | 19823070 | 0.223 |
| Std_8_150506102128 | 403.963 | 42234460 | 18680230 | 0.377 |
| Std_9_150506103122 | 521.039 | 53364854 | 18220106 | 0.488 |
| Std_10_150506104117 | 745.879 | 78023680 | 18448605 | 0.705 |
| Std_11_150506105111 | 957.878 | 98106705 | 17914330 | 0.913 |
| Std_12_150506110106 | 1277.813 | 136400695 | 18438987 | 1.233 |

Patient Data Summary

| Sample ID # | Tamoxifen | N-DM-Tamoxifen | N-DM-4'-OH-Tamoxifen | Endoxifen | Norendoxifen | 4-OH-Tamoxifen | 4'-OH-Tamoxifen |
|---|---|---|---|---|---|---|---|
| 19066 | 3.701 | 2.065 | 0.766 | 1.391 | 8.564 | 0.332 | 0.303 |
| 19142 | 46.038 | 5.193 | 0.916 | 4.316 | −2.102 | 1.047 | 1.579 |
| 19157 | 42.676 | 5.814 | 0.831 | 5.240 | −5.625 | 1.054 | 1.838 |
| 19175 | 70.899 | 15.766 | 2.934 | 26.761 | −0.471 | 1.779 | 3.419 |
| 19183 | 40.556 | 6.688 | 1.480 | 6.161 | 0.910 | 1.378 | 1.895 |
| 19198 | 50.601 | 8.157 | 1.345 | 6.282 | 0.341 | 1.217 | 2.053 |
| 19208 | 48.961 | 5.735 | 0.691 | 6.009 | −2.520 | 0.753 | 1.938 |
| 19278 | 112.000 | 23.120 | 4.595 | 39.457 | 4.901 | 2.840 | 6.753 |
| 19306 | 109.572 | 27.789 | 5.282 | 37.314 | 3.408 | 3.227 | 6.685 |
| 19309 | 12.404 | 6.095 | 1.611 | 3.442 | −5.207 | 0.765 | 1.328 |
| 19324 | 116.499 | 19.251 | 4.073 | 35.628 | 2.215 | 2.209 | 5.933 |
| 19360 | 115.255 | 24.238 | 4.243 | 44.038 | 0.195 | 2.461 | 6.746 |
| 19384 | 69.683 | 19.202 | 3.648 | 37.655 | −0.326 | 1.757 | 3.972 |
| 19393 | 93.264 | 17.748 | 2.821 | 35.239 | −0.774 | 1.565 | 5.312 |
| 19397 | 58.819 | 4.674 | 0.193 | 5.816 | −8.771 | 1.414 | 1.563 |
| 19419 | 64.295 | 5.292 | 0.194 | 7.615 | −5.833 | 1.386 | 2.243 |
| 19443 | 65.809 | 5.792 | 0.251 | 8.806 | −6.791 | 1.407 | 1.866 |
| 19461 | 76.288 | 7.933 | 0.467 | 12.942 | −5.208 | 1.592 | 2.490 |
| 19500 | 76.305 | 9.755 | 0.569 | 15.373 | −3.262 | 1.611 | 2.593 |
| 19513 | 68.110 | 8.469 | 0.692 | 16.571 | −4.032 | 1.350 | 2.550 |
| 19539 | 45.479 | 9.135 | 0.760 | 17.872 | 0.679 | 1.142 | 1.572 |
| 20081 | 32.732 | 2.233 | 0.296 | 2.256 | −5.750 | 0.447 | 0.586 |
| 20124 | 48.263 | 5.001 | 0.518 | 4.950 | 0.254 | 1.023 | 1.781 |
| 20140 | 68.004 | 5.948 | 0.494 | 7.486 | 1.612 | 0.996 | 1.899 |
| 20160 | 64.933 | 7.198 | 0.477 | 8.130 | −16.105 | 0.868 | 1.828 |
| 20175 | 75.348 | 7.559 | 0.634 | 8.067 | −10.658 | 0.645 | 1.554 |
| 20188 | 89.929 | 8.153 | 0.847 | 10.347 | −1.477 | 1.275 | 1.898 |
| 20205 | 70.704 | 8.805 | 0.660 | 8.673 | −3.083 | 0.855 | 2.902 |

-continued

| Sample ID # | Tamoxifen | N-DM-Tamoxifen | N-DM-4'-OH-Tamoxifen | Endoxifen | Norendoxifen | 4-OH-Tamoxifen | 4'-OH-Tamoxifen |
|---|---|---|---|---|---|---|---|
| 21436 | 1.476 | −0.161 | −0.119 | 0.085 | −2.327 | 0.075 | 0.117 |
| 21546 | 48.585 | 5.755 | 0.213 | 1.539 | −3.604 | 0.371 | 1.348 |
| 21564 | 95.890 | 11.340 | 0.705 | 3.078 | −9.549 | 0.658 | 2.889 |
| 21603 | 63.763 | 8.428 | 0.655 | 2.686 | −2.349 | 0.546 | 2.569 |
| 21630 | 84.113 | 13.598 | 1.362 | 4.806 | −5.337 | 0.615 | 4.485 |
| 21640 | 82.497 | 11.957 | 1.328 | 3.512 | −3.461 | 0.600 | 4.175 |
| 21653 | 50.235 | 11.957 | 1.349 | 3.711 | −5.925 | 0.688 | 2.931 |
| 23320 | 40.814 | 2.693 | 0.290 | 0.784 | −7.143 | 0.646 | 0.548 |
| 23339 | 56.680 | 3.836 | −0.075 | 3.599 | −16.431 | 0.917 | 1.272 |
| 23359 | 82.388 | 6.647 | 0.278 | 5.589 | −7.287 | 1.174 | 2.257 |
| 23390 | 56.566 | 5.517 | 0.254 | 4.420 | −22.698 | 1.011 | 1.908 |
| 23413 | 62.246 | 7.243 | 0.584 | 6.938 | −2.949 | 0.976 | 2.272 |
| 23435 | 39.294 | 4.842 | 0.390 | 4.922 | 2.446 | 0.571 | 2.232 |
| 23438 | 38.475 | 4.856 | 0.431 | 5.276 | 3.548 | 0.655 | 1.798 |
| 25961 | 0.037 | −0.352 | −0.108 | 0.072 | −10.194 | 0.075 | 0.253 |
| 26081 | −0.254 | −0.428 | −0.133 | 0.063 | 1.379 | 0.023 | −0.023 |
| 26155 | −0.439 | −0.435 | −0.163 | NA | −18.043 | 0.001 | 0.064 |
| 26206 | 0.050 | −0.421 | −0.083 | 0.015 | −6.995 | 0.062 | 0.544 |
| 26226 | −0.200 | −0.300 | −0.150 | NA | −2.778 | 0.054 | 0.210 |
| 27064 | −0.023 | −0.439 | −0.122 | 0.013 | 9.386 | 0.056 | 0.026 |
| 27106 | 42.931 | 4.249 | 0.148 | 4.712 | −5.857 | 1.267 | 1.523 |
| 27135 | 50.710 | 4.598 | 0.264 | 5.862 | −13.584 | 0.958 | 1.867 |
| 27186 | 52.669 | 6.489 | 0.189 | 7.137 | −13.796 | 0.874 | 2.309 |
| 27224 | 69.349 | 9.361 | 0.934 | 14.139 | −11.367 | 1.390 | 2.862 |
| 27229 | 43.288 | 7.278 | 0.562 | 12.816 | −9.654 | 1.055 | 2.767 |

Example 5: Additional Clinical Quantitation and Response Study

The standard operating protocol of Examples 1-3 were used to quantitate tamoxifen and its metabolites in patient samples and were correlated to tamoxifen response.

4'-Hydroxy Tamoxifen

| | 4'-Hydroxy Tamoxifen | | | | | | | |
|---|---|---|---|---|---|---|---|---|
| Sample ID | Specified Conc | % Diff | Calculated Conc | Level | Response | ISTD Response | Response Ratio | RT |
| Std_1 | 0.800 | −19 | 0.650 | 1 | 18875 | 2072069 | 0.002 | 3.3169 |
| Std_2 | 1.600 | 4 | 1.671 | 2 | 51081 | 2234410 | 0.004 | 3.3316 |
| Std_3 | 3.200 | 21 | 3.866 | 3 | 113684 | 2168822 | 0.009 | 3.3309 |
| Std_4 | 10.000 | −11 | 8.924 | 4 | 271360 | 2253046 | 0.020 | 3.3313 |
| Std_5 | 8.000 | 4 | 8.305 | 5 | 256942 | 2291669 | 0.019 | 3.3313 |
| Std_6 | 16.000 | 0 | 15.936 | 6 | 476695 | 2221478 | 0.036 | 3.3310 |
| Std_7 | 40.000 | −3 | 38.805 | 7 | 1195727 | 2297958 | 0.087 | 3.3309 |
| Std_8 | 64.000 | 4 | 66.462 | 8 | 1978710 | 2229656 | 0.148 | 3.3314 |
| Std_9 | 80.000 | 6 | 84.720 | 9 | 2500818 | 2216656 | 0.188 | 3.3313 |
| Std_10 | 120.000 | −10 | 108.549 | 10 | 3532184 | 2452070 | 0.240 | 3.3313 |
| Std_11 | 160.000 | 4 | 166.177 | 11 | 5013004 | 2292376 | 0.364 | 3.3309 |
| Std_12 | 200.000 | 0 | 199.566 | 12 | 6005444 | 2297913 | 0.436 | 3.3310 |
| QC_Low_1 | 2.000 | 26 | 2.528 | 1 Low | 79820 | 2304249 | 0.006 | 3.3026 |
| QC_Low_2 | 2.000 | 11 | 2.212 | 1 Low | 77290 | 2564284 | 0.005 | 3.3597 |
| QC_Low_3 | 2.000 | 6 | 2.110 | 1 Low | 87323 | 3034648 | 0.005 | 3.3885 |
| QC_Med_1 | 40.000 | 1 | 40.300 | 2 Med | 1299131 | 2404628 | 0.090 | 3.3167 |
| QC_Med_2 | 40.000 | −5 | 38.185 | 2 Med | 1228576 | 2399191 | 0.085 | 3.3596 |
| QC_Med_3 | 40.000 | 5 | 42.171 | 2 Med | 1549585 | 2741809 | 0.094 | 3.3888 |
| QC_High_1 | 100.000 | 1 | 101.497 | 3 High | 3219275 | 2387664 | 0.225 | 3.3173 |
| QC_High_2 | 100.000 | −7 | 92.799 | 3 High | 3020319 | 2446947 | 0.206 | 3.3600 |
| QC_High_3 | 100.000 | 1 | 100.902 | 3 High | 3751385 | 2798463 | 0.223 | 3.3884 |
| 45301 | NA | NA | 4.590 | NA | 155747 | 2505735 | 0.010 | 3.3310 |
| 45390 | NA | NA | 8.253 | NA | 322666 | 2896059 | 0.019 | 3.3454 |
| 45466 | NA | NA | 3.246 | NA | 127068 | 2883372 | 0.007 | 3.3314 |
| 45485 | NA | NA | 0.591 | NA | 22294 | 2680691 | 0.001 | 3.3315 |
| 45569 | NA | NA | 0.019 | NA | 1596 | 2641180 | 0.000 | 3.4171 |
| 45634 | NA | NA | 3.033 | NA | 121975 | 2960336 | 0.007 | 3.3453 |
| 45717 | NA | NA | 4.887 | NA | 196316 | 2967875 | 0.011 | 3.3457 |
| 45750 | NA | NA | 2.940 | NA | 119665 | 2995645 | 0.007 | 3.3460 |
| 45752 | NA | NA | 6.298 | NA | 255549 | 3001506 | 0.014 | 3.3457 |
| 45798 | NA | NA | 2.022 | NA | 91673 | 3323059 | 0.005 | 3.3453 |
| 45800 | NA | NA | 5.486 | NA | 225841 | 3043295 | 0.012 | 3.3453 |

-continued

| | | | | 4'-Hydroxy Tamoxifen | | | | |
|---|---|---|---|---|---|---|---|---|
| Sample ID | Specified Conc | % Diff | Calculated Conc | Level | Response | ISTD Response | Response Ratio | RT |
| 45810 | NA | NA | 3.438 | NA | 133315 | 2857926 | 0.008 | 3.3457 |
| 45825 | NA | NA | 6.583 | NA | 260550 | 2928766 | 0.015 | 3.3453 |
| 45835 | NA | NA | 3.962 | NA | 156772 | 2918803 | 0.009 | 3.3461 |
| 45867 | NA | NA | 3.108 | NA | 123680 | 2929971 | 0.007 | 3.3457 |
| 45946 | NA | NA | 5.147 | NA | 199901 | 2869775 | 0.012 | 3.3457 |
| 46037 | NA | NA | 5.643 | NA | 230964 | 3026251 | 0.013 | 3.3453 |
| 46147 | NA | NA | 8.247 | NA | 335804 | 3016126 | 0.019 | 3.3601 |
| 46153 | NA | NA | 3.098 | NA | 119539 | 2841244 | 0.007 | 3.3458 |
| 46180 | NA | NA | 3.884 | NA | 153272 | 2910985 | 0.009 | 3.3453 |
| 46213 | NA | NA | 2.493 | NA | 109506 | 3227714 | 0.006 | 3.3603 |
| 46221 | NA | NA | 3.541 | NA | 130860 | 2723957 | 0.008 | 3.3745 |
| 46283 | NA | NA | 3.892 | NA | 138762 | 2629759 | 0.009 | 3.3601 |
| 46301 | NA | NA | 5.251 | NA | 186491 | 2624655 | 0.012 | 3.3743 |
| 46428 | NA | NA | 3.622 | NA | 132933 | 2705965 | 0.008 | 3.3746 |
| 46442 | NA | NA | 2.922 | NA | 114861 | 2893174 | 0.007 | 3.3744 |
| 46453 | NA | NA | 2.527 | NA | 99000 | 2879043 | 0.006 | 3.3601 |
| 46484 | NA | NA | 3.743 | NA | 144129 | 2839205 | 0.008 | 3.3747 |
| 46518 | NA | NA | 3.108 | NA | 113910 | 2698427 | 0.007 | 3.3747 |
| 46541 | NA | NA | 4.711 | NA | 181415 | 2844378 | 0.011 | 3.3740 |
| 46548 | NA | NA | 4.970 | NA | 190113 | 2826310 | 0.011 | 3.3740 |
| 46606 | NA | NA | 2.090 | NA | 76649 | 2689489 | 0.005 | 3.3744 |
| 46667 | NA | NA | 10.765 | NA | 461374 | 3177987 | 0.024 | 3.3740 |
| 46717 | NA | NA | 7.253 | NA | 304387 | 3106739 | 0.016 | 3.3744 |
| 46731 | NA | NA | 4.273 | NA | 182477 | 3152075 | 0.010 | 3.3744 |
| 46735 | NA | NA | 2.919 | NA | 137705 | 3471886 | 0.007 | 3.3744 |
| 46749 | NA | NA | 3.876 | NA | 174803 | 3326210 | 0.009 | 3.3884 |
| 46841 | NA | NA | 3.195 | NA | 152289 | 3510357 | 0.007 | 3.3884 |
| 46859 | NA | NA | 6.391 | NA | 308879 | 3575840 | 0.014 | 3.3888 |
| 46870 | NA | NA | 3.938 | NA | 187297 | 3508553 | 0.009 | 3.3741 |
| 46896 | NA | NA | 6.647 | NA | 310768 | 3459381 | 0.015 | 3.3744 |
| 46915 | NA | NA | 0.314 | NA | 15189 | 3317417 | 0.001 | 3.3884 |
| B1121 | NA | NA | −0.011 | NA | 712 | 3604644 | 0.000 | 3.3889 |
| B423 | NA | NA | 7.737 | NA | 286757 | 2744489 | 0.017 | 3.3456 |
| B599 | NA | NA | 5.042 | NA | 193874 | 2841340 | 0.011 | 3.3457 |
| B614 | NA | NA | 3.958 | NA | 161177 | 3004219 | 0.009 | 3.3454 |
| B651 | NA | NA | 3.046 | NA | 114124 | 2758319 | 0.007 | 3.3740 |
| B702 | NA | NA | 3.499 | NA | 121390 | 2557001 | 0.008 | 3.3748 |
| Std_1 | 0.800 | 5 | 0.840 | 1 | 35249 | 2958711 | 0.002 | 3.3003 |
| Std_2 | 1.600 | 8 | 1.735 | 2 | 72861 | 2980562 | 0.004 | 3.3093 |
| Std_3 | 3.200 | −2 | 3.124 | 3 | 141591 | 3225973 | 0.007 | 3.3200 |
| Std_4 | 10.000 | −5 | 9.538 | 4 | 424861 | 3179029 | 0.022 | 3.3208 |
| Std_5 | 8.000 | −3 | 7.745 | 5 | 355442 | 3274330 | 0.018 | 3.3195 |
| Std_6 | 16.000 | −4 | 15.293 | 6 | 734203 | 3429193 | 0.036 | 3.3091 |
| Std_7 | 40.000 | −4 | 38.406 | 7 | 1779515 | 3315673 | 0.089 | 3.3088 |
| Std_8 | 64.000 | 3 | 65.945 | 8 | 2961260 | 3219341 | 0.153 | 3.3187 |
| Std_9 | 80.000 | 3 | 82.622 | 9 | 3780953 | 3284353 | 0.192 | 3.3205 |
| Std_10 | 120.000 | −2 | 117.460 | 10 | 5720657 | 3503326 | 0.272 | 3.3206 |
| Std_11 | 160.000 | 2 | 163.231 | 11 | 7179921 | 3173352 | 0.377 | 3.3199 |
| Std_12 | 200.000 | −1 | 197.662 | 12 | 9562222 | 3497821 | 0.456 | 3.3209 |
| QC_Low_2 | 2.000 | 27 | 2.535 | 1 Low | 32742 | 923798 | 0.006 | 3.3201 |
| QC_Low_2 | 2.000 | −2 | 1.964 | 1 Low | 64960 | 2349338 | 0.005 | 3.3408 |
| QC_Low_1 | 2.000 | 3 | 2.061 | 1 Low | 97498 | 3361269 | 0.005 | 3.3205 |
| QC_Low_3 | 2.000 | 12 | 2.234 | 1 Low | 28941 | 920883 | 0.005 | 3.3500 |
| QC_Med_1 | 40.000 | −4 | 38.547 | 2 Med | 1884050 | 3497570 | 0.090 | 3.3195 |
| QC_Med_2 | 40.000 | −2 | 39.081 | 2 Med | 566023 | 1036456 | 0.091 | 3.3303 |
| QC_Med_2 | 40.000 | −14 | 34.202 | 2 Med | 182282 | 381263 | 0.080 | 3.3413 |
| QC_Med_3 | 40.000 | −7 | 37.337 | 2 Med | 341288 | 654060 | 0.087 | 3.3406 |
| QC_High_1 | 100.000 | −5 | 94.884 | 3 High | 4598348 | 3480962 | 0.220 | 3.3193 |
| QC_High_2 | 100.000 | −3 | 96.711 | 3 High | 1251484 | 929592 | 0.224 | 3.3315 |
| QC_High_2 | 100.000 | −4 | 95.878 | 3 High | 578257 | 433233 | 0.222 | 3.3402 |
| QC_High_3 | 100.000 | 6 | 105.842 | 3 High | 892150 | 605869 | 0.245 | 3.3395 |
| 46917 | NA | NA | 6.294 | NA | 359107 | 4069111 | 0.015 | 3.3105 |
| 46951 | NA | NA | 6.037 | NA | 358297 | 4232608 | 0.014 | 3.3187 |
| 46960 | NA | NA | 4.332 | NA | 259114 | 4262102 | 0.010 | 3.3205 |
| 46990 | NA | NA | 3.019 | NA | 186373 | 4393941 | 0.007 | 3.3299 |
| 47076 | NA | NA | 4.647 | NA | 286503 | 4393808 | 0.011 | 3.3313 |
| 47148 | NA | NA | 3.378 | NA | 203309 | 4284871 | 0.008 | 3.3213 |
| 47204 | NA | NA | 4.003 | NA | 246164 | 4381015 | 0.009 | 3.3207 |
| 47223 | NA | NA | 5.265 | NA | 329471 | 4461284 | 0.012 | 3.3197 |
| 47259 | NA | NA | 4.429 | NA | 280965 | 4520722 | 0.010 | 3.3307 |
| 47262 | NA | NA | 2.216 | NA | 146133 | 4688581 | 0.005 | 3.3298 |
| 47271 | NA | NA | 3.533 | NA | 210174 | 4237018 | 0.008 | 3.3204 |
| 47285 | NA | NA | 2.812 | NA | 167507 | 4239139 | 0.007 | 3.3209 |
| 47287 | NA | NA | 4.284 | NA | 247990 | 4124588 | 0.010 | 3.3198 |

4'-Hydroxy Tamoxifen

| Sample ID | Specified Conc | % Diff | Calculated Conc | Level | Response | ISTD Response | Response Ratio | RT |
|---|---|---|---|---|---|---|---|---|
| 47294 | NA | NA | 6.148 | NA | 304761 | 3535140 | 0.014 | 3.3299 |
| 47296 | NA | NA | 6.503 | NA | 415945 | 4561599 | 0.015 | 3.3196 |
| 47362 | NA | NA | 6.575 | NA | 217818 | 2362652 | 0.015 | 3.3205 |
| 47398 | NA | NA | 1.552 | NA | 56103 | 2564963 | 0.004 | 3.3303 |
| 47408 | NA | NA | 4.236 | NA | 140137 | 2356955 | 0.010 | 3.3298 |
| 47429 | NA | NA | 2.437 | NA | 61808 | 1804049 | 0.006 | 3.3213 |
| 47478 | NA | NA | 6.839 | NA | 146298 | 1525812 | 0.016 | 3.3309 |
| 47507 | NA | NA | 5.091 | NA | 72042 | 1008788 | 0.012 | 3.3297 |
| 47512 | NA | NA | 5.454 | NA | 74965 | 979958 | 0.013 | 3.3307 |
| 47547 | NA | NA | 8.056 | NA | 116192 | 1029098 | 0.019 | 3.3290 |
| 47555 | NA | NA | 3.667 | NA | 57301 | 1112989 | 0.009 | 3.3297 |
| 47583 | NA | NA | 6.473 | NA | 86404 | 952010 | 0.015 | 3.3196 |
| 47586 | NA | NA | 5.818 | NA | 76240 | 934334 | 0.014 | 3.3410 |
| 47626 | NA | NA | 3.746 | NA | 45479 | 864793 | 0.009 | 3.3094 |
| 47629 | NA | NA | 3.136 | NA | 29948 | 679734 | 0.007 | 3.3413 |
| 47633 | NA | NA | 3.606 | NA | 26615 | 525691 | 0.008 | 3.3304 |
| 47674 | NA | NA | 0.093 | NA | 847 | 585035 | 0.000 | 3.3612 |
| 47696 | NA | NA | 3.824 | NA | 250106 | 4658812 | 0.009 | 3.3297 |
| 47715 | NA | NA | 5.750 | NA | 261070 | 3237523 | 0.013 | 3.3313 |
| B109 | NA | NA | 1.524 | NA | 14768 | 687552 | 0.004 | 3.3488 |
| B124 | NA | NA | 8.718 | NA | 30895 | 252876 | 0.020 | 3.3412 |
| B138 | NA | NA | 3.821 | NA | 75737 | 1411978 | 0.009 | 3.3510 |
| B151 | NA | NA | 4.594 | NA | 57488 | 891738 | 0.011 | 3.3414 |
| B174 | NA | NA | 2.520 | NA | 26797 | 756341 | 0.006 | 3.3405 |
| B209 | NA | NA | 6.388 | NA | 48930 | 546310 | 0.015 | 3.3391 |
| B211 | NA | NA | 3.127 | NA | 38515 | 876857 | 0.007 | 3.3300 |
| B218 | NA | NA | 3.539 | NA | 36919 | 742987 | 0.008 | 3.3303 |
| B249 | NA | NA | 5.207 | NA | 21627 | 296085 | 0.012 | 3.3407 |
| B348 | NA | NA | 3.459 | NA | 73040 | 1503576 | 0.008 | 3.3409 |
| B379 | NA | NA | 6.245 | NA | 28271 | 322831 | 0.015 | 3.3412 |
| B416 | NA | NA | 3.862 | NA | 17684 | 326151 | 0.009 | 3.3410 |
| B417 | NA | NA | 4.720 | NA | 176904 | 2671010 | 0.011 | 3.3198 |
| B50 | NA | NA | 0.111 | NA | 667 | 393861 | 0.000 | 3.3521 |
| B77 | NA | NA | 4.677 | NA | 89665 | 1366217 | 0.011 | 3.3421 |
| B793 | NA | NA | 5.094 | NA | 21269 | 297647 | 0.012 | 3.3317 |
| B875 | NA | NA | 3.932 | NA | 27943 | 506274 | 0.009 | 3.3405 |
| B96 | NA | NA | 2.546 | NA | 22119 | 617916 | 0.006 | 3.3514 |

N-Desmethyl Tamoxifen

| Sample ID | Specified Conc | % Diff | Calculated Conc | Level | Response | ISTD Response | Response Ratio | RT |
|---|---|---|---|---|---|---|---|---|
| Std_1 | 5.000 | 0 | 4.995 | 1 | 2214356 | 10007701 | 0.037 | 4.6555 |
| Std_2 | 10.000 | −1 | 9.920 | 2 | 4350445 | 10345933 | 0.070 | 4.6415 |
| Std_3 | 20.000 | 1 | 20.214 | 3 | 8828632 | 10550159 | 0.139 | 4.6408 |
| Std_4 | 62.500 | −5 | 59.587 | 4 | 24912812 | 10256233 | 0.405 | 4.6413 |
| Std_5 | 50.000 | 3 | 51.472 | 5 | 22282634 | 10606046 | 0.350 | 4.6412 |
| Std_6 | 100.000 | 1 | 101.387 | 6 | 42220636 | 10250550 | 0.686 | 4.6409 |
| Std_7 | 250.000 | −3 | 241.804 | 7 | 101199824 | 10335393 | 1.632 | 4.6408 |
| Std_8 | 400.000 | 5 | 419.552 | 8 | 164136702 | 9675655 | 2.827 | 4.6413 |
| Std_9 | 500.000 | 2 | 508.595 | 9 | 207205488 | 10081408 | 3.426 | 4.6412 |
| Std_10 | 750.000 | −4 | 722.443 | 10 | 297647976 | 10206088 | 4.861 | 4.6412 |
| Std_11 | 1000.000 | 0 | 995.302 | 11 | 411465548 | 10253258 | 6.688 | 4.6408 |
| Std_12 | 1250.000 | 1 | 1262.236 | 12 | 512184551 | 10075081 | 8.473 | 4.6409 |
| QC_Low_1 | 40.000 | 5 | 41.976 | 1 Low | 18949835 | 11037046 | 0.286 | 4.6412 |
| QC_Low_2 | 40.000 | 3 | 41.137 | 1 Low | 18965589 | 11268913 | 0.281 | 4.6695 |
| QC_Low_3 | 40.000 | −1 | 39.797 | 1 Low | 20961957 | 12869496 | 0.271 | 4.6841 |
| QC_Med_1 | 200.000 | 0 | 200.142 | 2 Med | 86969927 | 10724951 | 1.352 | 4.6410 |
| QC_Med_2 | 200.000 | −2 | 195.105 | 2 Med | 82826081 | 10476833 | 1.318 | 4.6695 |
| QC_Med_3 | 200.000 | −3 | 194.728 | 2 Med | 94847560 | 12020557 | 1.315 | 4.6843 |
| QC_High_1 | 800.000 | 1 | 806.621 | 3 High | 349559336 | 10739364 | 5.425 | 4.6272 |
| QC_High_2 | 800.000 | −4 | 766.892 | 3 High | 321869979 | 10399085 | 5.159 | 4.6699 |
| QC_High_3 | 800.000 | −3 | 772.284 | 3 High | 369290721 | 11848163 | 5.195 | 4.6839 |
| 45301 | NA | NA | 26.273 | NA | 11841632 | 10945501 | 0.180 | 4.6552 |
| 45390 | NA | NA | 39.710 | NA | 18654553 | 11477691 | 0.271 | 4.6553 |
| 45466 | NA | NA | 14.131 | NA | 7051102 | 11934357 | 0.098 | 4.6556 |
| 45485 | NA | NA | 2.104 | NA | 1235242 | 11839387 | 0.017 | 4.6558 |
| 45569 | NA | NA | −0.438 | NA | 17606 | 11822707 | 0.000 | 4.6553 |

-continued

| | | | | N-Desmethyl Tamoxifen | | | | |
|---|---|---|---|---|---|---|---|---|
| Sample ID | Specified Conc | % Diff | Calculated Conc | Level | Response | ISTD Response | Response Ratio | RT |
| 45634 | NA | NA | 18.338 | NA | 9228298 | 12127381 | 0.127 | 4.6552 |
| 45717 | NA | NA | 10.770 | NA | 5532916 | 12163713 | 0.076 | 4.6556 |
| 45750 | NA | NA | 4.916 | NA | 2717384 | 12460010 | 0.036 | 4.6559 |
| 45752 | NA | NA | 23.367 | NA | 12033795 | 12478509 | 0.161 | 4.6699 |
| 45798 | NA | NA | 8.081 | NA | 4514702 | 13045004 | 0.058 | 4.6695 |
| 45800 | NA | NA | 12.381 | NA | 6600043 | 12691932 | 0.087 | 4.6552 |
| 45810 | NA | NA | 21.579 | NA | 10724905 | 12022578 | 0.149 | 4.6557 |
| 45825 | NA | NA | 33.817 | NA | 17048836 | 12292179 | 0.231 | 4.6696 |
| 45835 | NA | NA | 11.219 | NA | 5770806 | 12199963 | 0.079 | 4.6704 |
| 45867 | NA | NA | 12.834 | NA | 6456515 | 11992891 | 0.090 | 4.6699 |
| 45946 | NA | NA | 12.791 | NA | 6297921 | 11736675 | 0.089 | 4.6557 |
| 46037 | NA | NA | 10.380 | NA | 5360503 | 12208515 | 0.073 | 4.6695 |
| 46147 | NA | NA | 44.324 | NA | 21087917 | 11638790 | 0.302 | 4.6700 |
| 46153 | NA | NA | 13.246 | NA | 6744190 | 12151619 | 0.093 | 4.6700 |
| 46180 | NA | NA | 13.893 | NA | 7099200 | 12215198 | 0.097 | 4.6696 |
| 46213 | NA | NA | 13.928 | NA | 7116545 | 12214797 | 0.097 | 4.6702 |
| 46221 | NA | NA | 26.106 | NA | 11555669 | 10748057 | 0.179 | 4.6701 |
| 46283 | NA | NA | 24.324 | NA | 10709139 | 10676283 | 0.167 | 4.6843 |
| 46301 | NA | NA | 29.768 | NA | 14013373 | 11455981 | 0.204 | 4.6842 |
| 46428 | NA | NA | 9.931 | NA | 4563811 | 10842547 | 0.070 | 4.6845 |
| 46442 | NA | NA | 6.573 | NA | 3284257 | 11519780 | 0.048 | 4.6843 |
| 46453 | NA | NA | 14.676 | NA | 7224761 | 11788779 | 0.102 | 4.6844 |
| 46484 | NA | NA | 15.352 | NA | 6937804 | 10836949 | 0.107 | 4.6846 |
| 46518 | NA | NA | 5.940 | NA | 2822979 | 10878008 | 0.043 | 4.6846 |
| 46541 | NA | NA | 12.145 | NA | 5456620 | 10689596 | 0.085 | 4.6839 |
| 46548 | NA | NA | 17.369 | NA | 7686125 | 10648745 | 0.120 | 4.6839 |
| 46606 | NA | NA | 13.382 | NA | 6230069 | 11114932 | 0.093 | 4.6843 |
| 46667 | NA | NA | 54.075 | NA | 26635133 | 12073060 | 0.368 | 4.6839 |
| 46717 | NA | NA | 32.189 | NA | 15985951 | 12099953 | 0.220 | 4.6843 |
| 46731 | NA | NA | 23.463 | NA | 11781079 | 12167379 | 0.161 | 4.6843 |
| 46735 | NA | NA | 10.658 | NA | 6231222 | 13836352 | 0.075 | 4.6844 |
| 46749 | NA | NA | 18.278 | NA | 10047672 | 13245981 | 0.126 | 4.6839 |
| 46841 | NA | NA | 23.201 | NA | 12927666 | 13499605 | 0.160 | 4.6839 |
| 46859 | NA | NA | 35.736 | NA | 20430737 | 13949932 | 0.244 | 4.6843 |
| 46870 | NA | NA | 9.464 | NA | 5495150 | 13667994 | 0.067 | 4.6840 |
| 46896 | NA | NA | 39.389 | NA | 22095261 | 13704056 | 0.269 | 4.6843 |
| 46915 | NA | NA | 1.258 | NA | 945809 | 13492832 | 0.012 | 4.6839 |
| B1121 | NA | NA | −0.449 | NA | 14423 | 13610861 | 0.000 | 4.6845 |
| B423 | NA | NA | 33.052 | NA | 15825521 | 11670269 | 0.226 | 4.6556 |
| B599 | NA | NA | 15.587 | NA | 7789173 | 11988574 | 0.108 | 4.6556 |
| B614 | NA | NA | 14.595 | NA | 7250764 | 11894417 | 0.102 | 4.6553 |
| B651 | NA | NA | 17.086 | NA | 8096715 | 11398887 | 0.118 | 4.6839 |
| B702 | NA | NA | 20.529 | NA | 8668370 | 10203235 | 0.142 | 4.6847 |
| Std_1 | 5.000 | 4 | 5.216 | 1 | 3035366 | 12894595 | 0.039 | 4.6451 |
| Std_2 | 10.000 | 5 | 10.513 | 2 | 6039685 | 13277968 | 0.076 | 4.6539 |
| Std_3 | 20.000 | 0 | 19.997 | 3 | 12196051 | 14385916 | 0.141 | 4.6542 |
| Std_4 | 62.500 | −6 | 58.667 | 4 | 34713350 | 14166401 | 0.408 | 4.6556 |
| Std_5 | 50.000 | −2 | 48.758 | 5 | 29854945 | 14637029 | 0.340 | 4.6434 |
| Std_6 | 100.000 | −3 | 96.677 | 6 | 60835111 | 15109059 | 0.671 | 4.6533 |
| Std_7 | 250.000 | −1 | 247.393 | 7 | 150417601 | 14628708 | 1.714 | 4.6430 |
| Std_8 | 400.000 | 5 | 418.186 | 8 | 249322031 | 14341070 | 2.898 | 4.6422 |
| Std_9 | 500.000 | 0 | 502.301 | 9 | 311783615 | 14926066 | 3.481 | 4.6444 |
| Std_10 | 750.000 | −2 | 736.267 | 10 | 481407377 | 15705917 | 5.109 | 4.6445 |
| Std_11 | 1000.000 | 0 | 1004.915 | 11 | 593251935 | 14160635 | 6.982 | 4.6440 |
| Std_12 | 1250.000 | 0 | 1248.606 | 12 | 768772647 | 14749010 | 8.687 | 4.6449 |
| QC_Low_2 | 40.000 | −11 | 35.438 | 1 Low | 5014390 | 3370741 | 0.248 | 4.6642 |
| QC_Low_2 | 40.000 | −1 | 39.697 | 1 Low | 8530728 | 5126252 | 0.277 | 4.6752 |
| QC_Low_1 | 40.000 | 0 | 40.102 | 1 Low | 25849688 | 15378255 | 0.280 | 4.6636 |
| QC_Low_3 | 40.000 | 4 | 41.700 | 1 Low | 5035346 | 2882014 | 0.291 | 4.6636 |
| QC_Med_1 | 200.000 | −6 | 187.687 | 2 Med | 122092292 | 15647367 | 1.300 | 4.6539 |
| QC_Med_2 | 200.000 | −22 | 156.276 | 2 Med | 19686199 | 3029159 | 1.083 | 4.6544 |
| QC_Med_2 | 200.000 | −6 | 187.708 | 2 Med | 9278718 | 1189027 | 1.301 | 4.6760 |
| QC_Med_3 | 200.000 | −7 | 185.679 | 2 Med | 14183336 | 1837368 | 1.287 | 4.6646 |
| QC_High_1 | 800.000 | −5 | 756.162 | 3 High | 475031778 | 15088636 | 5.247 | 4.6434 |
| QC_High_2 | 800.000 | −16 | 674.720 | 3 High | 70649330 | 2515953 | 4.680 | 4.6456 |
| QC_High_2 | 800.000 | −8 | 733.618 | 3 High | 46860519 | 1534366 | 5.090 | 4.6643 |
| QC_High_3 | 800.000 | −6 | 751.226 | 3 High | 64370878 | 2058125 | 5.213 | 4.6634 |
| 46917 | NA | NA | 26.132 | NA | 18119897 | 16442596 | 0.184 | 4.6552 |
| 46951 | NA | NA | 17.249 | NA | 12118193 | 16511132 | 0.122 | 4.6630 |
| 46960 | NA | NA | 18.233 | NA | 13027133 | 16815396 | 0.129 | 4.6548 |
| 46990 | NA | NA | 4.714 | NA | 3672603 | 17112987 | 0.036 | 4.6638 |
| 47076 | NA | NA | 17.044 | NA | 12399477 | 17092640 | 0.121 | 4.6554 |
| 47148 | NA | NA | 10.751 | NA | 7738928 | 16653008 | 0.077 | 4.6557 |
| 47204 | NA | NA | 21.609 | NA | 15138607 | 16552674 | 0.152 | 4.6551 |

-continued

N-Desmethyl Tamoxifen

| Sample ID | Specified Conc | % Diff | Calculated Conc | Level | Response | ISTD Response | Response Ratio | RT |
|---|---|---|---|---|---|---|---|---|
| 47223 | NA | NA | 26.069 | NA | 18575235 | 16896149 | 0.183 | 4.6536 |
| 47259 | NA | NA | 24.482 | NA | 17901150 | 17318645 | 0.172 | 4.6653 |
| 47262 | NA | NA | 11.522 | NA | 8873081 | 17865097 | 0.083 | 4.6639 |
| 47271 | NA | NA | 16.032 | NA | 11167382 | 16337683 | 0.114 | 4.6551 |
| 47285 | NA | NA | 10.523 | NA | 6632132 | 14567325 | 0.076 | 4.6551 |
| 47287 | NA | NA | 7.253 | NA | 4150522 | 12977664 | 0.053 | 4.6644 |
| 47294 | NA | NA | 23.672 | NA | 10097368 | 10096633 | 0.167 | 4.6642 |
| 47296 | NA | NA | 25.731 | NA | 18048131 | 16627998 | 0.181 | 4.6639 |
| 47362 | NA | NA | 30.720 | NA | 9623565 | 7447965 | 0.215 | 4.6651 |
| 47398 | NA | NA | 11.900 | NA | 2953091 | 5764235 | 0.085 | 4.6647 |
| 47408 | NA | NA | 14.802 | NA | 2642033 | 4176803 | 0.105 | 4.6641 |
| 47429 | NA | NA | 11.723 | NA | 2739959 | 5425673 | 0.084 | 4.6662 |
| 47478 | NA | NA | 26.901 | NA | 5450199 | 4806728 | 0.189 | 4.6650 |
| 47507 | NA | NA | 25.265 | NA | 3608824 | 3385136 | 0.178 | 4.6642 |
| 47512 | NA | NA | 22.956 | NA | 2507451 | 2583917 | 0.162 | 4.6653 |
| 47547 | NA | NA | 39.779 | NA | 5279817 | 3166205 | 0.278 | 4.6629 |
| 47555 | NA | NA | 15.859 | NA | 2083193 | 3080093 | 0.113 | 4.6742 |
| 47583 | NA | NA | 8.888 | NA | 929424 | 2398272 | 0.065 | 4.6641 |
| 47586 | NA | NA | 30.921 | NA | 3210173 | 2468503 | 0.217 | 4.6650 |
| 47626 | NA | NA | 18.322 | NA | 1864197 | 2394881 | 0.130 | 4.6640 |
| 47629 | NA | NA | 5.135 | NA | 450948 | 1943285 | 0.039 | 4.6761 |
| 47633 | NA | NA | 12.866 | NA | 967726 | 1751989 | 0.092 | 4.6645 |
| 47674 | NA | NA | −0.454 | NA | 874 | 1612859 | 0.000 | 4.6644 |
| 47696 | NA | NA | 16.209 | NA | 3169773 | 4588361 | 0.115 | 4.6641 |
| 47715 | NA | NA | 13.470 | NA | 1656231 | 2868681 | 0.096 | 4.6758 |
| B109 | NA | NA | 11.432 | NA | 1033667 | 2097056 | 0.082 | 4.6825 |
| B124 | NA | NA | 14.692 | NA | 692056 | 1101989 | 0.105 | 4.6754 |
| B138 | NA | NA | 22.437 | NA | 1400162 | 1475589 | 0.158 | 4.6752 |
| B151 | NA | NA | 21.416 | NA | 1047332 | 1155265 | 0.151 | 4.6656 |
| B174 | NA | NA | 10.349 | NA | 412904 | 921568 | 0.075 | 4.6644 |
| B209 | NA | NA | 14.006 | NA | 798577 | 1331885 | 0.100 | 4.6731 |
| B211 | NA | NA | 11.346 | NA | 432864 | 884514 | 0.082 | 4.6748 |
| B218 | NA | NA | 14.915 | NA | 990100 | 1553714 | 0.106 | 4.6751 |
| B249 | NA | NA | 15.747 | NA | 589399 | 877488 | 0.112 | 4.6749 |
| B348 | NA | NA | 15.742 | NA | 1252157 | 1864674 | 0.112 | 4.6755 |
| B379 | NA | NA | 16.374 | NA | 789263 | 1131237 | 0.116 | 4.6754 |
| B416 | NA | NA | 13.889 | NA | 652860 | 1097759 | 0.099 | 4.6655 |
| B417 | NA | NA | 17.747 | NA | 4252133 | 5635185 | 0.126 | 4.6645 |
| B50 | NA | NA | −0.344 | NA | 10474 | 2062412 | 0.001 | 4.6659 |
| B77 | NA | NA | 13.213 | NA | 997904 | 1760839 | 0.094 | 4.6666 |
| B793 | NA | NA | 16.843 | NA | 766191 | 1068454 | 0.120 | 4.6764 |
| B875 | NA | NA | 19.567 | NA | 1696007 | 2043385 | 0.138 | 4.6748 |
| B96 | NA | NA | 9.888 | NA | 952563 | 2220513 | 0.071 | 4.6755 |

Tamoxifen

Tamoxifen

| Sample ID | Specified Conc | % Diff | Calculated Conc | Level | Response | ISTD Response | Sample Type | Response Ratio | RT |
|---|---|---|---|---|---|---|---|---|---|
| Std_1 | 5.000 | −5 | 4.772 | 1 | 359548 | 11850488 | Std Bracket Sample | 0.005 | 4.8747 |
| Std_2 | 10.000 | 0 | 10.034 | 2 | 715154 | 12408704 | Std Bracket Sample | 0.010 | 4.8751 |
| Std_3 | 20.000 | 4 | 20.855 | 3 | 1400493 | 12310503 | Std Bracket Sample | 0.019 | 4.8744 |
| Std_4 | 62.500 | −6 | 58.586 | 4 | 3787383 | 12232259 | Std Bracket Sample | 0.052 | 4.8748 |
| Std_5 | 50.000 | 8 | 53.761 | 5 | 3508560 | 12329561 | Std Bracket Sample | 0.047 | 4.8748 |
| Std_6 | 100.000 | −3 | 97.395 | 6 | 6307063 | 12335431 | Std Bracket Sample | 0.085 | 4.8745 |
| Std_7 | 250.000 | −2 | 245.182 | 7 | 15411820 | 12028313 | Std Bracket Sample | 0.214 | 4.8744 |
| Std_8 | 400.000 | 4 | 417.365 | 8 | 25925506 | 11879210 | Std Bracket Sample | 0.364 | 4.8749 |
| Std_9 | 500.000 | 3 | 514.348 | 9 | 31812253 | 11817737 | Std Bracket Sample | 0.449 | 4.8748 |
| Std_10 | 750.000 | −5 | 709.105 | 10 | 45628283 | 12268396 | Std Bracket Sample | 0.620 | 4.8748 |

-continued

| | | | | | | Tamoxifen | | | |
|---|---|---|---|---|---|---|---|---|---|
| Std_11 | 1000.000 | 1 | 1008.577 | 11 | 66892579 | 12598429 | Std Bracket Sample | 0.885 | 4.8601 |
| Std_12 | 1250.000 | 1 | 1257.491 | 12 | 77548728 | 11676394 | Std Bracket Sample | 1.107 | 4.8601 |
| QC_Low_1 | 40.000 | 1 | 40.559 | 1 Low | 2820699 | 13057549 | QC Sample | 0.036 | 4.8604 |
| QC_Low_2 | 40.000 | −6 | 37.761 | 1 Low | 2690867 | 13354380 | QC Sample | 0.034 | 4.9031 |
| QC_Low_3 | 40.000 | −11 | 35.695 | 1 Low | 2960468 | 15518087 | QC Sample | 0.032 | 4.9177 |
| QC_Med_1 | 200.000 | 3 | 205.744 | 2 Med | 13931187 | 12953193 | QC Sample | 0.179 | 4.8602 |
| QC_Med_2 | 200.000 | −9 | 182.179 | 2 Med | 12123620 | 12726226 | QC Sample | 0.159 | 4.9032 |
| QC_Med_3 | 200.000 | −6 | 187.142 | 2 Med | 14410318 | 14726719 | QC Sample | 0.163 | 4.9035 |
| QC_High_1 | 800.000 | 3 | 820.859 | 3 High | 54350709 | 12607050 | QC Sample | 0.719 | 4.8607 |
| QC_High_2 | 800.000 | −9 | 729.436 | 3 High | 48823606 | 12758558 | QC Sample | 0.638 | 4.9035 |
| QC_High_3 | 800.000 | −6 | 750.663 | 3 High | 55810349 | 14168310 | QC Sample | 0.657 | 4.9032 |
| 45301 | NA | NA | 130.875 | NA | 9201591 | 13424057 | Unknown Sample | 0.114 | 4.8745 |
| 45390 | NA | NA | 142.588 | NA | 10729349 | 14374421 | Unknown Sample | 0.124 | 4.8889 |
| 45466 | NA | NA | 51.861 | NA | 3887923 | 14153276 | Unknown Sample | 0.046 | 4.8892 |
| 45485 | NA | NA | 2.025 | NA | 225794 | 14029301 | Unknown Sample | 0.003 | 4.8893 |
| 45569 | NA | NA | −0.642 | NA | 31725 | 13993172 | Unknown Sample | 0.000 | 4.9032 |
| 45634 | NA | NA | 79.422 | NA | 6087679 | 14568254 | Unknown Sample | 0.070 | 4.8888 |
| 45717 | NA | NA | 114.657 | NA | 8769809 | 14590327 | Unknown Sample | 0.100 | 4.8892 |
| 45750 | NA | NA | 26.715 | NA | 2100131 | 14567323 | Unknown Sample | 0.024 | 4.8895 |
| 45752 | NA | NA | 103.765 | NA | 7994477 | 14684389 | Unknown Sample | 0.091 | 4.8892 |
| 45798 | NA | NA | 35.068 | NA | 2844990 | 15171845 | Unknown Sample | 0.031 | 4.8888 |
| 45800 | NA | NA | 50.405 | NA | 3867320 | 14476922 | Unknown Sample | 0.045 | 4.8888 |
| 45810 | NA | NA | 115.360 | NA | 8718130 | 14416627 | Unknown Sample | 0.101 | 4.8893 |
| 45825 | NA | NA | 179.654 | NA | 13173726 | 14022261 | Unknown Sample | 0.157 | 4.8889 |
| 45835 | NA | NA | 116.025 | NA | 8544018 | 14048402 | Unknown Sample | 0.101 | 4.8896 |
| 45867 | NA | NA | 90.584 | NA | 6772504 | 14231363 | Unknown Sample | 0.079 | 4.8892 |
| 45946 | NA | NA | 68.180 | NA | 5068384 | 14099973 | Unknown Sample | 0.060 | 4.8893 |
| 46037 | NA | NA | 122.733 | NA | 9267700 | 14411275 | Unknown Sample | 0.107 | 4.8888 |
| 46147 | NA | NA | 245.606 | NA | 18005272 | 14028174 | Unknown Sample | 0.214 | 4.8892 |
| 46153 | NA | NA | 64.050 | NA | 4709356 | 13932869 | Unknown Sample | 0.056 | 4.8893 |
| 46180 | NA | NA | 45.657 | NA | 3482346 | 14361051 | Unknown Sample | 0.040 | 4.8888 |
| 46213 | NA | NA | 39.700 | NA | 3002720 | 14193252 | Unknown Sample | 0.035 | 4.8894 |
| 46221 | NA | NA | 60.817 | NA | 4132298 | 12864807 | Unknown Sample | 0.054 | 4.9037 |
| 46283 | NA | NA | 106.601 | NA | 7203546 | 12882631 | Unknown Sample | 0.093 | 4.9036 |
| 46301 | NA | NA | 175.670 | NA | 12247590 | 13331077 | Unknown Sample | 0.153 | 4.9035 |
| 46428 | NA | NA | 102.971 | NA | 7021703 | 12996179 | Unknown Sample | 0.090 | 4.9037 |
| 46442 | NA | NA | 34.971 | NA | 2612135 | 13967304 | Unknown Sample | 0.031 | 4.9036 |
| 46453 | NA | NA | 76.528 | NA | 5324388 | 13217410 | Unknown Sample | 0.067 | 4.9036 |
| 46484 | NA | NA | 134.492 | NA | 9125489 | 12957248 | Unknown Sample | 0.117 | 4.9038 |
| 46518 | NA | NA | 32.697 | NA | 2256501 | 12878575 | Unknown Sample | 0.029 | 4.9182 |
| 46541 | NA | NA | 77.359 | NA | 4843270 | 11895464 | Unknown Sample | 0.068 | 4.9175 |
| 46548 | NA | NA | 85.387 | NA | 5732477 | 12770877 | Unknown Sample | 0.075 | 4.9032 |
| 46606 | NA | NA | 59.848 | NA | 4199528 | 13282068 | Unknown Sample | 0.053 | 4.9179 |

| Tamoxifen | | | | | | | | | |
|---|---|---|---|---|---|---|---|---|---|
| 46667 | NA | NA | 135.598 | NA | 10414841 | 14668087 | Unknown Sample | 0.118 | 4.9032 |
| 46717 | NA | NA | 182.112 | NA | 14165239 | 14874821 | Unknown Sample | 0.159 | 4.9036 |
| 46731 | NA | NA | 145.655 | NA | 10828856 | 14203833 | Unknown Sample | 0.127 | 4.9036 |
| 46735 | NA | NA | 60.560 | NA | 5245978 | 16400049 | Unknown Sample | 0.053 | 4.9180 |
| 46749 | NA | NA | 97.135 | NA | 8098485 | 15881133 | Unknown Sample | 0.085 | 4.9032 |
| 46841 | NA | NA | 91.310 | NA | 7725533 | 16106190 | Unknown Sample | 0.080 | 4.9032 |
| 46859 | NA | NA | 129.621 | NA | 11198473 | 16494335 | Unknown Sample | 0.113 | 4.9036 |
| 46870 | NA | NA | 94.153 | NA | 7837005 | 15850306 | Unknown Sample | 0.082 | 4.9176 |
| 46896 | NA | NA | 152.754 | NA | 13132709 | 16429150 | Unknown Sample | 0.133 | 4.9035 |
| 46915 | NA | NA | 2.000 | NA | 257251 | 16113116 | Unknown Sample | 0.003 | 4.9032 |
| B1121 | NA | NA | −0.601 | NA | 39714 | 16006905 | Unknown Sample | 0.000 | 4.9181 |
| B423 | NA | NA | 140.264 | NA | 10248102 | 13955854 | Unknown Sample | 0.122 | 4.8748 |
| B599 | NA | NA | 68.107 | NA | 5070892 | 14121922 | Unknown Sample | 0.060 | 4.8892 |
| B614 | NA | NA | 74.326 | NA | 5545621 | 14169095 | Unknown Sample | 0.065 | 4.8889 |
| B651 | NA | NA | 63.727 | NA | 4449989 | 13231237 | Unknown Sample | 0.056 | 4.9175 |
| B702 | NA | NA | 67.581 | NA | 4315968 | 12111629 | Unknown Sample | 0.059 | 4.9040 |

| Sample ID | Specified Conc | % Diff | Calculated Conc | Level | Response | ISTD Response | Response Ratio | RT |
|---|---|---|---|---|---|---|---|---|
| Std_1 | 5.000 | 5.166 | 3 | 1 | 518618 | 15827044 | 0.005 | 4.8732 |
| Std_2 | 10.000 | 10.599 | 6 | 2 | 987999 | 15876927 | 0.010 | 4.8716 |
| Std_3 | 20.000 | 19.658 | −2 | 3 | 1961473 | 17615708 | 0.019 | 4.8825 |
| Std_4 | 62.500 | 60.153 | −4 | 4 | 5563829 | 16808158 | 0.055 | 4.8734 |
| Std_5 | 50.000 | 48.987 | −2 | 5 | 4721538 | 17459086 | 0.045 | 4.8716 |
| Std_6 | 100.000 | 96.775 | −3 | 6 | 9592859 | 18106874 | 0.088 | 4.8713 |
| Std_7 | 250.000 | 244.797 | −2 | 7 | 23979787 | 17971445 | 0.222 | 4.8711 |
| Std_8 | 400.000 | 412.508 | 3 | 8 | 40252034 | 17905472 | 0.375 | 4.8703 |
| Std_9 | 500.000 | 509.298 | 2 | 9 | 49965048 | 17996378 | 0.463 | 4.8726 |
| Std_10 | 750.000 | 732.247 | −2 | 10 | 78874481 | 19736612 | 0.666 | 4.8726 |
| Std_11 | 1000.000 | 1014.448 | 1 | 11 | 96247175 | 17353278 | 0.924 | 4.8823 |
| Std_12 | 1250.000 | 1242.858 | −1 | 12 | 128307307 | 18853095 | 1.134 | 4.8731 |
| QC_Low_2 | 40.000 | 41.992 | 5 | 1 Low | 775940 | 3337584 | 0.039 | 4.8924 |
| QC_Low_2 | 40.000 | 33.880 | −15 | 1 Low | 743748 | 3945978 | 0.031 | 4.8930 |
| QC_Low_1 | 40.000 | 38.644 | −3 | 1 Low | 3934913 | 18359852 | 0.036 | 4.8829 |
| QC_Low_3 | 40.000 | 42.899 | 7 | 1 Low | 775947 | 3268415 | 0.040 | 4.8917 |
| QC_Med_1 | 200.000 | 189.461 | −5 | 2 Med | 19360578 | 18735738 | 0.172 | 4.8820 |
| QC_Med_2 | 200.000 | 186.560 | −7 | 2 Med | 3045361 | 2992744 | 0.170 | 4.8825 |
| QC_Med_2 | 200.000 | 201.031 | 1 | 2 Med | 1686040 | 1537992 | 0.183 | 4.8938 |
| QC_Med_3 | 200.000 | 187.608 | −6 | 2 Med | 2096153 | 2048464 | 0.171 | 4.8928 |
| QC_High_1 | 800.000 | 769.738 | −4 | 3 High | 78604327 | 18706868 | 0.700 | 4.8716 |
| QC_High_2 | 800.000 | 705.358 | −12 | 3 High | 10431828 | 2710267 | 0.642 | 4.8840 |
| QC_High_2 | 800.000 | 721.156 | −10 | 3 High | 5900132 | 1499181 | 0.656 | 4.8925 |
| QC_High_3 | 800.000 | 819.576 | 2 | 3 High | 10644697 | 2378535 | 0.746 | 4.8814 |
| 46917 | NA | 114.854 | NA | NA | 12137244 | 19328077 | 0.105 | 4.8730 |
| 46951 | NA | 142.801 | NA | NA | 14998177 | 19234280 | 0.130 | 4.8807 |
| 46960 | NA | 98.319 | NA | NA | 10565017 | 19631305 | 0.090 | 4.8829 |
| 46990 | NA | 28.847 | NA | NA | 3132543 | 19434679 | 0.027 | 4.8920 |
| 47076 | NA | 101.708 | NA | NA | 11142969 | 20020581 | 0.093 | 4.8835 |
| 47148 | NA | 59.043 | NA | NA | 6308156 | 19409932 | 0.054 | 4.8838 |
| 47204 | NA | 102.845 | NA | NA | 10718957 | 19047492 | 0.094 | 4.8833 |
| 47223 | NA | 78.569 | NA | NA | 8469906 | 19653465 | 0.072 | 4.8817 |
| 47259 | NA | 114.884 | NA | NA | 12650349 | 20139926 | 0.105 | 4.8935 |
| 47262 | NA | 46.850 | NA | NA | 5288079 | 20429903 | 0.043 | 4.8920 |
| 47271 | NA | 82.980 | NA | NA | 8646221 | 19006812 | 0.076 | 4.8834 |
| 47285 | NA | 54.159 | NA | NA | 4680113 | 15679142 | 0.050 | 4.8833 |
| 47287 | NA | 36.896 | NA | NA | 2820080 | 13767116 | 0.034 | 4.8823 |
| 47294 | NA | 84.735 | NA | NA | 5185004 | 11164296 | 0.077 | 4.8923 |
| 47296 | NA | 104.447 | NA | NA | 10852415 | 18991199 | 0.095 | 4.8817 |
| 47362 | NA | 115.191 | NA | NA | 4816356 | 7647588 | 0.105 | 4.8932 |
| 47398 | NA | 28.116 | NA | NA | 905707 | 5760762 | 0.026 | 4.8929 |

Tamoxifen

| | | | | | | | | |
|---|---|---|---|---|---|---|---|---|
| 47408 | NA | 102.226 | NA | NA | 2846054 | 5087819 | 0.093 | 4.8923 |
| 47429 | NA | 56.922 | NA | NA | 1821271 | 5809718 | 0.052 | 4.8843 |
| 47478 | NA | 143.152 | NA | NA | 3596365 | 4600874 | 0.130 | 4.8931 |
| 47507 | NA | 131.205 | NA | NA | 2452209 | 3421199 | 0.119 | 4.8923 |
| 47512 | NA | 85.263 | NA | NA | 1482894 | 3173362 | 0.078 | 4.8935 |
| 47547 | NA | 221.439 | NA | NA | 3947988 | 3270236 | 0.201 | 4.8910 |
| 47555 | NA | 72.270 | NA | NA | 1217277 | 3067942 | 0.066 | 4.8920 |
| 47583 | NA | 42.391 | NA | NA | 594900 | 2535249 | 0.039 | 4.8922 |
| 47586 | NA | 136.423 | NA | NA | 2212374 | 2969176 | 0.124 | 4.8932 |
| 47626 | NA | 84.268 | NA | NA | 1417562 | 3069017 | 0.077 | 4.8921 |
| 47629 | NA | 42.703 | NA | NA | 531982 | 2250912 | 0.039 | 4.9043 |
| 47633 | NA | 80.594 | NA | NA | 794839 | 1798467 | 0.074 | 4.8826 |
| 47674 | NA | −0.750 | NA | NA | 1647 | 2363729 | 0.000 | 4.9231 |
| 47696 | NA | 119.835 | NA | NA | 3332289 | 5087393 | 0.109 | 4.8923 |
| 47715 | NA | 132.525 | NA | NA | 1832445 | 2531225 | 0.121 | 4.9040 |
| B109 | NA | 24.561 | NA | NA | 393995 | 2856321 | 0.023 | 4.9004 |
| B124 | NA | 87.045 | NA | NA | 431391 | 904445 | 0.079 | 4.9035 |
| B138 | NA | 97.370 | NA | NA | 877117 | 1645556 | 0.089 | 4.9034 |
| B151 | NA | 94.329 | NA | NA | 715445 | 1385149 | 0.086 | 4.8937 |
| B174 | NA | 56.169 | NA | NA | 511797 | 1654158 | 0.052 | 4.8925 |
| B209 | NA | 152.886 | NA | NA | 1473081 | 1765109 | 0.139 | 4.8909 |
| B211 | NA | 52.935 | NA | NA | 329416 | 1128693 | 0.049 | 4.8927 |
| B218 | NA | 77.648 | NA | NA | 1039019 | 2439216 | 0.071 | 4.8930 |
| B249 | NA | 91.092 | NA | NA | 597510 | 1197560 | 0.083 | 4.8929 |
| B348 | NA | 65.394 | NA | NA | 867110 | 2412290 | 0.060 | 4.8935 |
| B379 | NA | 149.254 | NA | NA | 984468 | 1208202 | 0.136 | 4.8933 |
| B416 | NA | 137.946 | NA | NA | 873145 | 1158959 | 0.126 | 4.8937 |
| B417 | NA | 119.721 | NA | NA | 3160264 | 4829324 | 0.109 | 4.8927 |
| B50 | NA | −0.596 | NA | NA | 3075 | 2010696 | 0.000 | 4.9146 |
| B77 | NA | 65.086 | NA | NA | 805769 | 2252079 | 0.060 | 4.8948 |
| B793 | NA | 102.335 | NA | NA | 726520 | 1297409 | 0.093 | 4.8942 |
| B875 | NA | 81.439 | NA | NA | 1183494 | 2650382 | 0.074 | 4.8927 |
| B96 | NA | 60.352 | NA | NA | 974518 | 2934438 | 0.055 | 4.8933 |

Patient Data Summary

| Sample ID # | Tamoxifen | 4-OH-Tamoxifen | 4'-OH-Tamoxifen | N-DM-Tamoxifen | N-DM-4'-OH Tamoxifen | Endoxifen | Norendoxifen |
|---|---|---|---|---|---|---|---|
| 45301 | 130.875 | 1.778 | 4.590 | 26.273 | 3.852 | 19.943 | 5.074 |
| 45390 | 142.588 | 2.672 | 8.253 | 39.710 | 9.206 | 17.691 | 7.059 |
| 45466 | 51.861 | 0.965 | 3.246 | 14.131 | 3.310 | 15.559 | 4.693 |
| 45485 | 2.025 | 0.487 | 0.591 | 2.104 | 1.092 | 1.168 | 1.957 |
| 45569 | −0.642 | NA | 0.019 | −0.438 | −0.222 | NA | 0.564 |
| 45634 | 79.422 | 0.873 | 3.033 | 18.338 | 2.705 | 14.921 | 3.811 |
| 45717 | 114.657 | 2.677 | 4.887 | 10.770 | 2.395 | 60.815 | 4.888 |
| 45750 | 26.715 | 0.612 | 2.940 | 4.916 | 2.489 | 5.976 | 3.368 |
| 45752 | 103.765 | 1.911 | 6.298 | 23.367 | 5.130 | 12.995 | 5.275 |
| 45798 | 35.068 | 0.740 | 2.022 | 8.081 | 1.968 | 3.777 | 2.611 |
| 45800 | 50.405 | 1.669 | 5.486 | 12.381 | 6.013 | 12.760 | 7.030 |
| 45810 | 115.360 | 1.866 | 3.438 | 21.579 | 3.861 | 32.991 | 4.740 |
| 45825 | 179.654 | 1.142 | 6.583 | 33.817 | 5.314 | 20.421 | 4.487 |
| 45835 | 116.025 | 2.009 | 3.962 | 11.219 | 1.776 | 29.102 | 3.337 |
| 45867 | 90.584 | 1.537 | 3.108 | 12.834 | 2.016 | 29.304 | 4.865 |
| 45946 | 68.180 | 1.175 | 5.147 | 12.791 | 3.843 | 16.281 | 5.364 |
| 46037 | 122.733 | 2.761 | 5.643 | 10.380 | 2.595 | 59.095 | 4.910 |
| 46147 | 245.606 | 1.436 | 8.247 | 44.324 | 5.977 | 24.870 | 4.687 |
| 46153 | 64.050 | 1.205 | 3.098 | 13.246 | 2.827 | 17.213 | 3.271 |
| 46180 | 45.657 | 0.924 | 3.884 | 13.893 | 4.240 | 6.037 | 3.156 |
| 46213 | 39.700 | 2.014 | 2.493 | 13.928 | 3.511 | 7.792 | 4.534 |
| 46221 | 60.817 | 1.115 | 3.541 | 26.106 | 5.312 | 16.512 | 5.436 |
| 46283 | 106.601 | 1.252 | 3.892 | 24.324 | 4.666 | 12.331 | 3.605 |
| 46301 | 175.670 | 1.076 | 5.251 | 29.768 | 5.016 | 9.789 | 2.748 |
| 46428 | 102.971 | 1.898 | 3.622 | 9.931 | 1.865 | 25.805 | 3.573 |
| 46442 | 34.971 | 0.620 | 2.922 | 6.573 | 2.995 | 6.342 | 3.827 |
| 46453 | 76.528 | 0.864 | 2.527 | 14.676 | 2.028 | 13.113 | 2.850 |
| 46484 | 134.492 | 1.441 | 3.743 | 15.352 | 2.667 | 30.740 | 4.162 |
| 46518 | 32.697 | 0.721 | 3.108 | 5.940 | 3.264 | 8.837 | 6.699 |
| 46541 | 77.359 | 1.187 | 4.711 | 12.145 | 3.176 | 17.268 | 3.617 |
| 46548 | 85.387 | 1.205 | 4.970 | 17.369 | 5.486 | 7.076 | 3.513 |
| 46606 | 59.848 | 0.842 | 2.090 | 13.382 | 2.749 | 9.943 | 3.175 |
| 46667 | 135.598 | 5.743 | 10.765 | 54.075 | 16.979 | 23.458 | 12.284 |
| 46717 | 182.112 | 1.902 | 7.253 | 32.189 | 5.665 | 22.140 | 5.021 |
| 46731 | 145.655 | 0.965 | 4.273 | 23.463 | 5.254 | 9.207 | 3.454 |

-continued

| Sample ID # | Tamoxifen | 4-OH-Tamoxifen | 4'-OH-Tamoxifen | N-DM-Tamoxifen | N-DM-4'-OH Tamoxifen | Endoxifen | Norendoxifen |
|---|---|---|---|---|---|---|---|
| 46735 | 60.560 | 1.081 | 2.919 | 10.658 | 2.891 | 17.339 | 4.412 |
| 46749 | 97.135 | 1.764 | 3.876 | 18.278 | 3.681 | 25.845 | 4.007 |
| 46841 | 91.310 | 1.679 | 3.195 | 23.201 | 3.203 | 43.515 | 4.586 |
| 46859 | 129.621 | 3.643 | 6.391 | 35.736 | 7.708 | 21.258 | 8.215 |
| 46870 | 94.153 | 2.574 | 3.938 | 9.464 | 2.031 | 59.243 | 5.910 |
| 46896 | 152.754 | 1.602 | 6.647 | 39.389 | 7.929 | 9.876 | 5.884 |
| 46915 | 2.000 | 0.189 | 0.314 | 1.258 | 0.712 | 2.050 | 3.135 |
| B1121 | −0.601 | 0.014 | −0.011 | −0.449 | −0.140 | 0.264 | 0.617 |
| B423 | 140.264 | 2.679 | 7.737 | 33.052 | 5.703 | 42.457 | 11.239 |
| B599 | 68.107 | 0.976 | 5.042 | 15.587 | 4.554 | 6.927 | 2.742 |
| B614 | 74.326 | 1.309 | 3.958 | 14.595 | 3.299 | 26.725 | 6.162 |
| B651 | 63.727 | 0.571 | 3.046 | 17.086 | 4.085 | 9.597 | 5.964 |
| B702 | 67.581 | 1.861 | 3.499 | 20.529 | 4.310 | 24.278 | 7.953 |
| 46917 | 114.854 | 1.781 | 6.294 | 26.132 | 5.430 | 10.963 | 3.918 |
| 46951 | 142.801 | 2.110 | 6.037 | 17.249 | 3.246 | 40.458 | 7.199 |
| 46960 | 98.319 | 0.564 | 4.332 | 18.233 | 3.288 | 9.167 | 4.594 |
| 46990 | 28.847 | 0.516 | 3.019 | 4.714 | 2.314 | 5.317 | 1.989 |
| 47076 | 101.708 | 1.806 | 4.647 | 17.044 | 2.692 | 28.357 | 4.324 |
| 47148 | 59.043 | 0.966 | 3.378 | 10.751 | 2.377 | 19.781 | 4.055 |
| 47204 | 102.845 | 0.580 | 4.003 | 21.609 | 3.480 | 11.477 | 6.512 |
| 47223 | 78.569 | 1.250 | 5.265 | 26.069 | 6.264 | 17.728 | 5.223 |
| 47259 | 114.884 | 0.793 | 4.429 | 24.482 | 4.635 | 14.089 | 3.709 |
| 47262 | 46.850 | 0.562 | 2.216 | 11.522 | 2.477 | 9.176 | 3.248 |
| 47271 | 82.980 | 1.230 | 3.533 | 16.032 | 3.110 | 20.053 | 3.197 |
| 47285 | 54.159 | 0.606 | 2.812 | 10.523 | 2.169 | 8.497 | 2.922 |
| 47287 | 36.896 | 0.913 | 4.284 | 7.253 | 2.942 | 11.271 | 5.726 |
| 47294 | 84.735 | 1.479 | 6.148 | 23.672 | 4.107 | 28.117 | 8.311 |
| 47296 | 104.447 | 1.532 | 6.503 | 25.731 | 5.416 | 11.705 | 5.398 |
| 47362 | 115.191 | 1.411 | 6.575 | 30.720 | 5.126 | 22.343 | 4.939 |
| 47398 | 28.116 | 0.550 | 1.552 | 11.900 | 1.966 | 10.628 | 3.597 |
| 47408 | 102.226 | 2.128 | 4.236 | 14.802 | 2.134 | 38.171 | 3.988 |
| 47429 | 56.922 | 0.848 | 2.437 | 11.723 | 2.483 | 20.228 | 7.582 |
| 47478 | 143.152 | 1.224 | 6.839 | 26.901 | 6.114 | 14.565 | 7.589 |
| 47507 | 131.205 | 0.642 | 5.091 | 25.265 | 4.416 | 7.048 | 3.479 |
| 47512 | 85.263 | 0.779 | 5.454 | 22.956 | 5.723 | 5.756 | 2.200 |
| 47547 | 221.439 | 1.777 | 8.056 | 39.779 | 6.325 | 22.285 | 5.877 |
| 47555 | 72.270 | 0.968 | 3.667 | 15.859 | 3.213 | 11.421 | 0.709 |
| 47583 | 42.391 | 1.163 | 6.473 | 8.888 | 3.863 | 10.629 | 7.439 |
| 47586 | 136.423 | 1.214 | 5.818 | 30.921 | 5.091 | 7.639 | 2.995 |
| 47626 | 84.268 | 0.511 | 3.746 | 18.322 | 3.172 | 8.915 | 9.121 |
| 47629 | 42.703 | 0.374 | 3.136 | 5.135 | 2.413 | 5.126 | 2.355 |
| 47633 | 80.594 | 0.784 | 3.606 | 12.866 | 1.604 | 23.162 | 6.992 |
| 47674 | −0.750 | −0.071 | 0.093 | −0.454 | −0.234 | 0.223 | 2.439 |
| 47696 | 119.835 | 1.648 | 3.824 | 16.209 | 2.188 | 32.499 | 4.597 |
| 47715 | 132.525 | 1.562 | 5.750 | 13.470 | 2.948 | 24.293 | 4.958 |
| B109 | 24.561 | 0.040 | 1.524 | 11.432 | 2.366 | 1.434 | 2.485 |
| B124 | 87.045 | 1.935 | 8.718 | 14.692 | 3.990 | 25.290 | 6.882 |
| B138 | 97.370 | 1.675 | 3.821 | 22.437 | 2.896 | 37.164 | 4.369 |
| B151 | 94.329 | 0.461 | 4.594 | 21.416 | 3.940 | 7.651 | 3.439 |
| B174 | 56.169 | 1.006 | 2.520 | 10.349 | 1.803 | 9.252 | 3.782 |
| B209 | 152.886 | 1.928 | 6.388 | 14.006 | 2.088 | 33.909 | 33.557 |
| B211 | 52.935 | 0.557 | 3.127 | 11.346 | 2.399 | 11.457 | 0.686 |
| B218 | 77.648 | 1.382 | 3.539 | 14.915 | 2.274 | 19.591 | 2.085 |
| B249 | 91.092 | 0.929 | 5.207 | 15.747 | 2.646 | 18.802 | 1.890 |
| B348 | 65.394 | 0.420 | 3.459 | 15.742 | 2.069 | 10.935 | 1.837 |
| B379 | 149.254 | 1.016 | 6.245 | 16.374 | 3.163 | 32.589 | 6.254 |
| B416 | 137.946 | 1.436 | 3.862 | 13.889 | 1.218 | 26.686 | 0.898 |
| B417 | 119.721 | 1.334 | 4.720 | 17.747 | 2.352 | 18.884 | 0.363 |
| B50 | −0.596 | −0.104 | 0.111 | −0.344 | −0.128 | NA | 0.088 |
| B77 | 65.086 | 0.589 | 4.677 | 13.213 | 4.478 | 4.298 | NA |
| B793 | 102.335 | 1.034 | 5.094 | 16.843 | 3.572 | 17.569 | 1.393 |
| B875 | 81.439 | 0.557 | 3.932 | 19.567 | 3.907 | 10.613 | 2.350 |
| B96 | 60.352 | 0.437 | 2.546 | 9.888 | 2.496 | 14.510 | 15.071 |

The contents of the articles, patents, patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for determining an amount of N-Desmethyl Tamoxifen in a human sample by mass spectrometry, comprising:
   (a) purifying the sample by liquid chromatography;
   (b) ionizing N-Desmethyl Tamoxifen in the sample to produce one or more ions detectable by mass spectrometry; and
   (c) detecting an amount of the ion(s) from step (b) by mass spectrometry; wherein the amount of the ion(s) detected is related to the amount of N-Desmethyl Tamoxifen in said sample,
   wherein the method has a limit of quantitation of less than or equal to 1.5 ng/mL.

2. The method of claim 1, further comprising protein precipitation prior to step (a).

3. The method of claim 1, further comprising filtration prior to step (a).

4. The method of claim 1, wherein said liquid chromatography is high pressure liquid chromatography (HPLC).

5. The method of claim 1, wherein said liquid chromatography is high turbulence liquid chromatography (HTLC).

6. The method of claim 1, wherein said ionization is in positive ion mode.

7. The method of claim 1, wherein said sample is a serum or plasma sample.

8. The method of claim 1, wherein said mass spectrometry is tandem mass spectrometry.

9. The method of claim 1, wherein further comprising determining an amount of metabolites selected from the group consisting of tamoxifen, norendoxifen, endoxifen, 4'-Hydroxy Tamoxifen, 4-Hydroxy Tamoxifen, and N-Desmethyl-4'-Hydroxy Tamoxifen.

* * * * *